US006492427B2

(12) United States Patent
Shankar et al.

(10) Patent No.: US 6,492,427 B2
(45) Date of Patent: *Dec. 10, 2002

(54) METHODS FOR TREATING MULTIPLE SCLEROSIS

(76) Inventors: L. Sai Latha Shankar, 323 E. 88th St., Apt. 19, New York, NY (US) 10128; William G. Tatton, 8 Halliday Ct., Purchase, NY (US) 10577; Nadine A. Tatton, 8 Halliday Ct., Purchase, NY (US) 10577

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 23 days.

(21) Appl. No.: 09/416,010

(22) Filed: Oct. 8, 1999

(65) Prior Publication Data

US 2002/0022661 A1 Feb. 21, 2002

Related U.S. Application Data

(60) Provisional application No. 60/103,742, filed on Oct. 9, 1998.

(51) Int. Cl.$^7$ .............................................. A61K 31/135
(52) U.S. Cl. ..................... 514/646; 514/647; 514/654
(58) Field of Search ................................. 514/646, 647, 514/651, 654

(56) References Cited

U.S. PATENT DOCUMENTS

| 5,444,095 A | 8/1995 | Tatton et al. ................ 514/654 |
| 5,844,003 A | * 12/1998 | Tatton et al. ................ 514/654 |

FOREIGN PATENT DOCUMENTS

| WO | WO 96/22068 | 7/1996 |
| WO | WO 96/40095 | 12/1996 |
| WO | WO 97/25421 | 7/1997 |
| WO | WO 97/28791 | 8/1997 |

OTHER PUBLICATIONS

Dorland's Illustrated Medical Dictionary, 28th Edition, p. 1174, 1988.*
Bernheimer, H. et al. (1973) "Brain Dopamine and the Syndromes of Parkinson and Huntington. Clinical, Morphological and Neurochemical Correlations" *Journal of the Neurological Sciences* 29:415–455.
Birkmayer, W. et al. (1983) "(–)–Deprenyl Leads to Prologation of L–Dopa Efficacy in Parkinson's Disease" *Mod. Probl. Pharmacopsychiat.* 19:170–176.
Birkmayer, W. and P. Riederer (1984) "Deprenyl Prolongs the Therapeutic Efficacy of Combined L–DOPA in Parkinson's Disease" *Advances in Neurology* 40:475–481.
Birkmayer, W. et al. (1985) "Increased Life Expectancy Resulting from Addition of L–Deprenyl to Madopar® treatment in Parkinson's Disease: A Longterm Study" *J. Neural Transm.* 64:113–127.

Birkmayer, W. et al. (1975) "The Potentiation of the Anti Akinetic Effect after L–Dopa Treatment by an Inhibitor of Mao–B, Deprenil" *Journal of Neural Transmission* 36:303–326.
Cedarbaum, Jesse M. et al. (1989) "A double–blind crossover comparison of Sinement CR4 and standard Sinemet 25/100 in patients with Parkinson's disease and fluctuating motor performance" *Journal of Neurology, Neurosurgery, and Psychiatry* 52:207–212.
Elizan, Teresita S. et al. (Dec. 1989) "Selegiline as an Adjunct to Conventional Levodopa Therapy in Parkinson's Disease" *Arch Neurol.* 46:1280–1283.
Fischer, P.–A. and H. Baas (1987) "Therapeutic efficacy of R–(—)–deprenyl as adjuvant therapy in advanced parkinsonism" *J. Neural Transm.* [suppl.] 25:137–147.
Golbe, Lawrence I. (Aug. 1989) "Long–term efficacy and safety of deprenyl (selegiline) in advanced Parkinson's disease" *Neurology* 39:1109–1111.
Golbe, Lawrence I. (1990) "Selegiline and Parkinson's Disease. Protective and Symptomatic Considerations" *Drugs* 39(5):646–651.
Lieberman, Abraham N. et al. (1987) "Deprenyl versus placebo in Parkinson disease: A double–blind study" *New York State Journal of Medicine* 87:646–649.
Mitrovic, Branislava et al. (1996) "An in Vitro Model of Oligodendrocyte Destruction by Nitric Oxide and Its Relevance to Multiple Sclerosis" *Methods: A Companion to Methods in Enzymology* 10:501–513.
Parkinson Study Group (Oct. 1989) "Datatop: A Multicenter Controlled Clinical Trial in Early Parkinson's Disease" *Arch. Neurol.* 46–1052–1060.
The Parkinson Study Group (Nov. 16, 1989) "Effect of Deprenyl on the Progression of Disability in Early Parkinson's Disease" *The New England Journal of Medicine* 321(20):1364–1371.
Raine, Cedric S. (1997) "The Norton Lecture: A Review of the Oligodendrocyte in the Multiple Sclerosis Lesion" *Journal of Neuroimmunology* 77:135–152.
Shankar, S.L. (1995) "R(-)–Deprenyl Increases Survival and Process Complexity of Oligodendrocytes In Vitro" 25th Annual Meeting of the Society for Neuroscience, San Diego, California, USA, Nov. 11–16, 1995. *Society for Neuroscience Abstracts* 21(1–3):41.
Sketris, I.S. et al. "Drug Therapy in Multiple Sclerosis: A Study of Nova Scotia Senior Citizens" *Clinical Therapeutics* 18(2):303–318 (1996).
Tatton, W.G. and R.M.E. Chalmers–Redman (1996) "Modulation of gene expression rather than monoamine oxidase inhibition: (-)–Deprenyl–related compounds in controlling neurodegeneration" *Neurology* 47(Suppl 3):S171–S183.

* cited by examiner

*Primary Examiner*—Theodore J. Criares
*Assistant Examiner*—Jennifer Kim
(74) *Attorney, Agent, or Firm*—Lahive & Cockfield, LLP; Elizabeth A. Hanley; Merideth C. Arnold

(57) ABSTRACT

Methods for increasing oligodendrocyte survival are disclosed. The methods of the invention are useful for the treatment of Multiple Sclerosis.

17 Claims, 16 Drawing Sheets

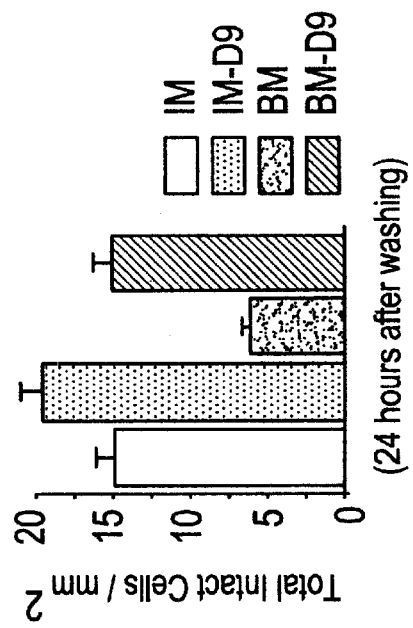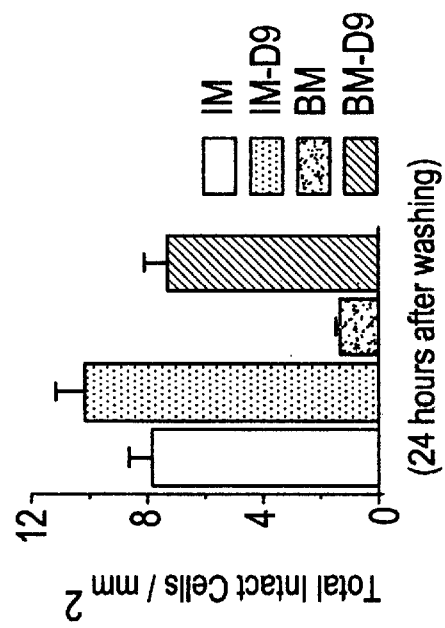
FIG. 3A-1  FIG. 3A-2
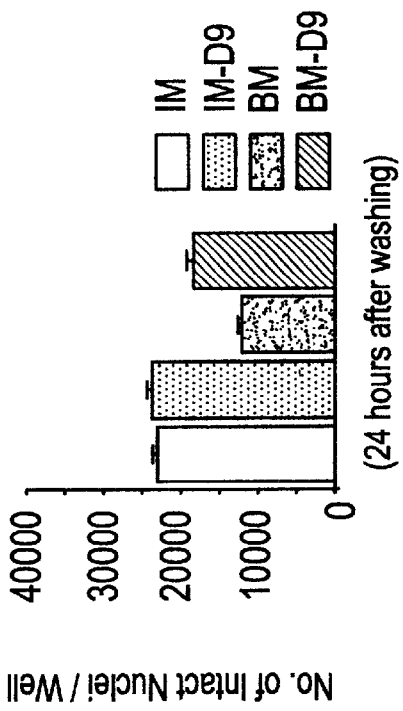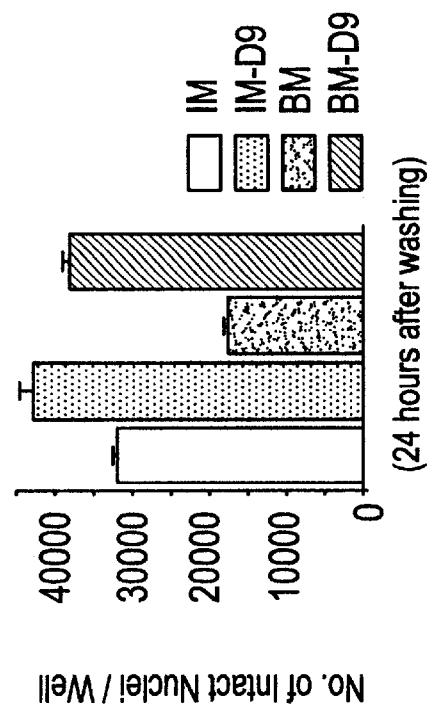
FIG. 3B-1  FIG. 3B-2

(24 hours after washing)

(24 hours after washing)

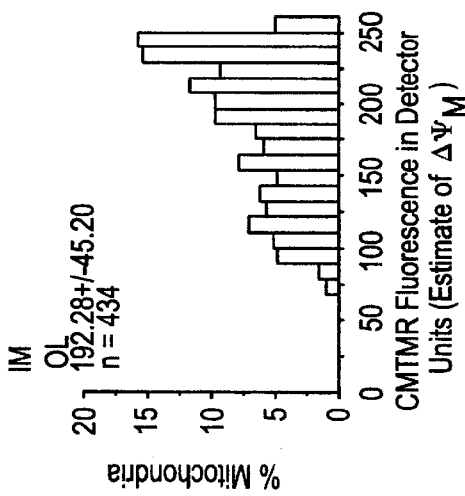
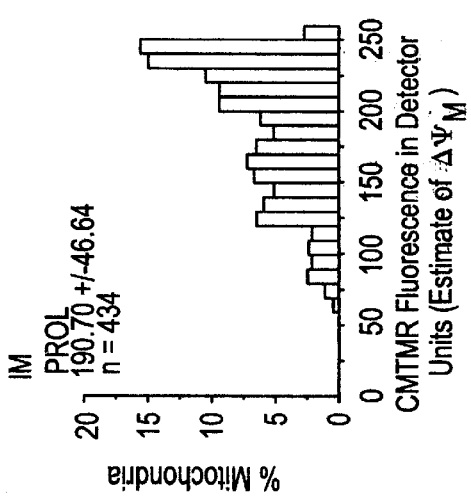
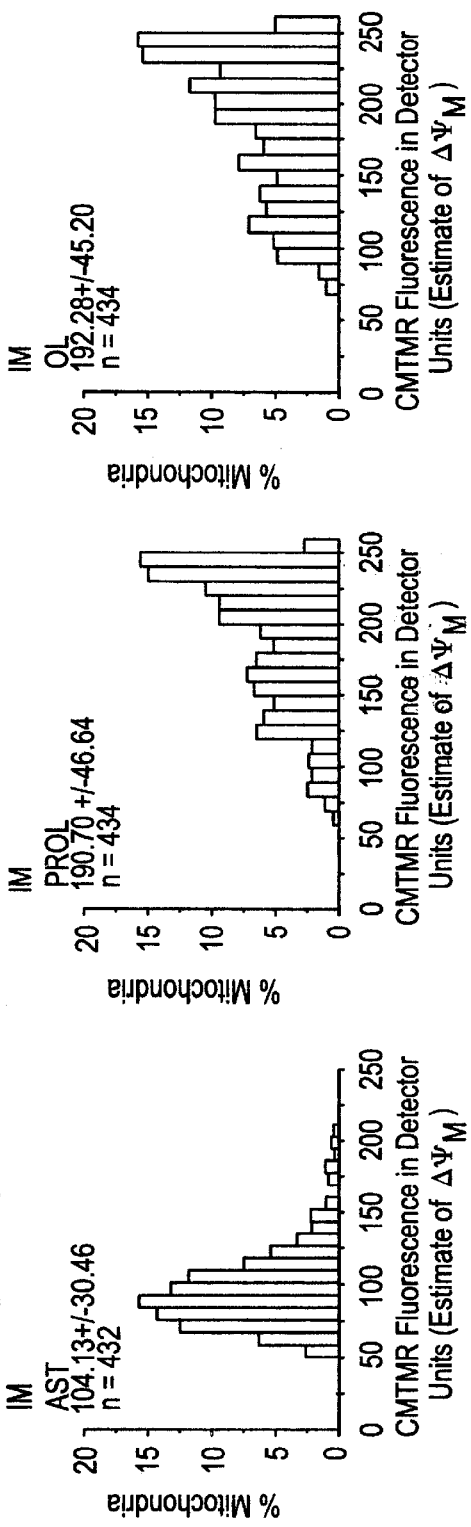
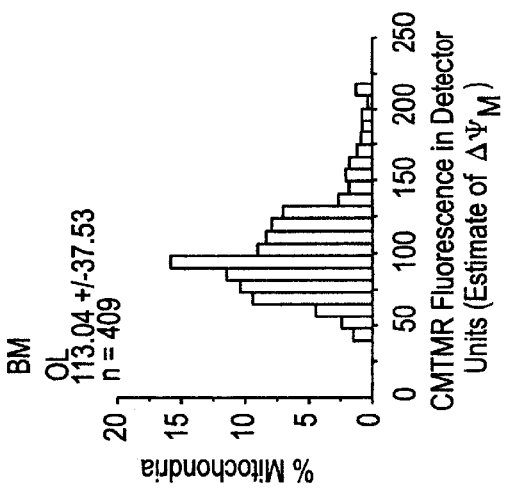
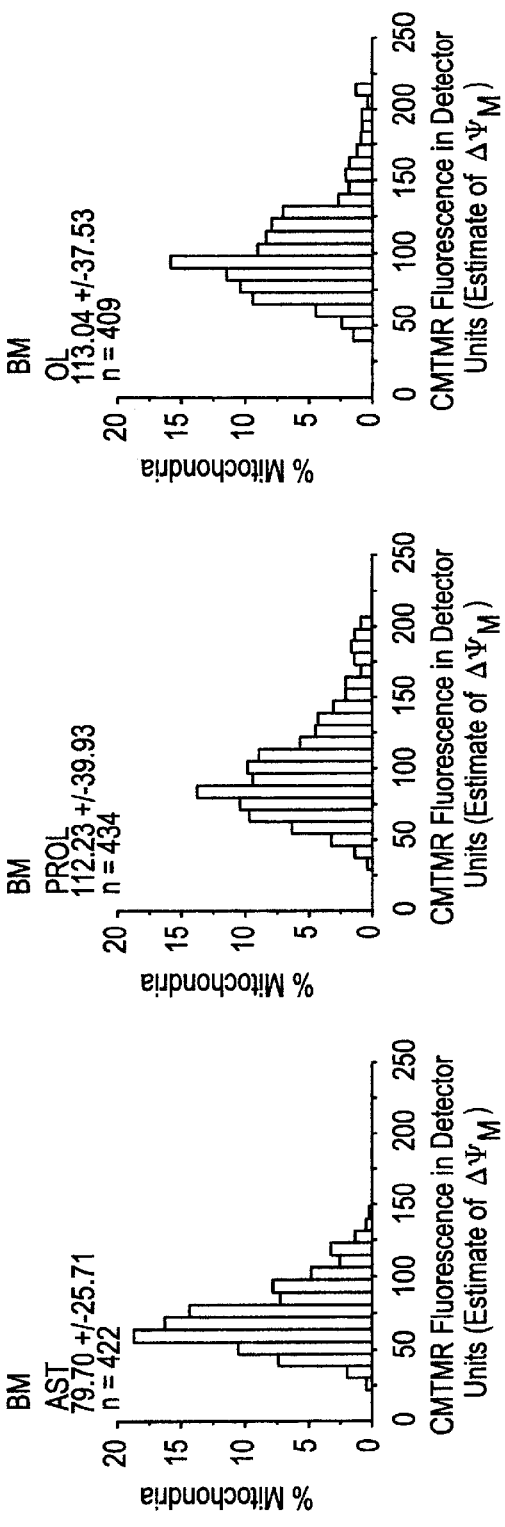

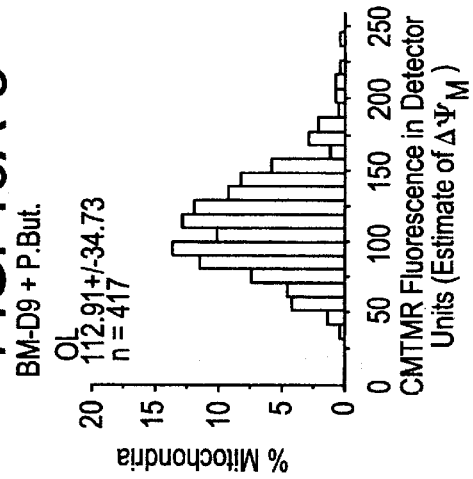
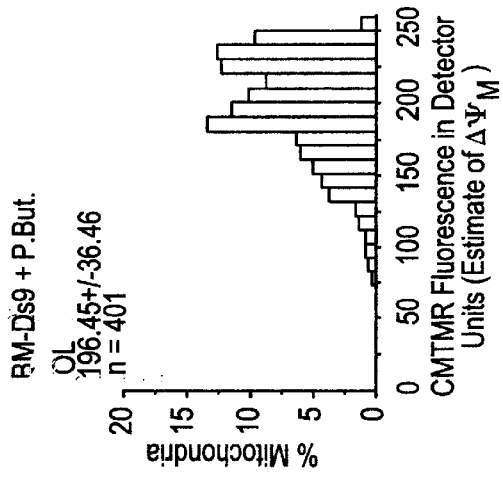
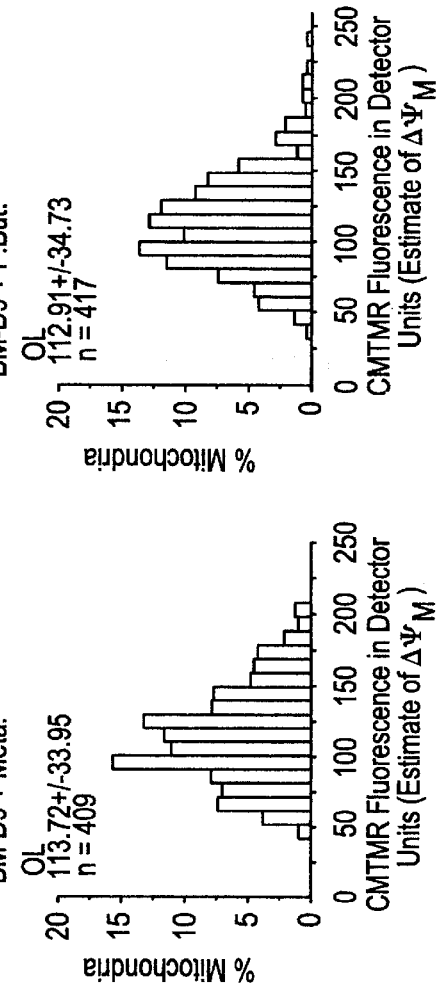
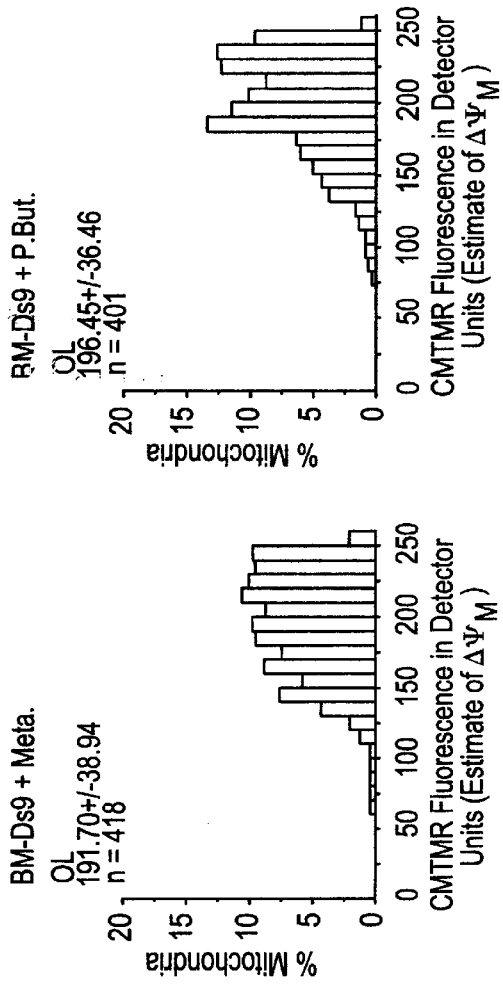
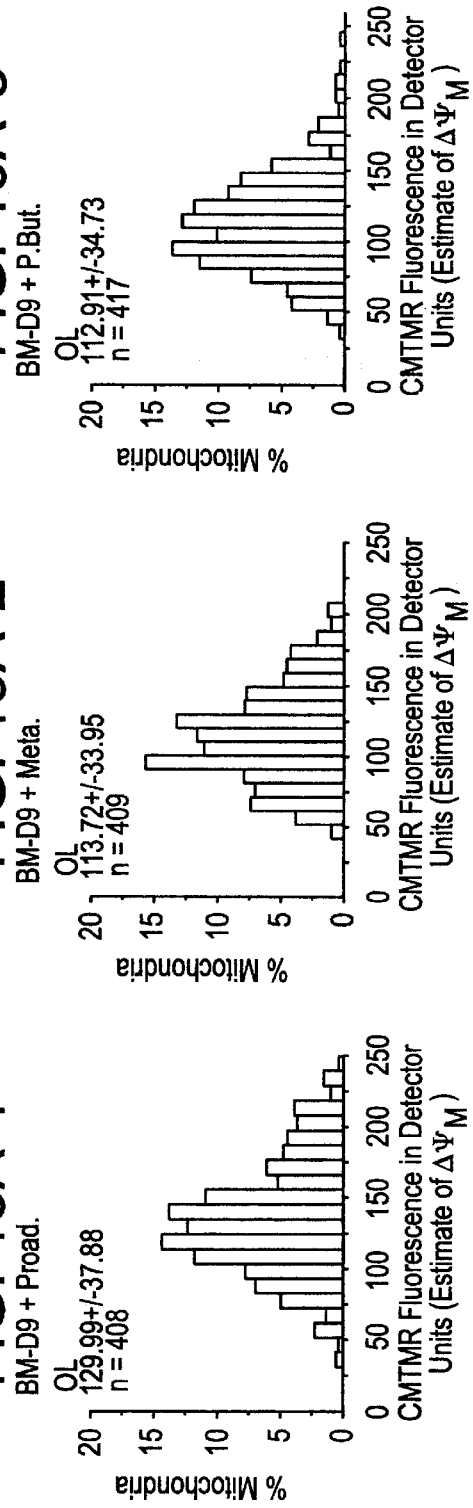
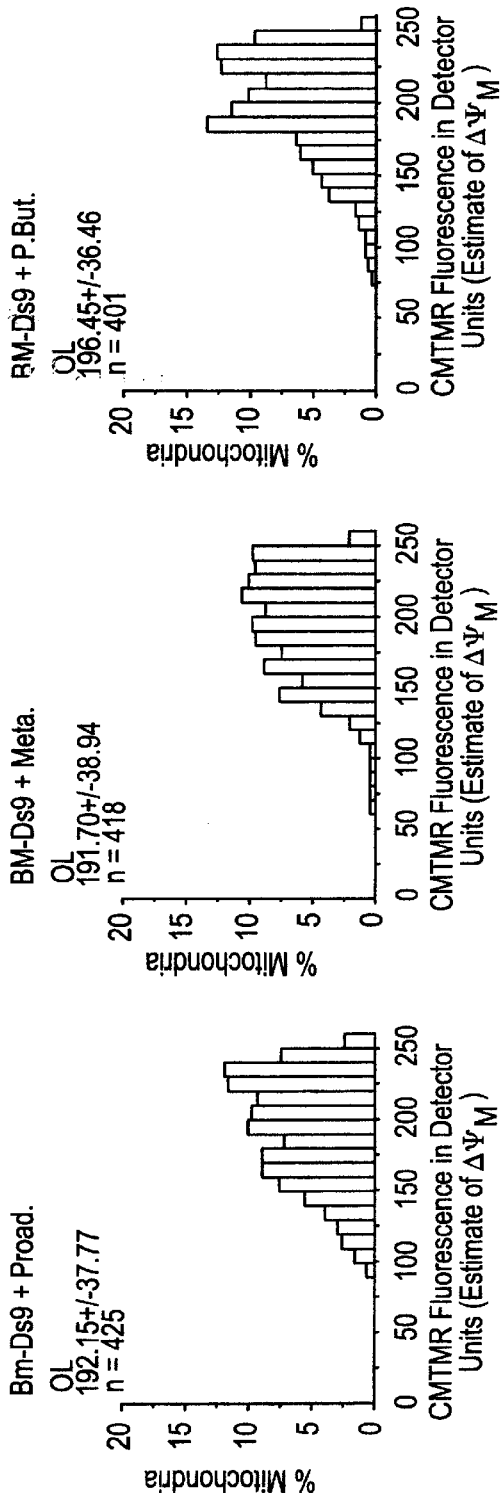

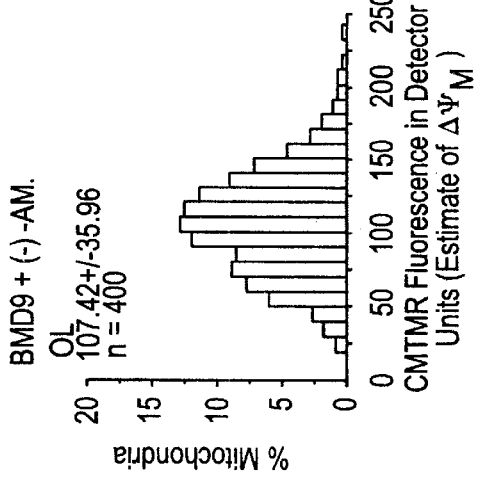
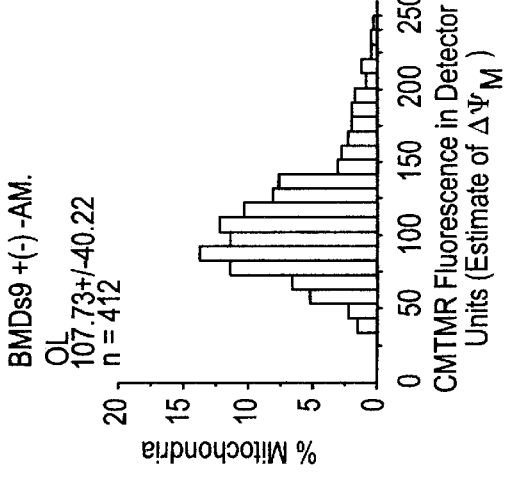
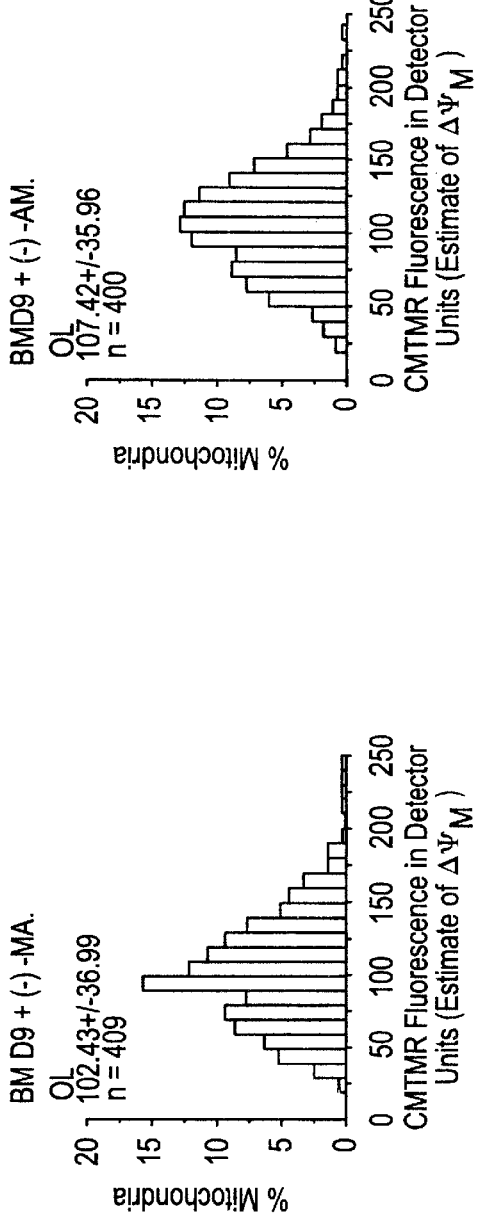
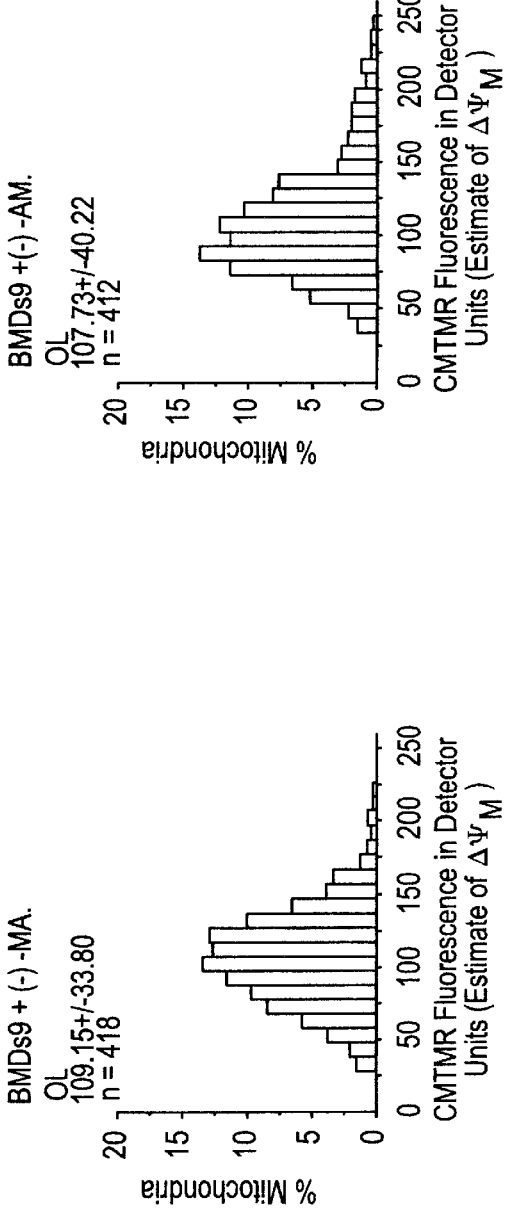

METHODS FOR TREATING MULTIPLE SCLEROSIS

RELATED APPLICATIONS

This application claims the benefit of priority under 35 U.S.C. 119(e) to co-pending U.S. Provisional Application No. 60/103,742, filed on Oct. 9, 1998, the entire contents of which is hereby incorporated by reference.

BACKGROUND OF THE INVENTION

Deprenyl (also referred to herein as selegiline or R-(–)-N,α-Dimethyl-N-2-propynyl phenethylamine) was first used as an adjunct to conventional drug therapy (L-dihydroxyphenylalanine (L-DOPA) plus a peripheral decarboxylase inhibitor) of Parkinson's disease (PD) in Europe over a decade ago on the basis that as a selective monoamine oxidase-B (MAO-B) inhibitor, it would elevate brain dopamine levels and potentiate the pharmacological action of dopamine formed from L-DOPA, and yet prevent the tyramine-pressor effect observed with non-selective MAO inhibitors. The combined drug therapy was reported to prolong the anti-akinetic effects of L-DOPA, resulting in the disappearance of on-off effects, reduced functional disability, and increased life-expectancy in PD patients (Bernheimer, H., et al., J. Neurolog. Sci., 1973. 20: 415–455, Birkmayer, W., et al., J. Neural Transm., 1975. 36:303–336, Birkmayer, W., et al., Mod. Prob. Pharmacopsychiatr., 1983. 19: 170–177, Birkmayer, W. and P. Riederer, Hassler, R. G. and J. F. Christ (Ed.) Advances In Neurology, 1984. 40(Y): p.0–89004, and Birkmayer, W., et al., J. Neural Transm., 1985. 64(2): p. 113–128).

Studies examining deprenyl as an adjunct to conventional L-DOPA therapy have reported a short term benefit which was usually lost by 1 year or less. Some, but not all, have reported that the levodopa dose can be decreased when taken in conjunction with deprenyl (Elizan, T. S., et al., Arch Neurol, 1989. 46(12): p. 1280–1283, Fischer, P. A. and H. Baas, J. Neural Transm. (suppl.), 1987. 25: p. 137–147, Golbe, L. I., Neurology, 1989. 39: p. 1109–1111, Lieberman, A. N. et al., N.Y. State J. Med., 1987. 87: p. 646–649, Poewe, W., F. Gerstenbrand, and G. Ransomayr, J. Neural Transm. (suppl.), 1987. 25: p. 137–147, Cedarbaum, J. M., M. Hoey, and F. H. McDowell, J. Neurol. Neurosurg. Psychiatry, 1989. 52(2): p. 207–212, and Golbe, L. I., J. W. Langston, and I. Shoulson, Drugs, 1990. 39(5): p. 646–651).

Increasingly, deprenyl is being administered to Parkinson's disease patients following reports (Parkinson, S. G. Arch Neurol 46, 1052–1060 (1989) and U.S.A., Parkinson, S. G. N. Engl. J. Med. 321, 1364–1371 (1989)) that it delays the disease progression; a mechanism has recently been proposed to explain its action (See, e.g., Tatton & Redman 1996).

SUMMARY OF THE INVENTION

It has now been discovered that certain compounds are capable of increasing survival of oligodendrocytes. The invention provides methods for increasing survival of oligodendrocytes both in vivo and in vitro, of preventing or inhibiting death of oligodendrocytes, of preventing or inhibiting the progression of Multiple Sclerosis, and methods for treating Multiple Sclerosis.

In one aspect, the invention provides a method for increasing survival of oligodendrocytes. The method comprises administering to a subject in need thereof an effective amount of a deprenyl compound such that survival of oligodendrocytes is increased. In certain embodiments, the deprenyl compound is represented by the structure:

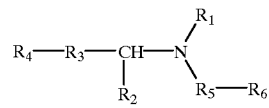

in which

R$_1$ is hydrogen, alkyl, alkenyl, alkynyl, aralkyl, alkylcarbonyl, arylcarbonyl, alkoxycarbonyl, or aryloxycarbonyl;

R$_2$ is hydrogen or alkyl;

R$_3$ is a single bond, alkylene, or —(CH$_2$)$_n$—X—(CH$_2$)$_m$; in which X is O, S, or N-methyl; m is 1 or 2; and n is 0,1, or 2;

R$_4$ is alkyl, alkenyl, alkynyl, heterocyclyl, aryl or aralkyl; and

R$_5$ is alkylene, alkenylene, alkynylene and alkoxylene; and

R$_6$ is C$_3$–C$_6$ cycloalkyl or

or

R$_2$ and R$_4$–R$_3$ are joined to form, together with the methine to which they are attached, a cyclic or polycyclic group;

and pharmaceutically acceptable salts thereof. In certain embodiments: R$_1$ is a group that can be removed in vivo; R$_1$ is hydrogen; R$_1$ is alkyl; R$_1$ is methyl; R$_2$ is methyl; R$_3$ is methylene; wherein R$_4$ is aryl; R$_4$ is phenyl; R$_5$ is methylene; R$_6$ is

In certain preferred embodiments, the deprenyl compound is represented by the structure:

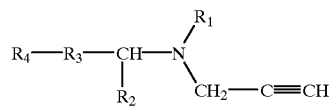

in which

R$_1$ is hydrogen, alkyl, alkenyl, alkynyl, aralkyl, alkylcarbonyl, arylcarbonyl, alkoxycarbonyl, or aryloxycarbonyl;

R$_2$ is hydrogen or alkyl;

R$_3$ is a bond or methylene; and

R$_4$ is aryl or aralkyl; or

R$_2$ and R$_4$–R$_3$ are joined to form, together with the methine to which they are attached, a cyclic or polycyclic group;

and pharmaceutically acceptable salts thereof.

In certain preferred embodiments, the deprenyl compound is represented by the structure:

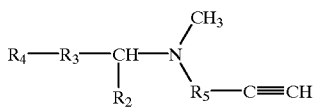

in which
R$_2$ is hydrogen or alkyl;
R$_3$ is a bond or methylene; and
R$_4$ is aryl or aralkyl; or
R$_2$ and R$_4$–R$_3$ are joined to form, together with the methine to which they are attached, a cyclic or polycyclic group; and
R$_5$ is alkylene, alkenylene, alkynylene and alkoxylene;
and pharmaceutically acceptable salts thereof.

In certain preferred embodiments, the deprenyl compound is represented by the structure:

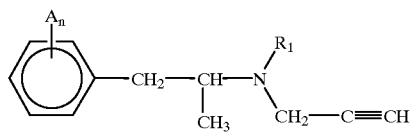

in which
R$_1$ is hydrogen, alkyl, alkenyl, alkynyl, aralkyl, alkylcarbonyl, arylcarbonyl, alkoxycarbonyl, or aryloxycarbonyl;
A is a substituent independently selected for each occurrence from the group consisting of halogen, hydroxyl, alkyl, alkoxyl, cyano, nitro, amino, carboxyl, —CF$_3$, or azido;
n is 0 or an integer from 1 to 5;
and pharmaceutically acceptable salts thereof.

In certain preferred embodiments, the patient is a human. In a particularly preferred embodiment, the deprenyl compound is (-)-desmethyldeprenyl.

In another aspect, the invention provides a method for inhibiting Multiple Sclerosis, comprising administering to a patient an effective amount of a deprenyl compound such that Multiple Sclerosis is inhibited. In a preferred embodiment, the deprenyl compound is (-)-desmethyldeprenyl. In certain embodiments, the patient is a human.

In another aspect, the invention provides a method for increasing oligodendrocyte survival in vitro, comprising contacting oligodendrocytes with an effective amount of a deprenyl compound such that oligodendrocyte survival is increased.

In another aspect, the invention provides a method for increasing oligodendrocyte survival in a patient, comprising contacting a oligodendrocyte with a deprenyl compound such that oligodendrocyte survival increases. In preferred embodiments, the patient is a human; the deprenyl compound is (-)-desmethyldeprenyl; and/or the (-)-desmethyldeprenyl is administered transdermally to the patient.

BRIEF DESCRIPTION OF THE DRAWING

FIG. 6: Insulin and IGF-I withdrawn oligodendrocytes display fragmented process morphology. Cells at 16 DIV were washed and replaced in IM or BM. Panels show transmitted light microscopic images of cells incubated in IM (A1) or in BM (B1) for 18 h. Cells were subsequently fixed in 4% paraformaldehyde and stained with an antibody to myelin basic protein (MBP). Panels (A2) and (B2) are interference contrast micrographs of MBP positive OLs. Note the extensively branched processes of OLs incubated in IM (A1, A2). Cells placed in BM show fragmented processes but display an intact cell body (B1, B2).

FIG. 13: Effects of IGF-I and insulin withdrawal on mitochondrial membrane potential ($\Delta\psi_M$) of oligodendroglial lineage cells. Cells grown on glass coverslips were incubated in IM (A) or BM (B) for 18 h, and then incubated with the potentiometric dye CMTMR (138 nM) for 15 min at 37° C. before fixation with 4% paraformaldehyde on ice for 30 min. Confocal images with constant power and pinhole aperture settings were obtained of each cell type, ASTs, PROLs, OLs. A minimum of 20 images were obtained for each cell type. Using the image acquisition and analysis software Metamorph™, 2 regions within an individual mitochondrion were selected and the fluorescence intensity was measured on a scale of 0–255. No fewer than 20 such regions were measured from each cell. The distribution of CMTMR fluorescence intensity observed in each cell type is shown and the mean intensity±SD is given. Note the higher percentage of mitochondria in ASTs with low CMTMR fluorescence intensity compared to PROLs and OLs grown in IM. Also note the shift to the left in the distribution of CMTMR fluorescence intensity in each cell type when incubated in BM, indicating a reduction in ~M. OLs and PROLs have a high proportion of mitochondria with relatively high level $\Delta\psi_M$.

FIG. 14: Effects of (−)-deprenyl and (−)-desmethyldeprenyl on $\Delta\psi_M$ of oligodendroglial lineage cells. Cells grown on glass coverslips were incubated in BM-D9 (A) or BM-Ds9 (B) for 18 h and stained with CMTMR as before followed by fixation with 4% paraformaldehyde. Confocal images were obtained with constant power and pinhole aperture settings of ASTs, PROLs and ASTs. CMTMR fluorescence intensity values were obtained as described using the Metamorph image analysis software from 20 individual mitochondria within 20 cells. Values are the mean±SD intensity of CMTMR fluorescence. Also shown are frequency distributions of mitochondrial CMTMR fluorescence in each treatment. Note that both (−)-deprenyl and (−)-desmethyldeprenyl prevented the decrease in $\Delta\psi_M$.

FIG. 15: Effects of general cytochrome P450 blockers on (−)-deprenyl and (−)-desmethyldeprenyl induced changes in $\Delta\psi_M$. OLs grown on glass coverslips were incubated in BM supplemented with $10^{-9}$M (−)-deprenyl or (−)-desmethyldeprenyl and treated with the general cytochrome P450 blockers proadifen, metapyrone, or piperonyl butoxide for 18 h. At the end of the treatment period cells were incubated with CMTMR as before and fixed in 4% paraformaldehyde. Confocal images were obtained using constant power and pinhole aperture settings and CMTMR intensity was measured using the Metamorph image analysis software from 20 individual mitochondria within 20 cells per group. Values represent the mean±SD intensity of CMTMR fluorescence. The frequency distributions of mitochondrial CMTMR fluorescence are also shown. Note that treatment with general cytochrome P450 blockers prevented the maintenance of $\Delta\psi_M$ provided by (−)-deprenyl but not by (−)-desmethyldeprenyl, indicating that metabolism of (−)-deprenyl to (−)-desmethyldeprenyl is necessary for its protective effects.

FIG. 16: Effects of (−)-methamphetamine and (−)-amphetamine on (−)-deprenyl and (−)-desmethyldeprenyl induced changes in $\Delta\psi_M$ of oligodendroglial cells. OLs grown on glass coverslips were incubated in BM for 18 h supplemented with $10^{-9}$ M (−)-deprenyl or (−)-desmethyldeprenyl and treated with $10^{-5}$ M (−)-methamphetamine or $10^{-5}$ M (−)-amphetamine. Cells were incubated with CMTMR as described and fixed in 4% paraformaldehyde. Confocal images were obtained using constant power and pinhole aperutre settings of a minimum of 20 cells per group. CMTMR fluorescence intensity was measured using the Metamorph™ image analysis software from a minimum of 20 individual mitochondria in each cell. Values represent the mean±SD intensity of CMTMR fluorescence. The frequency distributions of mitochondrial CMTMR fluorescence are also shown. Note that the addition of (−)-methamphetamine or (−)-amphetamine to cells incubated in BM supplemented with (−)-deprenyl or (−)-desmethyldeprenyl prevented the maintenance of $\Delta\psi_M$ provided by both (−)-deprenyl and (−)-desmethyldeprenyl.

DETAILED DESCRIPTION OF THE INVENTION

Figure 1A:
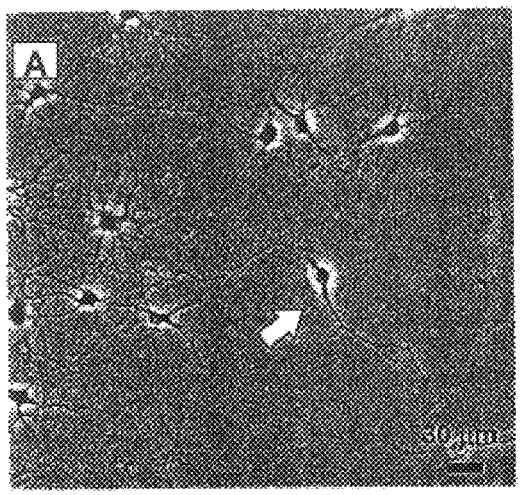
FIG. 1: Progressive maturation of oligodendrocytes in vitro. Phase-contrast microphotographs of oligodendrocytes after 12 (A), 13 (B), 14 (C) and 16 days (D) of culture. 0-2A progenitor cells isolated from postnatal day 2 rat cortex were grown in a chemically defined media supplemented with insulin (5 1 lg/ml) and IGF-I (2.5 ng/ml). Bipolar 0-2As (A) differentiate into multipolar PROLs (B, C) which develop into OLs (D) bearing an extensive network of branching processes. The cell marked by the white arrow in A is a typical 0-2A while typical multiprocessed PROLs are shown in (B) and (C) marked by white arrows. The white arrow in panel (D) marks a typical example of an OL. A 16 DIV culture constituted about 2% 0-2As, 32% PROLs and 62% OLs and 4% AST.

The present invention provides methods for increasing oligodendrocyte survival in a patient or in vitro, or for treating Multiple Sclerosis in a subject suffering from, or susceptible to, Multiple Sclerosis.

The terms "patient" or "subject", as used herein, refer to a warm-blooded animal having damaged glial and/or oligodendrocytes, or suffering from or susceptible to oligodendrocyte damage or death, or suffering from or susceptible to Multiple Sclerosis. In preferred embodiments, the patient is a mammal, including humans and non-human mammals such as dogs, cats, pigs, cows, sheep, goats, rats, and mice. In a particularly preferred embodiment, the patient is a human. In certain embodiments, the patient is suffering from a condition associated with Multiple Sclerosis, including, but not limited to, diabetes, AIDS, rheumatoid arthritis, or a thyroid disease. The methods of the invention are also useful for preventing or slowing the onset of Multiple Sclerosis or a symptom or condition associated therewith in a patient not yet suffering from Multiple Sclerosis, but susceptible to the development of Multiple Sclerosis. Thus, prophylactic administration of a deprenyl compound can inhibit oligodendrocyte death or development of Multiple Sclerosis in a patient who would otherwise be susceptible to such a condition.

The term "rescue of damaged oligodendrocytes" or "rescuing of damaged glial cells" herein refer to the reversal of the sequence of damage to death in (otherwise) lethally damaged oligodendrocytes (or glial cells). In certain embodiments, "rescue of damaged oligodendrocytes includes prevention of apoptosis in a oligodendrocyte.

The language "increasing survival of oligodendrocytes" as used herein, refers to increasing numbers of oligodendrocytes, preventing death of oligodendrocytes, or otherwise increasing numbers of oligodendrocytes (proliferating or non-proliferating), either in vitro (e.g., in cell culture) or in a subject.

The language "inhibiting Multiple Sclerosis" as used herein, refers to preventing, slowing or reversing the development of Multiple Sclerosis, or a symptom or condition associated therewith. For example, administration of a compound to a subject to inhibit Multiple Sclerosis includes administering a compound such that progression of Multiple Sclerosis is prevented, slowed, or reversed, in whole or in part, or at least one symptom (or development of a symptom) is prevented, slowed, reversed, or otherwise ameliorated.

It is known that deprenyl and deprenyl compounds can rescue, or prevent the death of, damaged nerve cells (see, e.g., U.S. Pat. No. 5,444,095 and International Publication No. WO 97/28791, incorporated herein by reference). However, it is believed that the use of deprenyl or deprenyl compounds to increase the survival of oligodendrocytes, or to rescue, or prevent the death of, oligodendrocytes has not previously been reported.

The methods of the invention find use in treatment of conditions associated with Multiple Sclerosis, as well as in cell culture.

I. Deprenyl Compounds

The language "deprenyl compound", as used herein, includes deprenyl (N,α-dimethyl-N-2-propynylphenethylamine), compounds which are structurally similar to deprenyl, e.g., structural analogs, or derivatives thereof. Thus, in one embodiment, a deprenyl compound can be represented by the following formula (Formula I):

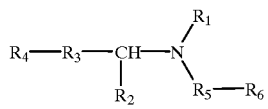

Formula I in which $R_1$ is hydrogen, alkyl, alkenyl, alkynyl, aralkyl, alkylcarbonyl, arylcarbonyl, alkoxycarbonyl, or aryloxycarbonyl;

$R_2$ is hydrogen or alkyl;

$R_3$ is a single bond, alkylene, or —$(CH_2)_n$—X—$(CH_2)_m$; in which X is O, S, or N-methyl; m is 1 or 2; and n is 0,1, or 2;

$R_4$ is alkyl, alkenyl, alkynyl, heterocyclyl, aryl or aralkyl; and $R_5$ is alkylene, alkenylene, alkynylene and alkoxylene; and $R_6$ is $C_3$–$C_6$ cycloalkyl or

or $R_2$ and $R_4$–$R_3$ are joined to form, together with the methine to which they are attached, a cyclic or polycyclic group;

and pharmaceutically acceptable salts thereof.

In certain preferred embodiments, a deprenyl compound is not selected from the group consisting of deprenyl, pargyline, AGN-1133, AGN-1135, or MD 240928.

In preferred embodiments, $R_1$ is a group that can be removed in vivo. In certain embodiments, $R_1$ is hydrogen. In other preferred embodiments, $R_1$ is methyl. In certain preferred embodiments, $R_2$ is hydrogen. In certain preferred embodiments, $R_2$ is methyl. In some preferred embodiments, $R_3$ is alkylene, more preferably methylene. In other preferred embodiments, $R_3$ is —$(CH_2)_n$—X—$(CH_2)_m$. In preferred embodiments, $R_4$ is aryl. In certain preferred embodiments, is phenyl. In other preferred embodiments, $R_4$ is aralkyl. In yet other preferred embodiments, $R_4$ is alkyl. In still other preferred embodiments, $R_5$ is alkylene, more preferably methylene. In certain preferred embodiments, $R_6$ is

—C≡CH.

In other preferred embodiments, $R_6$ is cyclopentyl.

In another preferred embodiment, the deprenyl compound has the structure

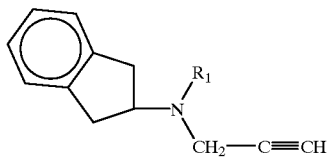

wherein $R_1$ is as described above. Preferred deprenyl compounds include (-)-desmethyldeprenyl, and

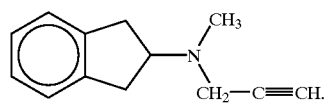

In another embodiment, a deprenyl compound can be represented by the following formula (Formula II):

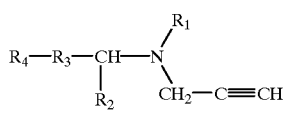

Formula II in which $R_1$ is hydrogen, alkyl, alkenyl, alkynyl, aralkyl, alkylcarbonyl, arylcarbonyl, alkoxycarbonyl, or aryloxycarbonyl;

$R_2$ is hydrogen or alkyl;

$R_3$ is a bond or methylene; and $R_4$ is aryl or aralkyl; or $R_2$ and $R_4$–$R_3$ are joined to form, together with the methine to which they are attached, a cyclic or polycyclic group;

and pharmaceutically acceptable salts thereof.

In another embodiment, the deprenyl compound can be represented by the following formula (Formula III):

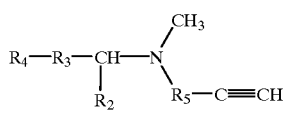

Formula III in which $R_2$ is hydrogen or alkyl;

$R_3$ is a bond or methylene; and $R_4$ is aryl or aralkyl; or $R_2$ and $R_4$–$R_3$ are joined to form, together with the methine to which they are attached, a cyclic or polycyclic group; and $R_5$ is alkylene, alkenylene, alkynylene and alkoxylene; and pharmaceutically acceptable salts thereof.

In yet another embodiment, the deprenyl compound can be represented by the following formula (Formula IV):

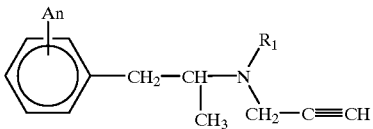

Formula IV in which $R_1$ is hydrogen, alkyl, alkenyl, alkynyl, aralkyl, alkylcarbonyl, arylcarbonyl, alkoxycarbonyl, or aryloxycarbonyl;

A is a substituent independently selected for each occurrence from the group consisting of halogen, hydroxyl, alkyl, alkoxyl, cyano, nitro, amino, carboxyl, —$CF_3$, or azido;

n is 0 or an integer from 1 to 5;

and pharmaceutically acceptable salts thereof.

In certain embodiments of the invention, the deprenyl compound is not deprenyl (including (-)-deprenyl).

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 20 or fewer carbon atoms in its backbone (e.g., $C_1$–$C_{20}$ for straight chain, $C_3$–$C_{20}$ for branched chain), and more preferably 10 or fewer. Likewise, preferred cycloalkyls have from 4–1 0 carbon atoms in their ring structure, and more preferably have 5, 6 or 7 carbons in the ring structure. Unless the number of carbons is otherwise specified, "lower alkyl" as used herein means an alkyl group, as defined above, but having from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The terms "alkenyl" and "alkynyl" refer to unsaturated aliphatic groups analogous in length and possible substitution to the alkyls described above, but that contain at least one double or triple bond respectively.

The term "aralkyl", as used herein, refers to an alkyl or alkylenyl group substituted with at least one aryl group (e.g., an aromatic or heteroaromatic group). Exemplary aralkyls include benzyl (i.e., phenylmethyl), 2-naphthylethyl, 2-(2-pyridyl)propyl, 5-dibenzosuberyl, and the like.

The term "alkylcarbonyl", as used herein, refers to —C(O)-alkyl. Similarly, the term "arylcarbonyl" refers to —C(O)-aryl. The term "alkyloxycarbonyl", as used herein, refers to the group —C(O)—O-alkyl, and the term "aryloxycarbonyl" refers to —C(O)—O-aryl. The term "acyloxy" refers to —O—C(O)—$R_7$, in which $R_7$ is alkyl, alkenyl, alkynyl, aryl, aralkyl or heterocyclyl.

The term "amino", as used herein, refers to —N($R_8$)($R_9$), in which $R_8$ and $R_9$ are each independently hydrogen, alkyl, alkenyl, alkynyl, aralkyl, aryl, or $R_8$ and $R_9$, together with the nitrogen atom to which they are attached, form a ring having 4–8 atoms. Thus, the term "amino", as used herein, includes unsubstituted, monosubstituted (e.g., monoalkylamino or monoarylamino), and disubstituted (e.g., dialkylamino or alkylarylamino) amino groups. The term "amido" refers to —C(O)—N($R_8$)($R_9$), in which $R_8$ and $R_9$ are as defined above. The term "acylamino" refers to —N($R'_8$)C(O)—$R_7$, in which $R_7$ is as defined above and $R'_8$ is alkyl.

As used herein, the term "nitro" means —$NO_2$; the term "halogen" designates —F, —Cl, —Br or —I; the term "sulfhydryl" means —SH; and the term "hydroxyl" means —OH.

The term "aryl" as used herein includes 5-, 6- and 7-membered aromatic groups that may include from zero to four heteroatoms in the ring, for example, phenyl, pyrrolyl, furyl, thiophenyl, imidazolyl, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroaromatics". The aromatic ring can be substituted at one or more ring positions with such substituents as described above for alkyls, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, a heterocyclyl, an aromatic or heteroaromatic moiety, —$CF_3$, —CN, or the like. Aryl groups can also be part of a polycyclic group. For example, aryl groups include fused aromatic moieties such as naphthyl, anthracenyl, quinolyl, indolyl, and the like.

The terms "heterocyclyl" or "heterocyclic group" refer to 4- to 10-membered ring structures, more preferably 4- to 7-membered rings, which ring structures include one to four heteroatoms. Heterocyclyl groups include, for example, pyrrolidine, oxolane, thiolane, imidazole, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycyclic group can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "heteroatom" as used herein means an atom of any element other than carbon or hydrogen. Preferred heteroatoms are nitrogen, oxygen, sulfur and phosphorus.

It will be noted that the structure of some of the compounds of this invention includes asymmetric carbon atoms. It is to be understood accordingly that the isomers arising from such asymmetry are included within the scope of this invention. Such isomers are obtained in substantially pure form by classical separation techniques and by sterically controlled synthesis.

The term "can be removed in vivo", as used herein, refers to a group that can be cleaved in vivo, either enzymatically or non-enzymatically. For example, amides can be cleaved by amidases, and N-methyl amines can be cleaved by enzymatic oxidation. For example, when deprenyl is administered to a subject, it is believed, as described infra, that the methyl group can be removed in vivo to yield an active compound. As a further example, with reference to Formula I, when $R_1$ is alkylcarbonyl, the resulting amide group can be hydrolytically cleaved in vivo, enzymatically or non-enzymatically, to yield a deprenyl compound including a secondary amine (e.g., $R_1$ is converted to hydrogen in vivo). Other groups which can be removed in vivo are known (see, e.g., R. B. Silverman (1992) "The Organic Chemistry of Drug Design and Drug Action", Academic Press, San Diego) and can be employed in compounds useful in the present invention.

II. Pharmaceutical Compositions

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject deprenyl compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The stability of deprenyl can be affected by the pH of the medium in which the deprenyl is formulated. For example, deprenyl is more stable at a pH in the range of about 3–5 than at a pH of about 7. Therefore, when formulating a deprenyl compound in a pharmaceutical composition, it is preferred that the deprenyl compound be maintained at a suitable pH. In preferred embodiments, a pharmaceutical composition of the invention has a pH in the range of about 3 to about 5, more preferably about 3 to about 4. Furthermore, ethyl alcohol is a preferred solvent for improving stability of deprenyl. Thus, in certain embodiments, alcoholic or aqueous alcoholic media are preferred for the pharmaceutical compositions of the invention.

As set out above, certain embodiments of the present deprenyl compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulfonate salts and the like (see, for example, Berge et al. (1977) "Pharmaceutical Salts", J. Pharm. Sci. 66:1–19).

In other cases, the deprenyl compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the deprenyl compound which produces a therapeutic effect. Generally, out of one hundred per cent, this amount will range from about 0.01 percent to about ninety-nine percent of active ingredient, preferably from about 0.1 percent to about 70 per cent, most preferably from about 1 percent to about 30 per cent.

Methods of preparing these formulations or compositions include the step of bringing into association at least one deprenyl compound of the present invention with the carrier and, optionally, one or more accessory ingredients. In general, the formulations are prepared by uniformly and intimately bringing into association a deprenyl compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A deprenyl compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered deprenyl compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the deprenyl compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active deprenyl compound, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more deprenyl compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the deprenyl compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a deprenyl compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to a deprenyl compound of this invention, these substances. Sprays can additionally contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the deprenyl compound in the proper medium. Absorption enhancers can also be used to increase the flux of the deprenyl compound across the skin. The rate of such flux can be controlled by either providing a rate controlling membrane or dispersing the deprenyl compound in a polymer matrix or gel. Devices, including patches, which transdermally deliver a deprenyl compound by iontophoresis or other electrically-assisted methods can also be employed in the present invention, including, for example, the devices described in U.S. Pat. Nos. 4,708,716 and 5,372,579.

Ophthalmic formulations, eye ointments, powders, solutions, drops, sprays and the like, are also contemplated as being within the scope of this invention.

Pharmaceutical compositions of this invention suitable for parenteral administration comprise one or more deprenyl compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject deprenyl compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc.; administration by injection, infusion or inhalation; topical by lotion or ointment; and rectal by suppositories. Injection (subcutaneous or intraperitoneal) or topical ophthalmic administration are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular deprenyl compound of the present invention employed, or the ester, salt or amide thereof, the route of administration, the time of administration, the rate of excretion of the particular compound being employed, the duration of the treatment, other drugs, compounds and/or materials used in combination with the particular deprenyl compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a deprenyl compound of the invention will be that amount of the compound which is the lowest dose effective to produce a therapeutic effect. Such an effective dose will generally depend upon the factors described above. Generally, intraperitoneal and subcutaneous doses of the compounds of this invention for a patient, when used for the indicated nerve-cell rescuing effects, will range from about 0.0001 to about 10 mg per kilogram of body weight per day, more preferably from about 0.001 mg/kg to about 1 mg/kg per day.

If desired, the effective daily dose of a deprenyl compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition). It will be understood that two or more deprenyl compounds can be administered in a single therapeutic composition.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4.,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

It is believed that certain deprenyl compounds can be at least partially metabolized in vivo after administration to a subject. For example, (−)-deprenyl can be metabolized by the liver to (−)-desmethyldeprenyl, as well as (−)-methamphetamine and (−)-amphetamine, after oral administration. The hepatic metabolism of (−)-deprenyl can be inhibited by administration of a $P_{450}$ inhibitor such as Proadifen. In animal and cell-culture studies, administration of Proadifen reduces the ability of (−)-deprenyl to prevent cell death, but does not block the cell-rescuing activity of (−)-desmethyldeprenyl. Thus, it is believed that at least one metabolite of (−)-deprenyl, most likely (−)-desmethyldeprenyl, is an active compound. It is presently believed that (−)-methamphetamine and (−)-amphetamine are inhibitors of the cell-rescuing activity of deprenyl compounds. It is also believed that monoamine oxidase (MAO, including both MAO-A and MAO-B) inhibitory activity is not required for nerve-cell rescuing activity. Absence of MAO inhibitor activity may in fact provide a drug with fewer side effects. Thus, in certain embodiments, it is preferred that the deprenyl compound have low MAO inhibitor activity, or be administered so as to minimize MAO inhibition (e.g., by use of a suitable prodrug or formulation).

In view of the foregoing, it is preferable to administer deprenyl compounds by a route that minimizes metabolism to inhibitor compounds such as (−)-methamphetamine and (−)-amphetamine, while allowing metabolism to active compounds such as (−)-desmethyldeprenyl. Metabolism to an active compound can occur at the desired site of activity, e.g., in the target organ or area, e.g., the brain. Thus, prodrugs, which are metabolized to active compounds, are useful in the methods of the invention.

It has been found that certain deprenyl compounds have greater therapeutic efficacy (e.g., are effective at lower doses) when administered so as to decrease or prevent the "first-pass" effect. Accordingly, intraperitoneal or especially subcutaneous injection are preferred routes of administration. In preferred embodiments, a deprenyl compound is administered in divided doses. For example, a deprenyl compound can be administered by frequent (e.g., pulsed) injections, or by a controlled infusion, which can be constant or programmably varied as described above. In preferred embodiments in which a deprenyl compound is administered orally, the deprenyl compound can be formulated to reduce the amount of hepatic metabolism after oral administration and thereby improve the therapeutic efficacy.

In certain embodiments, the deprenyl compounds of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); gp120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In a preferred embodiment, the therapeutic compounds of the invention are formulated in liposomes; in a more preferred embodiment, the liposomes include a targeting moiety.

The invention is further illustrated by the following study, which should in no way be construed as being further limiting. The contents of all references, pending patent applications and published patent applications, cited throughout this application are hereby incorporated by reference. It should be understood that the animal models for nerve cell rescue used in the study are accepted and that a demonstration of efficacy in these models is predictive of efficacy in humans.

1.0 Introduction 1.1 Overview

Glial and neuronal numbers in the mammalian central nervous system (CNS) are determined as a result of the progression of cells through a series of temporal stages including induction, proliferation, migration, differentiation, degeneration and death. Cell degeneration and death are critical processes, which ultimately serve to counterbalance proliferation and decide the total numbers of cells in any specific region of the CNS. It is thought that cell degeneration and death mechanisms occur in order to eliminate functionally inappropriate, damaged or abnormal cells that could impair or interfere with the operation of a particular neural structure. For more than forty years, cell death has been recognized to be central to nervous system development (Glucksmann, 1951; Saunders, 1966). During development, cells are generated in excess and functionally inappropriate cells degenerate and are eliminated during so called critical developmental periods.

Inadequate survival signals have been suggested to be one of the predominant initiating events for the mechanisms of developmental cell death in the CNS (Raff, 1992). The exchange of trophic signals between cells is now known to be a major factor in the determination of which cells survive and which cells degenerate and die during development. An understanding of trophic signaling in nervous system development now appears to be relevant to the pathogenesis of some glial and neuronal degenerative diseases (Tatton et al., 1997).

Cell death is now recognized to proceed by three different processes, apoptosis, necrosis and atrophy (Ellis et al., 1991). The study of Kerr et al. (1972) was one of the first to differentiate apoptosis from necrosis on the basis of differences in cytology. Cell swelling and breakdown of the external membranes of the cell were known to be typical features of necrosis. Using electron microscopy, Kerr and his colleagues described nuclear degradation, particularly chromatin condensation, in cells that retained intact cell membranes. Because the cells underwent shrinkage rather than swelling, they termed the process 'shrinkage necrosis'. Shrinkage necrosis was subsequently termed apoptosis. Subsequently, Kerr's colleague, Wyllie and his associates, recognized that endonuclease-mediated nuclear DNA cleavage is a principal identifying feature of nuclear degradation in apoptosis (Arends et al., 1990). The third cell death process, atrophy, involves the gradual shrinkage and progressive dysfunction of cells that has been found to accompany nervous system aging (Finch, 1993). Apoptosis can occur over hours or days while necrosis occurs within minutes to hours of insult presentation. Atrophy on the other hand is protracted and occurs over months or years.

Naturally occurring apoptosis is difficult to study since apoptotic nuclei are short-lived and the cells enter apoptosis in highly desynchronized manner. Only a small proportion of cells are in the apoptotic process at any time point so that biochemical or molecular methods are faced with the difficulty of detecting changes that accrue from only a few apoptotic cells mixed with large numbers of normal cells.

Accordingly, models in which cells enter apoptosis in a highly synchronized manner have been extremely valuable in studying the mechanisms underlying the apoptotic process. Models in which trophic support is suddenly withdrawn from cultured cells have proven to be particularly valuable. Furthermore, the study of apoptotic mechanisms has largely been facilitated by the development of light microscopic techniques that detect nuclear DNA cleavage and/or chromatin condensation in situ (see (Tatton et al., 1997)). The in situ methods allow the relatively small proportion of apoptotic cells to be directly examined while using their unaffected neighbors as controls (see (Wadia et al., 1998)).

Most studies of nervous system apoptosis have focused on nerve cells. Relatively little attention has been paid to glial cell apoptosis. Glia, derived from the Greek word for glue, were initially thought of as cells which simply provide a framework to hold neuronal cells together. It is now known that glia subserve a number of roles in nervous system operation and that those roles are considerably more critical than just holding the neurons together (Travis, 1994).

One of those roles involves the facilitation of action potential transmission by the myelination of nerve cell axons. In the mammalian central nervous system, myelination is carried out by oligodendrocytes that synthesize myelin, a lipid rich biological membrane, which forms into multilamellar sheaths. Astrocytes are involved in a number of functions, most notably as guides for neuronal migration, process outgrowth and the synthesis and provision of a number of neurotrophic factors. Microglia, the third glial cell type, are bone marrow derived macrophages which function as immunocompetent cells in the CNS.

1.2 Oligodendrocyte Differentiation

Oligodendrocytes are generated postnatally from undifferentiated pleuripotential cells. Two major alternate cell types are generated from these pleuripotent cells: oligodendrocytes and type-2 astrocytes. Cells expressing the antigenic phenotype of oligodendrocytes are first detected around the time of birth in rats while the first appearance of type-2 astrocytes occurs at 7–10 days after birth (Abney et al., 1981; Miller et al., 1985). In the rat CNS, three main oligodendroglial cell lineage have been identified. They are the undifferentiated oligodendrocyte-type 2 astrocyte (O-2A) progenitor cells, the partially differentiated proligodendrocytes (PROLs) and the fully differentiated oligodendrocytes (OLs).

Most of the information on oligodendrocyte ontogeny has been obtained from in vitro studies using dissociated cultures from neonatal rat or mouse cortex or rat optic nerve (Gard and Pfeiffer, 1989; Norton and Farooq, 1993). Primary cultures of oligodendroglial cells provide a powerful model system to study the regulation of differentiation, function and death. Cultured oligodendrocytes mimic their in vivo counterparts in that they synthesize myelin specific proteins and also produce myelin-like membranes (Knapp et al., 1987; Szuchet et al., 1986). Oligodendrocytes in vitro can be maintained in chemically-defined media containing low serum which allows for the study of the actions of specific molecules on the cells.

1.2.1 Oligodendrocyte-type 2 Astrocyte (O-2A) Progenitors

The characterization of the O-2A lineage cells in the last decade has facilitated an understanding of glial cell development. Several studies have shown that O-2A progenitor cells are bipotential and can undergo differentiation along two lines into either oligodendrocytes or type-2 astrocytes. The O-2A cells display a high degree of developmental plasticity and their differentiation can be manipulated by placement into a defined in vitro environment (Saneto and de Vellis, 1985). Extracellular signaling molecules like serum and trophic factors and cell-intrinsic factors regulate the sequential differentiation of the O-2A progenitor cells. Culture of O-2A progenitors in low serum conditions causes them to differentiate into oligodendrocytes. Higher concentrations (10% or more) of fetal calf serum induce their differentiation into a type-2, process bearing astrocytes (Raff et al., 1983; Temple and Raff, 1985).

Developmental studies have shown that O-2A progenitor cells originate in the subventricular zone of the forebrain, the subependymal layers of the 4th ventricle and in the ventral spinal cord (Curtis et al., 1988; LeVine and Goldman, 1988; Pringle and Richardson, 1993; Reynolds and Wilkin, 1988; Warf et al., 1991). Prior to migrating from those sites, the cells proliferate. In the rat brain, an initial population of O-2A progenitors of about $5 \times 10^5$ cells generates about $60 \times 10^6$ oligodendrocytes. O-2A progenitor cells are highly motile and migrate from the germinal zones of origin into widespread regions of the developing CNS including the subcortical white matter, cerebellum, spinal cord and the optic nerve (Small et al., 1987; Warf et al., 1991). After migrating to their final destinations, the O-2A cells differentiate into PROLs and OLs capable of initiating myelination.

1.2.2 Maturation of O-2A Progenitors

The bipolar O-2A progenitor cells differentiate into intermediate, multipolar PROLs (Gard and Pfeiffer, 1990). The PROLs further differentiate into complex, multipolar OLs (Gard and Pfeiffer, 1989; Raff, 1989).

Initially, the cells of the O-2A lineage were characterized only on the basis of their morphologies. Later studies showed that different cells in the oligodendrocyte lineage express specific developmental marker proteins (Raff et al., 1979; Reynolds and Wilkin, 1988). The bipolar O-2A progenitor cell can be recognized by antibodies against a three surface tetragangliosides, A2B5, LB1 and GD3 (Levi et al., 1987; Raff et al., 1983; Reynolds and Wilkin, 1988). The O-2A progenitor cells do not express the astrocyte specific intermediate filament protein, glial fibrillary acidic protein (GFAP). PROLs begin to express surface galactosphingolipids like galactocerebroside (GC) (Raff et al., 1979) and cyclic nucleotide phosphorylase-I (CNPase-I) but do not express A2B5, LB1 or GD3 (Mirsky et al., 1980. OLs are immunopositive for GC and CNPase-I but also express reactivity to myelin basic protein (MBP) and proteolipid protein (PLP) (Dubois Dalcq, 1987; Zeller et al., 1985). As well as MBP and PLP, OLs express a number of other myelin related proteins including myelin oligodendrocyte glycoprotein (MOG) and myelin associated glycoprotein (MAG) (Dubois Dalcq et al., 1986). MBP forms 30 to 40% of CNS myelin protein while PLP forms 50% of the protein mass of myelin. MBP and PLP are present in the complex processes of mature OLs.

In order to study apoptosis in the oligodendrocytic and type-2 astrocytic lineage, I developed pure cultures enriched in O-2A progenitor cells using a modified differential shake-off procedure (McCarthy, 1980). The O-2A progenitor cells were differentiated in the presence of insulin and IGF-I. Individual cell types in the lineage were identified by combining immunocytochemistry for antibodies against cell specific marker proteins with morphologic identification criteria. The approach allowed comparisons of apoptotic events and the effects of anti-apoptotic agents in the different cell types.

1.23 Trophic Factor Regulation of Oligodendrocyte Differentiation

The differentiation of O-2A progenitor cells into OLs is influenced by a number of polypeptide trophic factors including platelet derived growth factor (PDGF), basic fibroblast growth factor (bFGF), ciliary neurotrophic factor (CNTF), insulin and insulin-like growth factor-I (IGF-I) (Barres and Raff, 1994). In vivo, the trophic factors can be synthesized by either neurons or astrocytes or both. CNTF induces the differentiation of O-2A cells into type-2 astrocytes while PDGF induces O-2A cell differentiation into OLs (Lillien and Raff, 1990). In the presence of PDGF, the O-2A progenitor cells generally undergo about 8 divisions before synchronously differentiating into OLs (Noble et al., 1988; Raff et al., 1988; Richardson et al., 1988). Factors like bFGF are mitogenic for the O-2A progenitor cells and keep the O-2A cells in the mitotic cycle thereby preventing their differentiation into OLs. In contrast, insulin and IGF-I have been shown to induce irreversible OL differentiation (McMorris and Dubois Dalcq, 1988; Raff et al., 1983).

1.3 Oligodendroglial Death 1.3.1 Developmental Death of O-2A Lineage Cells

Glial cells, particularly O-2A cells, are over produced during nervous system development. In vivo developmental studies have revealed that more than 50% of the newly formed O-2A progenitor cells undergo apoptosis (Barres et al., 1992). The O-2A apoptosis has been seen to occur prior to differentiation and myelination of neuronal axons. The massive O-2A cell death has been hypothesized to occur in order to limit OL numbers at levels that are appropriate to the axon surface areas requiring myelination.

Cell death is not limited to the O-2A progenitor cell populations but also is seen the OLs. Recent studies have indicated that premyelinating OLs that go on to differentiate into myelinating OLs undergo cell death (Trapp et al., 1997). Although the developmental cell death of OLs is now well recognized, it has not been determined whether or not it is apoptotic. If it is apoptotic, it is not known whether the process involves mitochondrial decisional points (see below) or whether it is responsive to anti-apoptotic compounds like (-)-deprenyl.

1.3.2 Oligodendrocyte Death in Pathological Conditions

OL death occurs not only during development but also in some pathological conditions. In human demyelinating diseases, like multiple sclerosis (MS), neurological manifestations depend on the axon populations that are involved by the demyelinating lesions and the functional deficits that result from impaired conduction in those axons. Neuropathological examination of the demyelinating MS foci has revealed a pronounced decrease in OL numbers, suggesting that the process involves OL death (Bruck et al., 1994). Loss of OLs has been observed in both acute and chronic MS lesions.

The pathogenesis of MS has not been fully explained. The disease has been thought to result from a number of causes principally aberrant autoimmunity directed against myelin antigens, possibly triggered by ubiquitous ribonucleic acid or deoxyribonucleic acid viruses (Scolding et al., 1994; Simon and Neubert, 1996; Tienari, 1994). An inflammatory response accompanies the breakdown of myelin and the response is thought to be initiated by perivascular infiltration of CD4+ T lymphocytes (Raine, 1994). It is believed that the activated T lymphocytes produce cytokines like lymphotoxin and tumor necrosis factor (TNF) which consequently act as major mediators of OL injury (Selmaj et al., 1991; Selmaj and Raine, 1988). According to the view that an immune attack causes myelin damage and the consequences of the myelin damage result in OL damage, the decreased OL numbers in MS foci would be the result of OL death secondary to demyelination. Alternately though, immune or other damage to OLs could cause OL apoptosis with a resulting demyelination so that the decrease in OL numbers would be the primary rather than the secondary event in MS.

The decreased numbers of OLs in MS foci could also result from damage to the oligodendrocyte progenitor cells. Damage to O-2A progenitor cells could result from demyelinating periventricular lesions which are found in about 90% of MS brains (Lumsden, 1971). Periventricular lesions result in damage to the O-2A progenitor cells concentrated in the subependymal layer. The damaged oligodendrocyte progenitor cells would be unavailable to migrate from the subependymal layer and to replace OLs lost in the MS foci.

1.3.3 Oligodendrocytes and OL Progenitors Require Trophic Factors For Survival

Trophic factors have been considered above relative to their roles in influencing OL and type-2 astrocyte lineage differentiation. They also may play an important role in determining the survival of cells in the two lineages. There has been great interest in the role of trophic factors in the prevention of the death of neuronal cells (Thoenen, 1991). For example, trophic factors like CNTF, have been shown to ameliorate cell death of motoneurons in vivo when applied directly to the cells (Sendtner et al., 1992) or into the cerebrospinal fluid (Zhang et al., 1995). Other trophic factors, like nerve growth factor (NGF) prevents the death of several neuronal types like the sympathetic neurons and basal forebrain cholinergic neurons (Hefti, 1986; Oppenheim et al., 1982).

Insulin, IGF-I, CNTF, PDGF and neurotrophins have been shown to increase the survival of OLs (Barres et al., 1992; Barres et al., 1992; Liu et al., 1993; Louis et al., 1993). The factors have also been shown to protect OLs from injury mediated by cytokines like TNF (D'Souza et al., 1996). Studies in the rat optic nerve have suggested that axonal activity modulates the release of the trophic factors (Barres et al., 1993). Both in vivo and in vitro, astrocytes and neurons are considered to be the chief source of the growth and survival factors (see (Henderson et al., 1994; Seniuk-Tatton et al., 1995) for evidence that both neurons and astrocytes synthesize CNTF).

1.3.4 Effects of Insulin, IGF-I and PDGF on Oligodendrocyte Survival

The importance of IGF-I in the survival of differentiated oligodendrocytes was suggested by the observation of hypermyelination in transgenic mice overexpressing IGF-I (Carson et al., 1993). Other studies reported decreased numbers of oligodendrocytes in mice carrying homozygous disruptions of the IGF-I receptor (Liu et al., 1993). Evidence for IGF-I regulation of normal myelination has also been obtained from nutritional studies (Wiggins, 1982). Those studies observed that nutritional deficiency during the postnatal developmental period in rats or mice resulted in decreased IGF-I levels and that the lowered IGF-I levels were associated with severe hypomyelination.

Studies using neuronal cell lines or primary cultures of neurons or OLs have indicated that not only IGFs' but also insulin regulates cell survival. Several in vitro studies have shown that high concentrations of about 10 $\mu$g/ml of insulin is essential for the survival of neuronal cells in serum free medium (Bottenstein, 1986; Eccleston and Silberberg, 1984; Saneto and de Vellis, 1985). The observation that physiological concentrations of insulin enhanced the numbers of OLs in vitro suggested that insulin acted as an analogue of IGF-I by acting through the IGF-I receptors (McMorris, 1983; McMorris et al., 1990).

Insulin and IGF-I appear to act cooperatively to regulate cell survival and death. Not much is known with respect to the role of insulin and IGF-I in regulating oligodendroglial survival, particularly whether their withdrawal leads to OL apoptosis. The present study established a culture model in order to investigate the capacity of insulin and IGF-I withdrawal to initiate OL and type-2 astrocyte lineage apoptosis.

Other studies have utilized in vitro systems to examine the effects of trophic factors on the survival of oligodendroglial cells. Using immunopanning techniques in vitro, (Barres et al., 1992) examined the survival of O-2A progenitor cells. Their study found that in the absence of serum or growth factors, the O-2A progenitor cells underwent rapid death according to a process, which included features suggestive of apoptosis. PDGF appeared to increase the O-2A progenitor cell survival. Barres and her colleagues performed experiments on O-2A progenitor cell survival in the intact mouse optic nerve. On transplantation of Cos-7 cells engineered to secrete PDGF in the subarachnoid space of the mouse brain, it was observed that in the intact mouse optic nerve, PDGF decreased O-2A cell death by about 85%. Furthermore, the numbers of surviving O-2A progenitor cells in the mouse optic nerve were seen to double over a period of four days.

Several studies have reported that the survival enhancing action of PDGF is specific to O-2A cells and not to OL cell populations (Hart et al., 1989; McKinnon et al., 1990). It is believed that lack of expression of PDGF receptors on differentiated oligodendroglial cells prevents PDGF from enhancing their survival. Therefore, these studies suggest that the survival of OLs is dependent on the presence of trophic factors other than PDGF, like insulin and IGF-I, yet prior to the experiments described in this thesis, there were no studies of the prevention of OL apoptosis by insulin and IGF-I.

1.4 Apoptotic Cell Death

Our understanding of apoptosis has advanced rapidly over the last several years. Nervous system apoptosis was thought to only result from trophic insufficiency. It is now known that apoptosis can be initiated in neural cells by many different forms of damage and proceeds in a step by step fashion with each step involving signaling by specific proteins. The signaling involves the cleavage, binding, phosporylation or inter-organelle movements of proteins. The signaling pathways in the early phases of apoptosis depend on the form of damage that initiates the process. Accordingly, specific early pathways can be identified by changes in the levels and/or subcellular locations of specific proteins. The early signaling pathways converge onto a small number of effector signaling pathways that lead to the final degradative steps typical of apoptosis (see (Susin et al., 1996)).

In comparison to necrosis, apoptosis is a private kind of process. In necrosis, cells swell and their plasma membrane fracture allowing their intracellular contents to induce an inflammatory reaction. Inflammatory cytokines and other factors then damage and kill other nearby cells that were not involved in the primary process with the result that by the formation of membrane wrapped fragments that do not induce an inflammatory reaction. The expression of surface markers on the wrapped fragments causes them to be engulfed by macrophages without damage to nearby cells. Accordingly, individual cells can die by apoptosis without any involvement of their neighbors.

The individuality of apoptosis allows for the process to select specific cells for development without altering the overall organization of a neural structure (see (Raff, 1992)). It also allows apoptosis to serve as a selective defense system that can remove cells which are tumorigenic or infected by viruses (Vaux et al., 1994) without compromising the function of a nervous system structure.

Nervous system apoptosis is not limited to development as it also occurs in pathological conditions (Chalmers-Redman et al., 1996). As well as the evidence for apoptosis in MS presented above, it is now thought to contribute to neurodegenerative diseases including Parkinson's disease (Olanow and Tatton, 1999), Alzheimer's disease (Anderson et al., 1996; Su et al., 1997), amyotrophic lateral sclerosis (Yoshiyama et al., 1994), Huntington's disease (Thomas et al., 1995) as well as acquired immunodeficiency syndrome (AIDS) (Petito and Roberts, 1995). Participation of apoptosis in those conditions was largely missed on standard neuropathological examination due to the absence of inflammation and the selective culling of scattered cells.

1.4.1 The Differentiation of Apoptosis and Necrosis

The occurrence of differences in the ultrastructure of cells dying by apoptosis or necrosis was first observed by Kerr who recognized a subpopulation of cells in the ischemic liver that were shrunken and retained intact lysosomal structure (Kerr, 1965). In ischemic liver that were shrunken and retained intact lysosomal structure (Kerr, 1965). In contrast, necrotic hepatic cells were swollen with dissolution of lysosomes. Electron microscopy revealed that the shrunken cells had undergone cytoplasmic condensation and budding into membrane bound cell fragments, which were engulfed by phagocytes. Importantly, organelle structure was maintained within the cell fragments (Kerr, 1971).

In 1972, Kerr, Wyllie and Currie (Kerr et al., 1972) detailed the ultrastructural features of the shrunken cells and termed the process as "apoptosis". They reported that the nuclei showed chromatin condensation and segregation into sharply delineated masses. They termed the condensed and fragmented cytoplasm that was membrane-wrapped as apoptotic bodies. The picture of apoptosis is slightly different in vitro where, in the absence of macrophages, apoptotic bodies persist for a longer period of time and may undergo cytolysis or secondary necrosis.

In 1980, Wyllie reported that the activation of endonucleases in apoptosis resulted in nuclear DNA fragmentation (Wyllie, 1980). Gel electrophoresis showed a 180–200 bp "ladder" pattern of DNA degradation indicative of internucleosomal DNA cleavage. DNA fragments of 300 or 500 bp in length are also formed in apoptosis and can be better detected with pulse field techniques (Sestili et al., 1996). In contrast, in necrosis DNA cleavage is random producing a diffuse smear on DNA electrophoresis.

However, large amounts of tissue are required to detect DNA cleavage with these techniques, so they are not suitable for detecting small numbers of apoptotic nuclei and in a tissue with a number of different cell types, they do not allow the investigator to determine which types are apoptotic and which types are not. Nuclear DNA cleavage can be detected in situ using end labeling (ISEL) techniques, which attach a chromagen or fluorochrome to the 3' cut ends of DNA (Migheli et al., 1994; Tatton and Kish, 1997). Chromatin condensation, which accompanies DNA fragmentation, can also be detected in situ staining with fluorescent DNA binding dyes such as acridine orange, Hoechst 33258 or YOYO-1 (Darzynkiewicz et al., 1992; Tatton and Kish, 1997). Apoptosis can be unambiguously demonstrated if DNA ladder, ISEL positive nuclei and nuclear chromatin condensation are jointly demonstrated for the same cells.

1.4.2 Nerve Cell Apoptosis

It is now known that the massive death of neurons that occurs during mammalian prenatal and postnatal brain development depends on competition for trophic factors and represents a form of apoptosis (Martin et al., 1992; Raff et al., 1993). Nerve cells obtain their trophic support from their targets, which can supply limited amounts of trophic molecules. Limited supply of trophic molecules leads to a competition among the developing neurons so that neurons that are best connected survive while weakly connected neurons die (Oppenheim, 1991). The trophic insufficiency dependent death of developing neurons was termed "programmed cell death" since it depended on activation of a program of gene expression that led to the synthesis of "death proteins" (Oppenheim et al., 1990).

A requirement for new protein synthesis can be a hallmark of programmed neuronal death or apoptosis, although it is not necessary for all forms of neuronal apoptosis (Dragunow and Preston, 1995; Johnson et al., 1995). In some forms of neuronal apoptosis, proteins that are necessary for apoptosis to occur are constitutively expressed, while they must be newly synthesized in others (Eastman, 1993). The characteristic morphologic findings of apoptosis persist in many models of nerve cell apoptosis, even when transcriptional and translational blockers are used to inhibit new protein synthesis. For example, transcriptional or translational blockers that greatly reduce new protein synthesis do not prevent apoptosis after serum withdrawal in PC 12 cells that have been exposed to serum but not to NGF (Rukenstein et al., 1991). Similarly, PC12 cells that have been exposed to NGF for 6 days and have initiated process growth, undergo apoptosis after serum and NGF withdrawal that is independent of new protein synthesis (Tatton et al., 1994). In contrast, apoptosis in neuronally-differentiated PC12 cells caused by trophic withdrawal after 9–12 days of NGF exposure requires new protein synthesis (Mesner et al., 1992). Therefore, apoptosis can be dependent on new protein synthesis and be termed programmed cell death, or can be independent of new protein synthesis and be unprogrammed. Dependence on new protein synthesis can be used as a marker for neuronal apoptosis (Sanchez et al., 1997; Ueda et al., 1996) but absence of new protein synthesis does not rule out apoptosis (Deshpande et al., 1992).

1.4.3 Changes In Gene Expression and Protein Levels in Apoptosis

In recent years, a number of genes and their protein products have been found to mediate the progression of apoptosis. Such genes and protein products can serve as markers of apoptotic cell death process. Included among mediators of apoptosis are oncoproteins, oncogenes, and several protease families. The BCL-2 homolog family of oncoproteins includes both inhibitors and promoters of apoptosis (Hockenbery, 1992; Merry and Korsmeyer, 1997). Inhibitors of apoptosis include BCL-2 itself, BCL-X (BCL-$X_L$, BCL-X$\alpha$, and BCL-X$\beta$), MCL-1, and A1, while BAX, BCL-$X_S$, BAD, BAK, and BIK promote apoptosis. Some of the BCL-2 family members like BCL-2 and BAX can also interact with each other by forming homo- or heterodimers. Most of the oncoproteins are found localized to the outer mitochondrial and nuclear membranes. In normal hemopoetic cells, BCL-2 is concentrated in the outer mitochondrial membrane, while BAX is largely confined to the cytosol however during apoptosis BAX becomes concentrated in mitochondrial membranes (Hsu et al., 1997). Furthermore, in the early stages of apoptosis, a number of cytoplasmic proteins undergo nuclear translocation.

A number of proteases, including cysteine proteases, calpains, and proteasomes have been shown to be involved in the apoptotic cell death process. Most recent research efforts have been focused on the interleukin converting enzyme (ICE)-like proteases which are termed caspases (Cohen, 1997; Nath et al., 1996). To date, 10 different caspases have been identified with caspase-3 receiving most attention (Krajewska et al., 1997). The caspases are synthesized as inactive precursors and are activated in models of neuronal apoptosis (Armstrong et al., 1997; Du et al., 1997). Other proteases like calpains have been shown to contribute to the cleavage of the cytoskeletal protein actin during apoptosis (Brown et al., 1997). Calpain inhibitors have been shown to block actin cleavage in apoptosis (Gressner et al., 1997).

Cell-cycle related proteins and cycle kinases including cyclin D1, cyclin B, cyclin E, and Cdc2 kinase show increased levels during neuronal apoptosis (Freeman et al., 1994; Gao and Zelenka, 1995; Haupt et al., 1996; Kranenburg et al., 1996). Appearance of the cycle-related proteins is thought to represent an abortive attempt of the post mitotic neuronal cells to return to the cell cycle (Shirvan et al., 1997).

Another protein involved in the cell cycle as a mitosis inhibitor, p53, increases in a number of forms of neuronal apoptosis (Jordan et al., 1997; Polyak et al., 1997) and has been shown to increase the levels of the oncoprotein BAX in non-neuronal forms of apoptosis (Xiang et al., 1998). It is now understood that apoptosis can be separated into p53 dependent and p53 independent forms (see (Bellamy, 1997) for a detailed review of the role of p53 in apoptosis). Recently, a large number of p53-induced genes (PIGs) have been identified, which are proposed to mediate apoptosis by increasing oxidative radical levels, thereby inducing mitochondrial damage (Polyak et al., 1997). p53-induced apoptosis can proceed after treatment with translational or transcriptional blockers (Kharlamov et al., 1997), indicating that p53 can induce apoptosis through pathways that do not require new protein synthesis.

A signal-transducing transcription factor of the AP-1 family, c-jun, is normally involved in cell cycle control and differentiation. A variety of evidence indicates that c-JUN is involved in a number of in vitro and in vivo models of neuronal apoptosis (BossyWetzel et al., 1997). Apoptosis is also induced by the Fas antigen and its mRNA has been shown to increase in ischemic nerve and glial cells (Depraetere and Golstein, 1997; Matsuyama et al., 1995). Another marker for apoptosis is tissue transglutaminase, which cross-links cytoplasmic proteins and is increased in apoptotic cells (Fesus et al., 1991). Transglutaminase activity leads to the formation of high molecular mass protein polymers, which maintain the integrity of apoptotic cells and bodies and prevents leakage of their contents into the extracellular space.

Lastly, overexpression of the gene for the radical scavenger protein, Cu/Zn superoxide dismutase (SOD-1), reduces neuronal apoptosis (Greenlund et al., 1995; Przedborski et al., 1992) while underexpression increases apoptosis (Troy and Shelanski, 1994). Point mutations in the gene that encodes SOD-1 has been shown to convert the anti-apoptotic action of SOD-1 to a pro-apoptotic one (Rabizadeh et al., 1995).

1.4.4 The Role of Mitochondria in Apoptosis

Mitochondria are now believed to play a critical role in signaling for the initiation of some forms of apoptosis. Apoptosis was initially believed to occur independently of mitochondrial factors (Jacobson et al., 1993; Korsmeyer et al., 1993). The importance of mitochondria in the initiation of apoptosis is illustrated by the finding that mitochondrial factors can induce chromatin condensation and nuclear fragmentation typical of apoptosis in cell free Xenopus egg extracts (Newmeyer et al., 1994). Current evidence now indicates that apoptosis is associated with a sequence of events that includes a fall in mitochondrial membrane potential ($\Delta\psi_M$), opening of a mitochondrial megapore known as the permeability transition pore (PTP), and release into the cytoplasm of small mitochondrial proteins which signal the initiation of apoptosis known as apoptosis initiating factors (AIF).

1.4.5 Mitochondrial Membrane Potential And Apoptosis

Studies of $\Delta\psi_M$ have been pivotal in understanding the relationship between mitochondria and the initiation of apoptosis. An electrochemical proton gradient normally exists across the inner mitochondrial membrane resulting in a $\Delta\psi_M$ of approximately-150 millivolts and a proton concentration difference ($\Delta$pH) across the mitochondrial membrane. The $\Delta\psi_M$ is dependent on the capacity of mitochondrial complexes I, III, and IV to use electron energy in the carrier molecules nicotinamide adenine dinucleotide (NADH), ubiquinone, and cytochrome C (CytC) to pump protons out of the mitochondrial matrix by transporting them across the inner mitochondrial membrane. Complex II transfers energy from $FADH_2$ to ubiquinone, but does not pump protons. The outward pumping of protons produces an electron gradient that is biochemically reflected by a pH difference ($\Delta$pH) and electrically by a voltage across the inner mitochondrial membrane also known as $\Delta\psi_M$ (Sheratt, 1991). The $\Delta\psi_M$ and the $\Delta$pH contribute to a proton electromotive force ($\delta$p) ($\delta p=\Delta\psi-60\ \Delta pH$, where $\Delta pH$= mitochondrial pH-cytosol pH). $\delta$p drives the conversion of ADP to ATP at complex V (ATP synthase). Since $\Delta\psi_M$ is by far the greater contributor to $\delta$p, $\Delta\psi_M$ can be assumed to vary almost linearly with the ATP/ADP ratio and to provide an estimate of the ATP/ADP ratio within individual mitochondria.

Measurements of whole cell potentiometric dye fluorescence in a variety of blood, hepatic, and immune cell models have shown that $\Delta\psi_M$ is reduced very early in the apoptotic process, prior to the onset of nuclear DNA fragmentation and chromatin condensation (Susin et al., 1996). More recently, Tatton and coworkers used laser confocal imaging to obtain direct measurements of $\Delta\psi_M$ in living NGF-differentiated PC 12 cells and showed that a decrease in $\Delta\psi_M$ is also one of the earliest, if not the earliest, detectable event in apoptosis induced by NGF and serum withdrawal (Wadia et al., 1998). $\Delta\psi_M$ was significantly reduced in a proportion of mitochondria three to six hours prior to nuclear DNA fragmentation and chromatin condensation. The decrease in $\Delta\psi_M$ was temporally correlated with an increase in intramitochondrial $Ca^{2+}$ but not with an increase in cytosolic oxidative radical levels, which increased only after the decrease in $\Delta\psi_M$ was well established. Decreases in $\Delta\psi_M$ coupled with increases in intramitochondrial $Ca^{2+}$ induce opening of the PTP (see below (Scorrano et al., 1997). Accordingly, these changes found in early apoptosis were appropriate to open the PTP.

1.4.6 The Permeability Transition Pore

A decrease in $\Delta\psi_M$, in the presence of increased intramitochondrial $Ca^{2+}$ (Scorrano et al., 1997), induces opening of a PTP, which spans the inner and outer mitochondrial membranes. The PTP consists of an adenine nucleotide translocator (AdNT) which is a critical element of the PTP but whether it forms the pore itself or is just closely associated with a pore forming protein is unknown. The PTP also includes a voltage dependent anion channel (a porin) and a peripheral benzodiazepine binding protein. The components of the PTP are closely associated with hexokinase, creatine kinase, and BCL-2, as well as other elements, such as glycerol kinase, phospholipid hydroperoxidase, glutathione peroxidase, 3-b-hydroxysteroid dehydrogenase isomerase, and cardiolipin synthase.

The PTP opens in response to a decrease in $\Delta\psi_M$ in the presence of an increase in intramitochondrial $Ca^{2+}$ (Scorrano et al., 1997). Marked increases in mitochondrial $Ca^{2+}$ increased oxidative radical levels, or partial failure of the respiratory complexes, acting either individually or together, can induce a fall in $\Delta\psi_M$ (Richter, 1993). Opening of the PTP dissipates any remaining proton gradient across the mitochondrial membrane and further reduces the $\Delta\psi_M$ (Bernardi et al., 1994). Complete opening of the PTP allows free exchange of solutes and small proteins between the mitochondrial matrix and the extramitochondrial cytosol. Consequently mitochondria swell rupturing the outer mitochondrial membrane. As a result AIFs are released from the intermembrane space of the mitochondria into the cytoplasm (Marchetti et al., 1996; Susin et al., 1996). Mitochondrial AIFs may be released directly through the PTP or through fractures in the mitochondrial membrane.

Several factors are known to influence opening or closure of the PTP. Compounds like cyclosporin A bind to the PTP and maintains it in a closed position. It also promotes pore closure by binding cyclophilins that otherwise induce PTP opening in the presence of $Ca^{2+}$ by binding to the AdNT (Bernardi et al., 1994; Scorrano et al., 1997). Factors like glutathione, ADP levels, and ROS levels in the mitochondrial matrix modulate the gating voltages necessary to induce PTP opening but are not sufficient in themselves to open the PTP (Chernyak and Bernardi, 1996).

Anti-apoptotic proteins like BCL-2 bind to the PTP. BCL-2, binds to the peripheral benzodiazepine binding component of the mitochondrial PTP (Carayon et al., 1996) and maintains closure of the PTP in a manner similar to cyclosporin A. BCL-2 has been shown to localize to the outer mitochondrial membrane (Lithgow et al., 1994; Riparbelli et al., 1995) within or near to, the mitochondrial peripheral benzodiazepine receptor (Carayon et al., 1996). Cytosolic BCL-2, which is truncated and cannot dock in mitochondrial membranes, is considerably less effective in reducing apoptosis than BCL-2 located in mitochondrial membranes (Hockenbery et al., 1993). Richter first proposed that BCL-2 reduces apoptosis by maintaining $\Delta\psi_M$ (Richter, 1993). Zamzami and coworkers subsequently provided persuasive evidence, demonstrating that BCL-2 maintains PTP closure (Zamzami et al., 1996) and blocks the initiation of apoptosis by preventing the escape of heat labile molecules, which signal the onset of apoptosis. Numerous other studies have also shown that BCL-2 can prevent a decrease in $\Delta\psi_M$ and the release of ICE-like AIFs (Marchetti et al., 1996; Susin et al., 1996). Thus, opening of the PTP can be viewed as the critical decisional step in many forms of apoptosis and is proposed to constitute an irreversible step in the process.

1.4.7 Apoptosis Initiating Factors

The importance of mitochondrial factors in the initiation of apoptosis has been demonstrated by studies showing that mitochondrial homogenates are essential for the progression of the nuclear changes of apoptosis in cell free systems (Newmeyer et al., 1994). Several apoptosis promoting mitochondrial AIFs have been identified to date. dATP, when accompanied by holocytochrome C, a nuclearly encoded 14 kDa protein, which is normally localized to the mitochondrial intermembranous space, can promote apoptosis in some cell free systems (Liu et al., 1996). Additionally, in some forms of apoptosis, CytC can be found in the extramitochondrial cytosol in the early stages of apoptosis (Yang et al., 1997) and injection of CytC into cells induces apoptosis (Li et al., 1997). CytC release from mitochondria has been shown to activate a caspase 3 precursor leading to activation of an endonuclease that cleaves nuclear DNA (Kharbanda et al., 1997; Li et al., 1997).

1.4.8 Oxidant Radicals and Mitochondrial Apoptosis

An increase in oxidative radicals derived from the mitochondria is thought to be associated with mitochondrial apoptosis (Richter et al., 1995). Increased levels of oxidative radicals, particularly in the presence of increased intramitochondrial $Ca^{2+}$, can induce apoptosis by causing cross linking of protein thiols in the mitochondrial inner membrane (van de Water et al., 1994) and opening of the PTP (Chernyak and Bernardi, 1996). BCL-2 which has been shown to act as an anti-oxidant is thought to provide anti-apoptotic effects through an indirect effect on the PTP as well as by its direct effect on the PTP (Hockenbery et al., 1993). Tatton and his co-workers have shown that a decrease in BCL-2 levels in trophically-deprived PC12 cells entering mitochondrial apoptosis is associated with markedly increased cytosolic levels of oxidative radicals (Tatton et al., 1996). In contrast, the reduction in apoptosis induced by bcl-2 overexpression is associated with a decrease in both oxidative radical levels and in peroxidation of membrane lipids (Hockenbery et al., 1993). Similar effects have been detected with oxidative radical scavengers, such as SOD-1 and glutathione, which have been shown to prevent the direct action of oxidative radicals on PTP opening (Chernyak and Bernardi, 1996). These direct and indirect actions of oxidative radicals on the PTP may reinforce each other in inducing apoptosis.

1.5 (–)-Deprenyl Can Reduce Apoptosis (–)-Deprenyl is a selective inhibitor of monoamine oxidase B (MAO-B) (Heinonen et al., 1994). Co-administration of (–)-deprenyl or other MAO-B inhibitors with the parkinsonian toxin, 1-methyl-4-phenyl-1,2,3,6-tetrahydropyridine (MPTP) reduced the decreases in striatal dopaminergic indices caused by the toxin alone (Cohen et al., 1984; Heikkila et al., 1984; Langston et al., 1984). The reduction was interpreted to depend on the blockade of the conversion of MPTP to its active radical, $MPP^+$, by MAO-B in astroglia. If MPTP could not be converted to $MPP^+$, then it could not induce necrosis of substantia nigra dopaminergic neurons (SNDns). Necrosis of SNDns results in the loss of their striatal dopaminergic terminal axons and a decrease in stiatal dopaminergic indices. Accordingly, the maintenance of the striatal dopaminergic indices was interpreted as showing that (–)-deprenyl reduced the necrosis of SNDns caused by $MPP^+$.

Subsequently, it was found: 1) that (–)-deprenyl reduced the death of cultured dopaminergic neurons caused by $MPP^+$ (Mytilineou and Cohen, 1985), 2) that (–)-deprenyl reduced the loss of murine SNDns when (–)-deprenyl treatment was delayed until after the conversion of MPTP to $MPP^+$ was completed (Tatton and Greenwood, 1991) or when (–)-deprenyl doses were employed that were insufficient to inhibit MAO-B or MAO-A (Tatton et al., 1993) and 3) that (–)-deprenyl could increase the survival of non-dopaminergic neurons and axotomized motoneurons, independently of MAO inhibition (Ansari et al., 1993; Salo and Tatton, 1992). Those studies established that (–)-deprenyl could increase neuronal survival through a mechanism that did not require the inhibition of MAO-B.

Studies in trophically-withdrawn neuronally differentiated PC12 cells (Tatton et al., 1994), cerebellar granule cells exposed to cytosine arabinoside (Paterson et al., 1998), trophically deprived human melanoma cells (Magyar et al., 1998) and dopaminergic MES23.5 cells exposed to MPP+ (Le et al., 1997) showed that (–)-deprenyl can reduce apoptotic cell death. Since the original reports of MAO-B independent neuronal rescue, more than thirty studies have reported reduced nerve cell death by (–)-deprenyl for a variety of different types of neurons including motoneurons (Ansari et al., 1993; Iwasaki et al., 1996; Ju et al., 1994; Oh et al., 1994; Ravikumar et al., 1998; Salo and Tatton, 1992; Zhang et al., 1995), neuronally differentiated PC12 cells (Tatton et al., 1994), retinal cells (Buys, 1995; Ragaiey et al., 1997), inferior olivary neurons (Todd and Butterworth, 1998), inferior collicular neurons (Todd and Butterworth, 1998), thalamic neurons (Todd and Butterworth, 1998), mesencephalic dopaminergic neurons (Koutsilieri et al., 1996; Koutsilieri et al., 1994; Mytilineou et al., 1997; Wu et al., 1995), cerebellar neurons (Paterson et al., 1998), cortical neurons (Amenta et al., 1994), striatal neurons (Vizuete et al., 1993) and hippocampal neurons (Amenta et al., 1994; Knollema et al., 1995; Lahtinen et al., 1997; Paterson et al., 1997; Semkova et al., 1996; Zeng et al., 1995; Zhang et al., 1996). Increased neuronal survival has been found after a wide variety of different insults including trophic withdrawal (Tatton et al., 1994), $MPP^+$ exposure (Koutsilieri et al., 1996; Koutsilieri et al., 1994; Schmidt et al., 1997; Wu et al., 1995), excitotoxicity (Abakumova et al., 1998; Kiran et al., 1998; Mytilineou et al., 1997; Semkova et al., 1996), ischemia or hypoxia (Knollema et al., 1995; Lahtinen et al., 1997; Paterson et al., 1997; Ravikumar et al., 1998), DNA toxins (Paterson et al., 1998), axotomy (Ansari et al., 1993; Buys, 1995; Ju et al., 1994; Oh et al., 1994; Salo and Tatton, 1992; Zhang et al., 1995), thiamine deficiency (Todd and Butterworth, 1998), and cateholaminergic toxins (Zhang et al., 1996).

(–)-Deprenyl has not been universally effective in reducing cell death (Ballabriga et al., 1997; Fang et al., 1995; Rothblat and Schneider, 1998; Thiffault et al., 1997; Vaglini et al., 1996). In some cases, (–)-deprenyl has been found to be highly effective or ineffective in reducing neuronal death in similar models. For example, three groups exposed adult gerbils to 5 minutes of bilateral carotid occlusion and began daily (–)-deprenyl treatment at 1–2 hours after the occlusion. One group evaluated CA1 hippocampal neuronal numbers at day 4 after daily treatment with 10 mg/kg (–)-deprenyland found no increase in survival (Ballabriga et al., 1997). The other evaluated CA1 hippocampal neuronal numbers at days 3 or 7 after treatment with 0.25 mg/kg and found a significant increase in survival at both time points (Lahtinen et al., 1997). A third group evaluated 0.25 mg/kg daily (–)-deprenyl treatment on hypoxia/ischemia induced rat CA1, CA3 and CA4 hippocampal neuronal death at multiple time points up to 14 days and found markedly significant increases in neuronal survival (Paterson et al., 1997).

Three different factors have been proposed to account for models in which (–)-deprenyl is ineffective: 1) that (–)-deprenyl can only reduce neuronal death mediated by apoptosis but not that mediated by necrosis. For example high levels of MPTP or MPP+induce necrosis while lower levels induce apoptosis (Hartley et al., 1994; Mochizuki et al., 1994; Spooren et al., 1998; Tatton et al., 1997). The levels of MPTP or MPP+ that were employed may explain studies in which (–)-deprenyl was effective (Koutsilieri et al., 1996; Koutsilieri et al., 1994; Mytilineou and Cohen, 1985; Schmidt et al., 1997; Tatton and Greenwood, 1991; Tatton et al., 1993; Wu et al., 1995) versus those in which it was ineffective (Rothblat and Schneider, 1998; Thiffault et al., 1997; Vaglini et al., 1996). Similar variability in the rapidity and depth of hypoxia may account for the variable effectiveness of (–)-deprenyl in hypoxia/ischemia models considered above. 2) that (–)-deprenyl may only by effective in some forms of apoptosis but not in other forms. Paterson showed that (−)-deprenyl reduced apoptosis of cultured cerebellar granule cells induced by cytosine arabinoside but not that induced by low potassium levels (Paterson et al., 1998). Similar our group has found that (−)-deprenyl reduces apoptosis in PC12 cell that have been exposed to serum and NGF (Tatton et al., 1994; Wadia et al., 1998) but not those that have only been exposed to serum (Chalmers-Redman and Tatton, unpublished observations). Similarly, (−)-deprenyl does not reduce apoptosis in the classic model of dexamethasone-exposed lymphocytes (Fang et al., 1995). Paterson (Paterson et al., 1998) has proposed that (−)-deprenyl only reduces those forms of apoptosis that involve a mitochondrial decision point (see above). For example, cytosine arabinoside induced apoptosis of cerebellar granule cells involves an early decrease in $\Delta\psi_M$ while apoptosis induced by low potassium in the same cells does not involve early decreases in $\Delta\psi_M$. (−)-Deprenyl is effective in the former but not the latter. Similarly, apoptosis in PC12 cells exposed to serum and NGF involves an early decrease in $\Delta\psi_M$ and is responsive to (−)-deprenyl (Wadia et al., 1998) while that in PC12 cells that have only been exposed to serum does not involve an early decrease in $\Delta\psi_M$ and is unresponsive to (−)-deprenyl (Chalmers-Redman and Tatton, unpublished observations). Lastly, dexamethasone induced lymphocyte apoptosis does not involve an early decrease in $\Delta\psi_M$ (Zamzami, personal communication) and is not (−)-deprenyl responsive. Accordingly, those forms of apoptosis that do involve an early decrease in $\Delta\psi_M$ may not respond to (−)-deprenyl. 3) Recently, it has been suggested, but not proven, that the primary metabolite of (−)-deprenyl, (−)-desmethyldeprenyl (DES), mediates anti-apoptosis rather than (−)-deprenyl itself (Mytilineou et al., 1997). Accordingly, variations in (−)-deprenyl effectiveness from model to model may depend on the tissues capacity to convert (−)-deprenyl to DES.

1.5.1 (−)-Deprenyl Requires New Protein Synthesis To Reduce Apoptosis And Alters Gene Expression And Protein Synthesis In Pre-Apoptotic Cells Studies in neuronally-differentiated PC12 cells showed that transcriptional inhibition by actinomycin and translational inhibition by cycloheximide or campothecin blocked the capacity of (−)-deprenyl to reduce apoptosis in the cells (Tatton et al., 1994). In a variety of cell types, (−)-deprenyl has been shown to increase gene expression, protein levels or protein activity for superoxide dismutases (SOD1 and SOD2) (Carrillo et al., 1991; Kitani et al., 1994; Li et al., 1998; Thiffault et al., 1995), BCL-2 (Tatton and Chalmers Redman, 1996), heat shock protein 70 (Lahtinen et al., 1997; Zhang et al., 1996), GFAP (Amenta et al., 1994; Biagini et al., 1994; Biagini et al., 1993; Ju et al., 1994; Li et al., 1993; Revuelta et al., 1997), aromatic amino acid decarboxylase (Li et al., 1992), tyrosine hydroxylase (Li et al., 1997; Reinhard and JP, 1991; Rodriguez-Gomez et al., 1997), CNTF (Seniuk et al., 1994), NGF (Li et al., 1997; Semkova et al., 1996), FGF (Biagini et al., 1994), and trk receptor (Ekblom et al., 1994).

It is not known whether any of the above proteins are associated with the capacity of (−)-deprenyl to reduce apoptosis. SOD1 underexpression increases apoptosis while its overexpression decreases apoptosis in PC12 cells and sympathetoblasts (Greenlund et al., 1995; Troy and Shelanski, 1994) making an increase in SOD1 expression a candidate for the anti-apoptotic effects of (−)-deprenyl. The capacity of (−)-deprenyl to increase SOD1 has been shown to vary from tissue to tissue (Carrillo et al., 1992; Lai et al., 1994), which might also explain the variability in (−)-deprenyl effectiveness. BCL-2 may also contribute to (−)-deprenyl anti-apoptosis. BCL-2 has been shown to prevent the fall of $\Delta\psi_M$ that is characteristic of some forms of apoptosis (Kroemer et al., 1997; Susin et al., 1996) and (−)-deprenyl also prevents a fall in $\Delta\psi_M$ in neuronally differentiated PC12 cell (Wadia et al., 1998) and cerebellar granule cell apoptosis (Paterson et al., 1998). A decrease in BCL-2 levels has been shown to contribute to the fall in $\Delta\psi_M$ in apoptotic cells (Kroemer et al., 1997; Susin et al., 1996) while a maintenance of BCL-2 through its new synthesis would prevent a fall in $\Delta\psi_M$ and the initiation of apoptosis.

It has been suggested that the anti-apoptotic action of (−)-deprenyl on neurons is mediated by the capacity of the compound to increase the synthesis of CNTF (Seniuk et al., 1994), NGF (Semkova et al., 1996) and bFGF (Biagini et al., 1994) by astrocytes (Koutsilieri et al., 1996). According to that proposal, (−)-deprenyl would increase the provision of trophic support to damaged neurons on astroglia and thereby reduce apoptosis.

It is not known whether (−)-deprenyl or one or more of its metabolites can influence apoptosis in oligodendroglial cells. Furthermore, it is not known whether any effects of (−)-deprenyl on oligodendroglial cells involves new protein synthesis and/or whether (−)-deprenyl has any effect on $\Delta\psi_M$ in the cells.

1.6 Specific Aims

1. To establish a tissue culture model system to study whether IGF–I and insulin withdrawal causes apoptosis in differentiated cells of the O–2A cell lineage like the PROLs and OLs similar to that observed in the progenitor cell population.

Primary cultures of oligodendrocytes will be established by obtaining purified populations of O-2A progenitor cells isolated from the rat cerebral cortex and differentiating them in the presence of trophic factors, insulin and IGF–I. The different cell types of the O-2A lineage will be identified on the basis of morphological and immunocytochemical criteria. Apoptotic degradation will be studied using multiple complementary approaches including a) staining of chromatin with fluorescent DNA binding dyes; b) gel electrophoresis of DNA and c) in situ end labeling (ISEL) of nicked 3 ends of DNA.

2. To determine the time course of any apoptotic death of the insulin and IGF-I withdrawn PROLs and OLs.

An estimate of the time course of cell death will be obtained from counts of ISEL positive apoptotic nuclei of PROLs and OLs after 6, 12, 15, 18 and 24 h after withdrawal of insulin and IGF-I.

3. To determine whether (−)-deprenyl can reduce apoptosis in PROLs and OLs.

The effects of (−)-deprenyl on cell survival will be determined by obtaining nuclear and cell counts. The numbers of ISEL positive nuclei will also be examined to determine whether they are appropriately reciprocal to the cell numbers. DNA electrophoresis gels will be used to determine whether (−)-deprenyl eliminates or reduces DNA "laddering" at appropriate time points.

4. To determine whether any anti-apoptotic effects on the PROLs and the OLs are brought about by (−)-deprenyl itself or by one of its metabolites, like (−)-desmethyldeprenyl.

The intact nuclear count method will be used to quantify the effects of the metabolites of (−)-deprenyl on the survival of the PROLs and the OLs. Three general cytochrome P450 blockers will be used to determine if the blocking of metabolism of (−)-deprenyl or a metabolite eliminates any increased PROL and OL survival induced by the compound.

5. To determine whether any anti-apoptotic action of (−)-deprenyl and/or an active metabolite requires new protein synthesis by using actinomycin D to inhibit transcription and cycloheximide to inhibit translation.

6. To determine whether (−)-deprenyl or an active metabolite modifies the levels of PROL and OL specific proteins.

Western blot analysis of individual proteins will be used to analyze changes in the levels of PROL and OL specific proteins.

7. To determine whether a decrease in $\Delta\psi_M$ is involved in any OL and PROL apoptosis induced by IGF-I and insulin withdrawal.

The involvement of mitochondria in the apoptotic death of PROLs and OLs will be determined using $\Delta\psi_M$ changes as an indicator. The mitochondrial potentiometric dye, chloromethyltetramethyl rosamine (CMTMR) will be imaged in individual mitochondria in intact cells using confocal laser microscopy.

8. To determine whether treatments with (−)-deprenyl or an active metabolite or those that block decreases in any apoptosis in PROLs and OLs have appropriate actions on $\Delta\psi_M$.

2.0 Materials and Methods 2.1.1 Preparation of Mixed Primary Glial Cultures

Primary cultures enriched in O-2A progenitors grown over a monolayer of astrocytes were derived from the cerebral cortex of 2-day-old rat pups. Timed pregnant Sprague Dawley rats (Charles River, Montreal, Canada) were obtained at 18 days gestation and housed in the Carleton Animal Care Facility at Dalhousie University. Two litters (consisting of about 10–12 pups/litter), obtained at postnatal day 2, were used in each experiment. The rat pups were anesthetized with a brief exposure to an inhalant anesthetic, Metofane and then quickly decapitated. Using sterile technique, the skull was opened via the foramen magnum towards the olfactory bulb and the skull flaps were pried open carefully. With a microspatula, the entire brain was lifted away and placed in cold Dulbecco's modified Eagle's medium (DMEM; GibcoBRL, Life Technologies, Ontario, Canada) supplemented with 15% fetal bovine serum (FBS; Hyclone Laboratories Inc, Utah, USA). Subsequently, the meninges were removed and the cerebral hemispheres transferred to another sterile petridish. The cerebral hemispheres were then dissected under a stereomicroscope and the cortices isolated free of the midbrain, hippocampus and the striatum. Using a cell scraper all the neocortical tissue was mechanically dissociated and filtered successively through 210 and 130 μm Nitex meshes (B&SH Thompson & Co Ltd, Ontario, Canada). This procedure allows for the elimination of contaminating fibroblasts. The cell suspension was centrifuged at 300×g in 50 ml tubes using a Sanyo Mistral 3000i centrifuge and the cells pelleted and resuspended in DMEM containing 15% serum. Viable cells, as determined by the Trypan Blue dye exclusion, were counted on a haemocytometer and plated at a density of $1.37\times10^6$ cells/ml onto 185 cm² Nunc culture flasks.

The mixed cultures were grown for 10 days in a media containing DMEM, 15% FBS, penicillin (50 IU/ml), streptomycin (50 μg/ml), 1 mM sodium pyruvate; 50 μg/ml transferrin (Sigma Chemical Co., MO, USA); 0.005 μg/ml sodium selenite (Sigma) and 5 μg/ml insulin (Upstate Biotechnology Inc, NY, USA) until confluent. The media was replaced every 3 days.

2.1.2 Preparation of Secondary Cultures

Secondary cultures enriched in pure populations of oligodendrocytes were obtained by a modification of the selective adhesion protocol of (McCarthy, 1980). By 10 days in vitro (DIV), the O-2A progenitor cells had spread in clusters over the confluent layer of astrocytes. The flasks were then subjected to a 'preshake' at 170 rpm for 1 hour, 37° C., (in order to release macrophages, dead cells and debris) on an orbital shaker (Aros 160, Thermolyne) with an inch and a quarter stroke diameter. The preshake was followed by an 18 hour shake at 230 rpm. Medium containing the detached O-2A cells was recovered and filtered through a 20 μm Nitex mesh to remove clumps of dead cells and larger type-1 astrocytes. The cell filtrate was plated for 5 min in a plastic petridish in order to separate the O-2A progenitor cells from microglia. The loosely adherent O-2A cells were detached by incubating them in a solution of 10 mM Tris and 1 mM EDTA (pH 7.4) at 37° C. for 5 min. The cells were subjected to centrifugation at 300×g for 5 min and cells were resuspended in an oligodendrocyte differentiating media (ODM) containing DMEM, 10% FBS, 16 μg/ml putrescine (Sigma), 0.006 μg/ml progesterone (Sigma), 5 μg/ml insulin, 2.5 ng/ml insulin-like growth factor-1 (Upstate), 50 μg/ml transferrin and 0.005 μg/ml sodium selenite. The ODM was based on a modification of the defined medium as described by Hunter (Hunter and Bottenstein, 1990).

The cell suspension was plated on 12 mm and 22-mm coverslips (Assistent Glass, Carolina Biological Supply Co., Burlington, N.C., USA) as well as 24 well Nunc plastic plates. The coverslips used were alkaline etched (NaOH, 0.5 N) for 30 minutes. The coverslips were then thoroughly washed with distilled water, autoclaved and subsequently poly-L-lysine (Sigma, P6282) coated. The cell suspension was plated at two different densities: 1) $5.3\times10^3$ cells/mm2 (experimental series I) and 2) $15.8\times10^3$ cells/mm² (experimental series II). The cells were maintained in ODM with 10% FBS for 3 hr at 37° C. to enhance survival following which the media was replaced with ODM with low serum (containing 1% FBS). The O-2A progenitors were then allowed to differentiate for a further 6 days, and monitored by phase contrast microscopy to determine when the majority of the cells could be morphologically identified as OLs. Phase contrast micrographs of the differentiating O-2A progenitors were taken using a Leitz inverted phase contrast microscope coupled to a CCD camera.

2.2 Immunocytochemical Detection of Cultured Oligodendroglial Cells

Cells growing on coverslips were identified by immunocytochemistry for specific markers of oligodendrocyte development like A2B5 (Eisenbarth et al., 1979), 2'-3'-cyclicnucleotide-3'-phosphorylase (CNPase) (Knapp, 1988), galactocerebroside (GC) (Ranscht, 1982), myelin basic protein (MBP) (Lees, 1984) and proteolipid protein (PLP) (Bartlett et al., 1988).

Cells growing on coverslips were fixed with 2% paraformaldehyde for 15 minutes at room temperature. The coverslips then washed three times with 0.1 M phosphate buffered saline (PBS). Non-specific binding of protein was blocked by incubating the coverslips in 10% normal goat serum at room temperature for an hour, followed by permeabilization with 0.1% Tween-20 (Sigma) for 20 minutes at room temperature. Endogenous peroxidase was blocked by incubating the coverslips in 1% $H_2O_2$ for 10 minutes. Subsequently, the coverslips were incubated overnight at 4° C. with primary antibodies. PROLs were identified by a using a primary antibody to mouse anti CNPase (1:100; Sigma C-5922) while OLs were identified using antibodies to rabbit anti MBP (1:100; Zymed Laboratories Inc, San Francisco, Calif., USA #18–0038) and rat anti PLP (1:100; Immunodiagnostics Inc, Bedford, Mass., USA #9021). Astrocytes were identified by mouse anti glial fibrillary acidic protein (GFAP) (1:200; Sigma G-3893). All primary antibodies were diluted in 0.1 M PBS/1% normal goat serum/0.1% Tween-20. In order to detect surface antigens present in O-2A progenitors (A2B5) and PROLs (GC), antibodies mouse anti A2B5 (1:100; Boehringer Mannheim, Quebec, Canada, 1300 016), rabbit anti-GC (1:50; Boehringer Mannheim, 1351 621) were applied to living cells for 30 minutes.

Following the primary antibody incubation, coverslips were washed 3 times with 0.IM PBS. Coverslips were then incubated with the appropriate biotinylated goat anti-mouse, goat anti-rabbit or goat anti-rat IgG secondary antibody (1:500; Vector Labs) at room temperature for one hour. Subsequently, after three washes with 0.1M PBS the coverslips were incubated for 30 minutes with avidin-HRP (Elite Kit, Dimension Laboratories Inc., Missisauga, Ontario, Canada). Coverslips were washed with PBS and chromogenic detection was carried out using diaminobenzidine (DAB, 1.5 mg/ml) mixed with an equal volume of hydrogen peroxide ($H_2O_2$; 0.02% v/v) to obtain a brown reaction product within 5 min localizing the specific antigens. Coverslips were then dehydrated in ascending grade alcohol series, cleared with xylene and mounted on slides using a drop of permount.

2.3 IGF-I and Insulin Withdrawal and Culture Treatment Conditions

In order to examine insulin and IGF-I dependent survival of the cells of the oligodendroglial lineage, cells were trophically deprived for a period of 24 hours at 16 DIV. At this time in culture, the O-2A progenitor cells had differentiated into CNPase immunopositive PROLs and MBP immunopositive OLs.

Cells were trophically withdrawn by replacing the media with a serum free, chemically-defined base media (BM) lacking insulin and IGF-I (Bottenstein et al., 1988). The base media consisited of DMEM supplemented with penicillin (50 IU/ml); streptomycin (50 µg/ml); 1 mM sodium pyruvate; 50 µg/ml transferrin; 0.005 µg/ml sodium selenite; 16 µg/ml putrescine; 0.006 µg/ml progesterone and 0.1 mg/ml bovine serum albumin. All the cells were washed with BM twice before exposing them to individual treatment conditions. Control cells were washed and placed in BM supplemented with 2.5 ng/ml IGF-I and 5 µg/ml insulin to form the insulin media (IM).

To study the effects of trophic-like agents on the survival of oligodendroglial enantiomers of deprenyl. The ability to induce increases in survival of oligodendroglial cells was seen restricted to R (–)-deprenyl and henceforth this enantiomer was used. Experiments involving dose response of (–)-deprenyl showed that a concentration of $10^{-9}$ M was most effective in increasing oligodendroglial cell survival hence this concentration of deprenyl was used in all subsequent experiments. For deprenyl treatment, cells were washed twice in BM to remove any serum borne survival factors and the media was replaced with BM supplemented with $10^{-9}$ M (–)-deprenyl (BM-D9). A second control group consisted of cells that were washed and placed in IM supplemented with $10^{-9}$ M (–)-deprenyl (IM-D9).

2.4 Assessment of Cell Survival by Nuclear Integrity Assay

Cell survival in the cultures was assessed according to the method of (Soto and Sonnenschein, 1985). After washing and treatment in BM, BM-D9, IM and IM-D9 for 24 h, cells were harvested, centrifuged at 500 rpm for 5 min and the supernatant removed. Pelleted cells were then lysed with 200 µl of 10% Zap-oglobin (Coulter Electronics, FL, USA). The lysing agent is a detergent containing solution that lyses the plasma membrane but leaves the nuclei intact. The lysed solution was collected and vortexed. A small volume (10 µl) of the solution was removed and intact nuclei were counted using a haemocytometer. To be counted, nuclei had to show a completely intact smooth outer border. Counts of intact nuclei were pooled for three or four experiments (a total of 15–20 wells were used for each treatment condition). each treatment condition).

2.5 Morphological Identification by Methylene Blue Staining and Cell Counts

Methylene blue (3,7-bis (dimethylamino)-phenothiazin-5-ium chloride), a ribonucleic acid (RNA) binding agent commonly used as an alternative nucleic acid stain, can also be used as a biological staining agent to stain cells in order to observe their morphological features. At 24 h, cells were fixed in 2% paraformaldehyde for 15 min at room temperature. Briefly, cells were washed twice with PBS and 100 µl of 1% methylene blue (Mallinckrodt Chemical Co., MO, USA) solution containing 1% $AgNO_3$ was added for 10 min to the wells containing coverslips. Subsequently, the coverslips were washed with two changes of distilled water and absolute ethanol, cleared with xylene and mounted on slides with permount.

Cell counts were performed for 25 randomly chosen 100 power fields on each coverslip. Two randomly generated coordinates drawn from a uniform distribution of random numbers specified the center of each field. The random numbers were generated on a computer by using Microcal Origin 4.0 program. Comparison of the counts found by the random method to counts of all the cells on a given slide revealed differences of less than +/–3%. Three coverslips was counted for each treatment condition. In subsequent experiments, different cell types (for example, O-2A progenitors, PROLs, OLs and astrocytes) were morphologically identified on each field and were counted separately for experimental series-I and II. Interference contrast images of the four oligodendroglial lineage cell types were obtained using a Leitz orthoplan microscope and Metamorph software program (Universal Imaging, PA, USA).

2.6 Nuclear Chromatin Staining with Hoechst 33258

Apoptosis and necrosis can be distinguished on the basis of changes in nuclear chromatin. Light microscopic studies have shown that the characteristic ultrastructural event during apoptotic cell death is the formation of phase dark, crescent shaped and marginated masses of nuclear chromatin (Wyllie, 1987). Necrotic cells on the other hand, show irregular and ill-defined chromatin. Chromatin in necrotic cell death eventually scatters into many loosely associated particles, a phenomenon also known as karyorrhexis (Wyllie et al., 1981).

In order to observe changes in nuclear chromatin during trophic withdrawal and anti-apoptotic compounds, oligodendrocytes at 16 DIV, were exposed for 24 hours to the treatment conditions as described in section 2.4. At 24 h, cells were fixed with 2% paraformaldehyde for 15 minutes at room temperature and subsequently washed three times in PBS. The coverslips were then incubated with 1 µg/ml 2'-(4-hydroxyphenyl)-5-(4-methyl-1-piperazinyl)-2-5'-bi-1H-benzimidazole trihydrochloride pentahydrate (Hoechst 33258, Molecular Probes) in distilled water for 30 min to visualize nuclear chromatin.

Hoechst 33258 is a supravital bisbenzimide dye, which binds to contiguous A-T bases in DNA. The coverslips were washed three times for 5 min with PBS, mounted in glycerol and viewed with epifluorescence microscopy using 340–380 nm excitation and emission filtration of 430 nm long pass.

2.7 DNA Extraction and Electrophoresis

DNA was extracted from trophically withdrawn as well as trophically supported oligodendroglial cells and electrophoresed in order to determine the nature of DNA degradation. Oligodendrocytes were cultured in poly-L-lysine coated 100-mm$^2$ culture dishes at a density of 1×10$^6$ cells per dish. At 16 DIV, the cultures were exposed to BM, BM-D9, IM and IM-D9 for 24 h. The DNA was extracted following the method of Batistatou and Greene (Batistatou and Greene, 1993).

Cells were lysed with 1 ml of lysis buffer (10 mM Tris, pH 8.0, 1 mM EDTA, 150 mM NaCl and 0.1% SDS). The lysate was then incubated overnight at 65° C. in 20 µg/ml proteinase K (Fisher Scientific, Montreal, Canada) to eliminate contaminating proteins. This was followed by 2-hour (37° C.) incubation in 5 µg/ml DNAse-free RNAse A (Boehringer Mannheim) to digest RNA. The samples were then extracted twice with a solution of phenol, chloroform, isoamyl alcohol (25:24:1; GibcoBRL). DNA in the lysates was precipitated with 3M sodium acetate (pH 5.2) and ethanol. Subsequently the samples were centrifuged for 30 minutes at 13,000 rpm and a DNA pellet was obtained. The DNA pellet was washed in 70% ethanol and air-dried. The DNA pellet was resuspended in 20 µl of TE buffer (10 mM Tris, 1 mM EDTA; pH 8.0) and mixed completely.

Each DNA sample (10 µl) was mixed with 2 µl of loading buffer (40% Sucrose, 0.25% Bromophenol blue, 0.25% Xylenecyanol) and electrophoresed in a 1.2% agarose (in 1 X TAE buffer) minigel at 55V for 1 to 1½ hours. A stock solution of 1 mg/ml ethidium bromide made up to a final concentration of 0.5 µg/ml in TAE (Tris base, acetic acid, EDTA 0.5M; pH 8.6) was used to stain the gels. The gels were photographed on a transilluminator with ultraviolet light using a Polaroid DS-34 camera. Images of the films obtained from the electrophoresis gels were digitized using a Matrox frame grabber and Metamorph software (Universal Imaging, W. Chester, Pa.).

2.8 In Situ DNA End Labeling of Oligodendrocytic Cells

The ApopTag™ method utilizes an ApopTag™ in situ apoptosis detection kit (Oncor, Md., USA), which detects nuclei with, cut 3'-OH ends of DNA. Oligodendrocytes at 16 DIV were treated with BM, BM-D9, IM and IM-D9 for 6, 12, 15, 18 and 24 h. Cells were fixed in 2% paraformaldehyde, followed by three washes in 0.1M PBS and permeabilization with 0.05% Tween-20 in PBS for 10 min at room temperature. Endogenous peroxidase was quenched with 1% $H_2O_2$ in PBS for 5 min at room temperature. Coverslips were then covered with 1 X equilibration buffer for 30 min at room temperature and then incubated with terminal deoxynucleotidyl transferase (TdT)/reaction buffer (76 µl of reaction buffer+32 µl of TdT enzyme) for 1 h at 37° C. A stop wash buffer incubation for 30 min at 37° C. was used to terminate the 3'-OH DNA extension reaction. After a PBS wash, the coverslips were incubated with antidigoxigenin peroxidase antibody. After three washes with 0.1M PBS, chromogenic detection was carried out using DAB (1.5 mg/ml) mixed with hydrogen peroxide ($H_2O_2$; 0.02% v/v) yielding a brown reaction product. Coverslips were dehydrated in ascending grade alcohol series, cleared with xylene and mounted on slides using a drop of permount. ApopTag™ positive nuclei were randomly counted in triplicate (described in section 2.5), for each of the time points, for experimental series-I and II.

2.9 Determination as to Whether (−)-Deprenyl or its Metabolites are Responsible for Oligodendrocyte Anti-Apoptosis The capacity of the three major metabolites of (−)-deprenyl, namely, (−)-desmethyldeprenyl, (−)-amphetamine and (−)-methamphetamine (Heinonen et al., 1994) to reduce the death of the oligodendroglial cells was assayed using the nuclear integrity assay. Three different general cytochrome P450 blockers-proadifen (Sigma), piperonyl butoxide; Aldrich Chem Co., WI) and 2-methyl-1,2-di(3-pyridyl)-1-propanone (metapyrone; Aldrich) were used to block the cytochrome P450 dependent metabolism of (−)-deprenyl to (−)-desmethyldeprenyl as a means of determining whether a metabolite, rather than (−)-deprenyl was responsible for any changes in survival.

OLs at 16 DIV were exposed to the different drug treatment conditions for 24 h, following which, the nuclear integrity assay was performed. On the day of the treatment, the cells growing in Nunc 24 well plates were washed twice with base media. Each treatment well received 50 µl of the appropriate drug solution and the total volume in the well was made up to 500 µl with either BM or IM.

Nuclear counts were obtained from quadruplicate wells per treatment condition and the experiment was repeated twice. OLs were exposed to the following treatment conditions: 1) IM, 2) BM, 3) BM-D9, 4) (−)-Desmethyldeprenyl (BM-Ds9), 5) IM-D9 and 6) IM +10$^{-9}$ M (−)-Desmethyldeprenyl (IM-Ds9).

The treatment conditions with the three general cytochrome P450 blockers were: 1) BM+Proadifen (2.5, 10, 25 µM), 2) BM-D9+Proadifen (2.5, 10, 25 µM), 3) BM-Ds9+Proadifen (2.5, 10, 25 µM), 4) BM+Metapyrone (50 µM), 5) BM-D9+Metapyrone (50 µM), 6) BM-Ds9+Metapyrone (50 µM), 7) BM+Piperonyl butoxide (100 µM), 5) BM-D9+Piperonyl butoxide (100 µM), 6) BM-Ds9+Piperonyl butoxide (100 µM).

The effects of the other two metabolites of (−)-deprenyl, namely, (−)-methamphetamine and (−)-amphetamine on oligodendroglial cell survival were also tested. (−)-Methamphetamine was used at three doses (10$^{-5}$ M, 10$^{-7}$ M, 10$^{-9}$ M) in combination with 10$^{-9}$ M (−)-deprenyl while a single dose of 10$^{-5}$ M (−)-methamphetamine was used with 10$^{-9}$ M (−)-desmethyldeprenyl.

(−)-Amphetamine was used in four concentrations (10$^{-3}$ M, 10$^{-5}$ M, 10$^{-7}$ M, 10$^{-9}$ M) with (−)-deprenyl (10$^{-9}$ M) while a single concentration of 10$^{-5}$ M (−)-amphetamine was used in combination with (−)-desmethyldeprenyl (10$^{-9}$ M).

2.10 Determination of the Relationship Between New Protein Synthesis and Apoptosis in Oligodendrocytes After determining that the alterations in oligodendroglial apoptosis was in fact induced by (−)-desmethyldeprenyl, a principal metabolite of (−)-deprenyl, the next logical step was to determine whether (−)-desmethyldeprenyl exerted its effects by a transcriptional- or a translational-dependent mechanism.

OLs at 16 DIV were washed twice with base media and exposed either to actinomycin, a transcriptional blocker or cycloheximide, a translational blocker for 24 h. Actinomycin was used at 1, 2.5 and 50 µg/ml and cycloheximide at 1, 5, 10 and 50 µg/ml. Actinomycin and cycloheximide were either used with base media alone or in combination with 10$^{-9}$ M (−)-desmethyldeprenyl. Each treatment well received 50 µl of the drug solution and the total volume of the well was made up to 500 µl with base media.

Counts of intact nuclei, obtained from quadruplicate wells per treatment condition were used to quantitate the effects of the transcriptional and translational blockers. Each experiment was repeated twice for experimental density series-II.

2.11 Analysis of Changes in PROL and OL Protein Levels 2.11.1 Protein Extraction O-2A progenitor cells were plated at a density of 1×10$^6$/100 mm petridishes. The progenitor cells were allowed to differentiate into PROLs and OLs in the presence of insulin and IGF-I. At 16 DIV, cultures were exposed to BM, IM, BM-D9 or BM-Ds9 for 24 h. Subsequently, cells were washed twice with 0.1M PBS, pH 7.4 and harvested with a Falcon cell scraper. After centrifugation at 2000× g for 5 min in a Mistral 2000 centrifuge, the cells were incubated in 100 μl of cell lysis buffer (25 mM Tris, pH 8.0, 0.5% Triton-X-100, 1 mM EDTA, 10 mM PMSF, 5 mM Benzamidine, 5 μM leupeptin). The lysate was homogenized with a plastic homogenizer. The lysate was centrifuged at 2000× g for 5 minutes at 4° C. The supernatant containing the protein fraction was collected. A small volume of the protein solution was used to estimate the protein concentration. The rest of the protein solution was stored at −20° C. until use.

2.11.2 Estimation of Protein Concentration

Total protein of the aliquot was determined by spectrophotometry based on the Bradford dye binding procedure (Bradford, 1976) using Coomassie Brilliant Blue (Pierce, Rockford, Ill.). Coomassie Brilliant Blue dye binds primarily to basic or aromatic residues on proteins and in the presence of the protein converts from cationic (red) to the anionic (blue) form by successive protonations. This conversion was quantitated by a Hitachi spectrophotometer at a wavelength of 595 nm. The assay was carried out by measuring the binding of the dye to the unknown protein. The protein-dye binding was then compared to different amounts of a standard protein, bovine serum albumin (BSA). Proteins with a molecular weight greater than 3–5 kDa are sensitively quantitated by the Bradford protein assay.

2.11.3 SDS-PAGE Electrophoresis

The protein samples obtained from the cultures after a 24-hour treatment period were separated by sodium dodecyl sulfate-polyacrylamide gel electrophoresis (SDS-PAGE) in duplicate. The SDS-PAGE electrophoresis separates proteins based on molecular size as they move through the polyacrylamide gel matrix from the cathode towards anode. The percentage of acrylamide in the separating gel depends on the molecular size of the protein electrophoresed. Proteins smaller than 50 kDa like MBP and PLP were resolved on a 10% SDS-PAGE discontinuous gel while proteins larger than 50 kDa like GC and CNPase-I were separated on a 15% SDS-PAGE discontinuous gel.

A 30% stock acrylamide solution was made up. A separating and stacking gel mix was prepared using stock acrylamide, water, separating or stacking gel buffer, N,N,N',N'-tetramethyl ethylenediamine (TEMED) and ammonium persulfate (APS). APS was always made fresh for each experiment. The glass plate sandwich with spacers was assembled and placed in a Bio Rad Mini Protean II gel apparatus. Using Pasteur pipets, the separating gel was poured and the top of the gel was covered with a layer of isobutyl alcohol. The separating gel was allowed to polymerize for 1 h at room temperature. The overlaid isobutyl alcohol on the separating gel was poured out and the stacking gel was poured. Subsequently, a 10 well Teflon comb was placed in the stacking gel and the gel was allowed to polymerize. The protein samples were solubilized in sample buffer (glycerol, Tris, pH 6.8, 0.01% Bromphenol blue, 20 mM Dithiothreitol, SDS) in a 1:1 ratio, sample to buffer. The protein samples in tubes were transferred to a 100° C. water bath for 5 minutes to inactivate proteases. The samples were then loaded carefully as a thin layer on the bottom of the polymerized wells. An electrophoresis buffer (Glycine, Tris, pH 8.3, SDS) was used to fill up the upper and lower buffer chambers. A Bio-Rad model 250/2.5 power supply was used to resolve the samples at 70 volts through the stacking gel and at 100 volts through the separating phase of the gel.

2.11.4 Detection of Proteins by Western Blotting Immunodetection Method

The oligodendroglial proteins separated by SDS-PAGE were transferred to Hybond-C nitrocellulose membrane (Amersham Life Science) which is optimized for protein transfer, using a Bio-Rad Mini Protean II transfer apparatus. All the filter papers and nitrocellulose membranes were first equilibrated in a transfer buffer (Glycine, Tris, SDS, 20% Methanol). The transfer apparatus was connected to a power supply and the protein transfer was carried out at 100 mA for 3 h. After the transfer period, the membrane was removed and proteins were visualized by staining for S min with Ponceau S stain (0.5% Ponceau S and 1% acetic acid). Ponceau S staining is primarily used to verify transfer efficiency. The membrane was destained with distilled water.

Prior to immunodetection, non-specific binding sites on the membrane were blocked by immersing it in a blocking buffer (5% Carnation nonfat dry milk in 0.1 M PBS) for an hour at room temperature with shaking. The membrane was rinsed with 0.1M PBS twice and incubated in a primary antibody overnight at 4° C. The primary antibodies used were diluted in 1% nonfat dry milk in PBS. The following monoclonal primary antibodies were used: rat anti-MBP (82–87 amino acid region) (1:400; Serotec Ltd., UK), rat anti-PLP (1:200; Immuno Diagnostics, Inc., MA), mouse anti-CNPase (1:500; Sternberger Monoclonals Inc., MD) and rabbit anti GC (1:250; Sigma). Following overnight incubation in primary antibodies, the membranes were washed four times with a wash buffer consisting of Tris Buffered Saline (TBS) containing 0.1% Tween-20. The blot was incubated in rat, rabbit or mouse IgG-horseradish peroxidase-conjugated secondary antibody for an hour at room temperature. The secondary antibody was used at a dilution of 1:500 in 1% nonfat dry milk. The blots were washed five times with TBS containing 0.1% Tween-20.

To visualize the antigen-antibody interaction in the immunoblots, an enhanced chemiluminescent method (ECL) was used. The horseradish peroxidase labeled ECL reaction involves a substrate solution containing luminol. Oxidized luminol substrate gives off a blue light that can be trapped on a film. For the ECL reaction, a Supersignal™ Substrate (Pierce, Rockford, Ill.) working solution containing luminol/enhancer solution and a stable peroxide solution in a 1:1 v/v ratio was used. The blots were placed in the Supersignal™ Substrate working solution for 5 minutes at room temperature with shaking. A sufficient amount of the solution was used to ensure that the blot remained completely wetted. After five minutes, the blot was removed from the Supersignal™ Substrate working solution and placed in a plastic wrap. Any excess of the working solution or bubbles between the blot and the plastic wrap was removed. The blots were placed against a Kodak Biomax-MR double emulsion film in an autoradiographic cassette. Typically, blots were exposed to the films for 1–10 seconds and the films were developed.

2.12 Assessment of Mitochondrial Membrane Potential in Oligodendroglial Cells

2.12.1 CMTMR Estimation of Mitochondrial Membrane Potential

The $\Delta\psi_M$ was assessed by the addition of a lipophilic, potentiometric dye, chloromethyl-tetramethylrhodamine methyl ester (CMTMR, Mitotracker Orange™ Molecular Probes, Eugene, Oreg.). The CMTMR dye reacts with the thiol groups on proteins and peptides to form aldehyde fixable conjugates. Entry of the negatively charged mitochondrial matrix compartment is proportional to the difference in the membrane potential. Therefore, the CMTMR fluorescence labels the mitochondrial membrane potential generated due to the negativity difference between the mitochondrial matrix and the outside of the mitochondria. Upon cell fixation, CMTMR remains in the mitochondria and is not washed out unlike other mitochondrial potentiometric dyes like rhodamine123.

Oligodendrocytes at 16 DIV were placed in trophically deprived BM for 18 h or treated with BM-D9 or BM-Ds9. Other treatments of cultures included exposure to the general cytochrome P450 blockers as well as the metabolites of (−)-deprenyl as previously described in section 2.8 of this thesis. At 18 h after trophic withdrawal or drug treatments, the media in each well was replaced with similar media containing 138 nM CMTMR. The cells were incubated in CMTMR at 37° C. for 15 min. The cells were then fixed with 4% cold paraformaldehyde on ice for 30 min and washed twice with 0.1M PBS. Consequently, the coverslips were mounted on glass slides with Aquamount (Gurr, England).

2.12.2 Confocal Microscopy

Individual mitochondria labeled with CMTMR were resolved by confocal microscopy. A Leica true confocal scanning (TCS) 4D microscope coupled to an argon-krypton laser (Omnichrome, USA) was used for cell imaging. A pinhole size of 20 with an excitation filter wavelength of 568 nm and an emission filter wavelength of 590 nm was used to image the CMTMR labeled mitochondria. Each field of the coverslip was imaged using an oil-immersion, 100 X, 1.3 N.A. objective at 512 by 512 by 8 bits per pixel resolution, background offset of −1 and line averaged 32 times in bi-directional line scan mode. Care was taken not to exceed the dynamic range of the gray value display. The confocal images obtained were saved on an optical drive in a tagged image file format (TIFF).

2.12.3 Measurement of CM R Fluorescence Intensity

Fluorescence intensity of individual mitochondria was measured using the Metamorph™ program. Metamorph™ compiles measurements of objects in a 8-bit image ranging from gray values 0 (background) and 255. In order to obtain fluorescence intensity measures, a rectangular region tool of 2×2 pixels was used to measure two randomly selected areas within each mitochondrion. A total of ten mitochondria obtained equally from all the regions of each cell were measured within each image. About 20 images were analyzed for each treatment condition thereby giving a sum of about 400 mitochondrial fluorescence intensity measures. The raw values were then further graphed and analyzed with the Microcal Origin 4.1 program. Frequency count was performed on the data, which classified the data in ordered bins. A frequency distribution was obtained with lower bin value set at 0 and higher bin value set at 260.

2.13 Statistical Analysis

In order to statistically evaluate the data, the individual measurements of data from different treatment groups were first analyzed using Statistica™ software (StatSoft) to carry out two-tailed independent sample t-testing. Analysis with parametric methods such as the t-test may not provide valid results, especially with small n numbers. The data was therefore rank ordered and compared in a pairwise fashion using Statistica™ software to perform non-parametric Mann Whitney U testing (Siegel, 1956). Both methods depend on permutational mathematics to calculate significance values and therefore do not require homogeneity of variances, that the underlying distributions for the data be known, or that the values are linearly related.

3.0 Results 3.1 Differentiation and Maturation of O-2A Progenitors

Figure 2A:
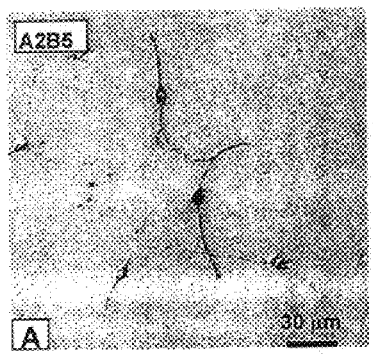
FIG. 2: Immunocytochemical characterization of the cells of the oligodendroglial lineage. 0-2A progenitors on 12 days in vitro (DIV) were labeled with an antibody to a surface tetraganglioside A2B5 (A). PROLs express CNP (B) and GC (C) on 13 DIV. OLs on 16 DIV reacted with anti-MBP (D) and anti-PLP protein (E) antibodies. Note MBP expression in the cell body and processes. An intense staining of PLP was found in the cell body. AST was identified by staining with an antibody to GFAP (F). GFAP positive ASTs show reticulated somal areas.
Figure 2B:
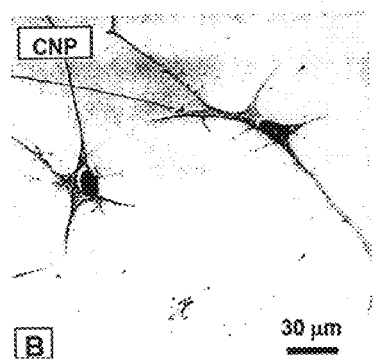
Figure 2C:
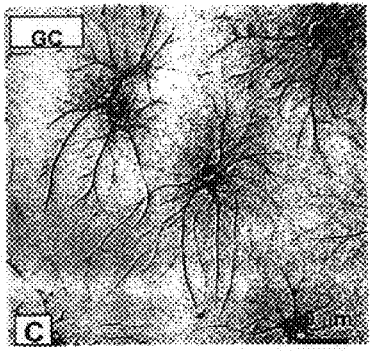

Phase contrast microscopy revealed cells with a round cell body of about 10 μm in diameter with a round nucleus and two long thin bipolar processes extending from the cell body at about an angle of 180 degrees to each other. Those cells were found to be immunopositive for an A2B5 antibody which is characteristic of O-2A progenitor cells (Eisenbarth et al., 1979). FIG. 1A shows a phase contrast image of a typical O-2A progenitor, which is marked by the white arrow. The interference contrast image in FIG. 2A shows four cells with the bipolar morphology that are immunopositive for A2B5. Only cells with the bipolar morphology were found to be A2B5 immunopositive. On 12 DIV, 24 hours after the cultured cells were removed from the astrocyte feeder layer and replated on coverslips at 11 DIV, A2B5 immunopositive cells accounted for more than 75% of the cultured cells.

Figure 1B:
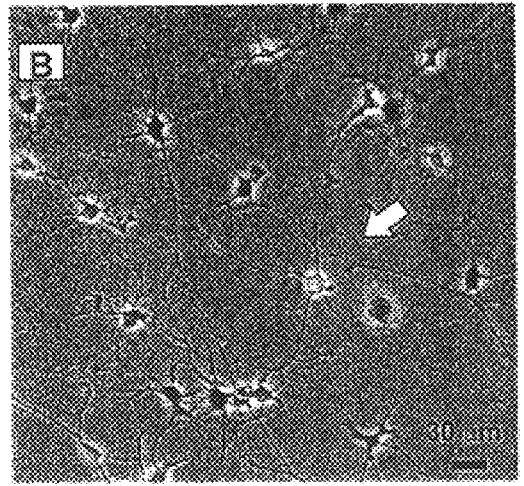
Figure 1C:
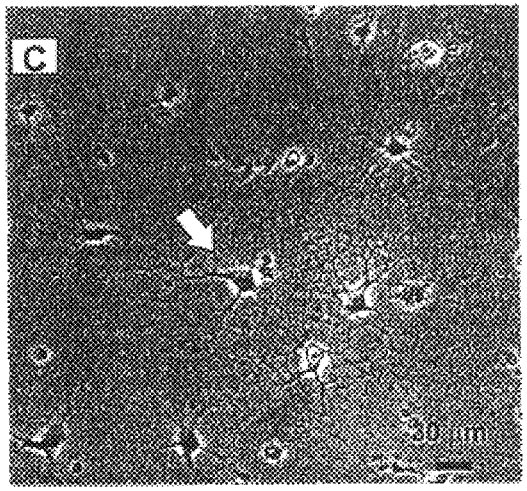

By 13 DIV, phase contrast microscopy revealed increasing numbers of cells with three to four processes emanating from the cell body. FIGS. 1B and 1C present phase contrast images of the cells. The white arrows in the figures mark typical examples. These cell bodies and processes of those cells were found to be immunoreactive for the antibodies CNPase-I and GC which have been shown to identify PROLs (Knapp, 1988; Ranscht, 1982). Cells with the multiple processes did not immunoreact for the A2B5 antibody or for antibodies to MBP. By 14 and 15 DIV, the PROLs constituted a major proportion of the cells in the cultures.

Figure 1D:
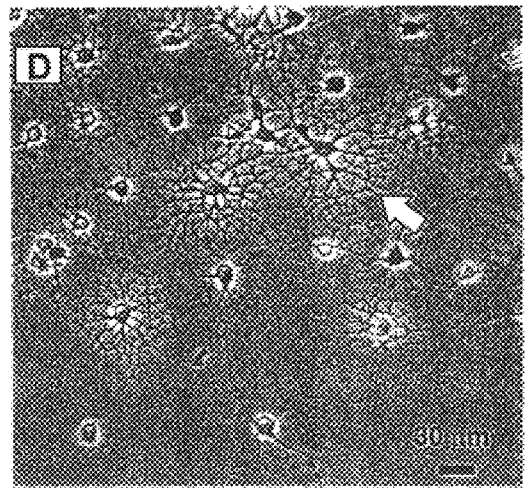
Figure 2D:
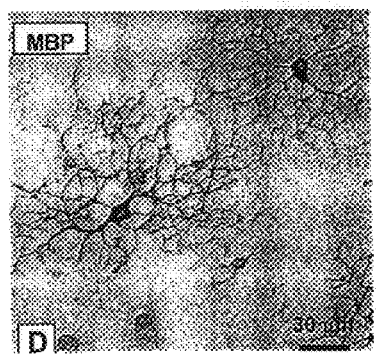
Figure 2E:
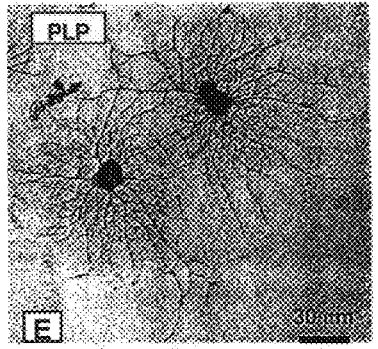

By 15 and 16 DIV, the PROLs elaborated more complex processes. These cells were highly branched and had 6 to 8 main processes. As shown by the typical cell marked by the white arrow in FIG. 1D, the interlacing small secondary and tertiary processes gave the processes a web-like appearance. Cells with the web-like processes were immunopositive for MBP (shown in FIG. 2D) and PLP (shown in FIG. 2E). MBP (Lees, 1984) and PLP (Bartlett et al., 1988) have been shown to be markers for OLs. The MBP expression could be seen in the oligodendroglial processes as well as in the cell body. An intense staining of PLP was found in the cell body. Some of the MBP positive cells were also found to have flat MBP positive membranes attached to the web-like processes.

Figure 2F:
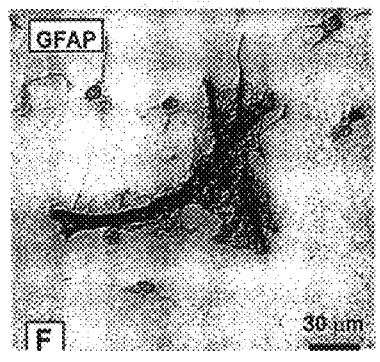
Figure 4A:
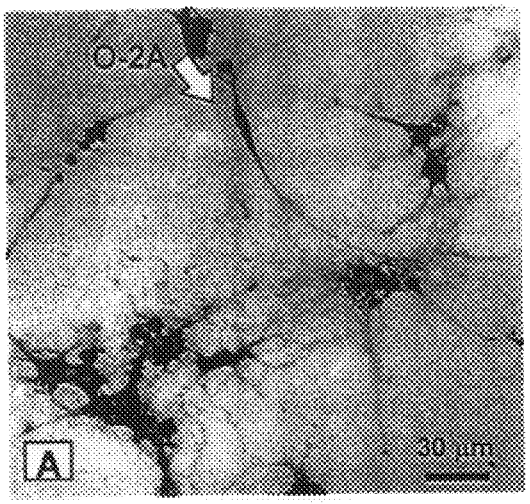
FIG. 4: Morphological identification of the oligodendroglial cells identified by methylene blue staining. 0-2As exhibit a typical bipolar morphology with two long thin processes extending from the cell body (A) while the PROL show a multipolar appearance with 3–5 processes (B). A complex network of secondary and tertiary processes branching off form the primary process characterizes OLs (C). AST display a flattened morphology with a larger cell body and nucleus compared to 0-2As, PROLs and OLs (D).
Figure 4B:
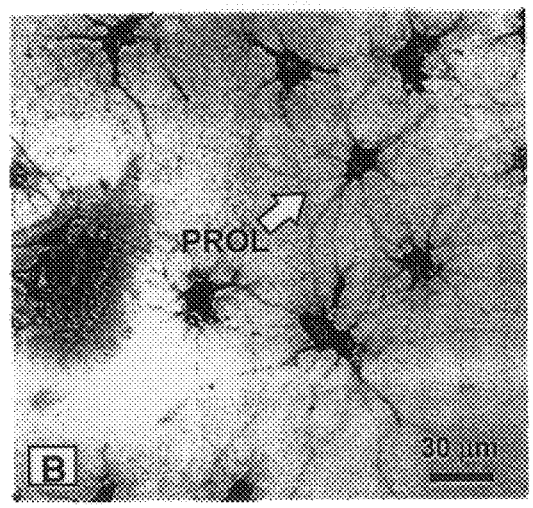
Figure 4C:
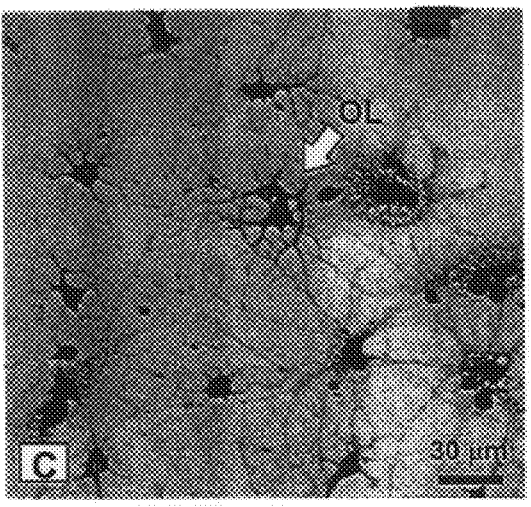
Figure 4D:
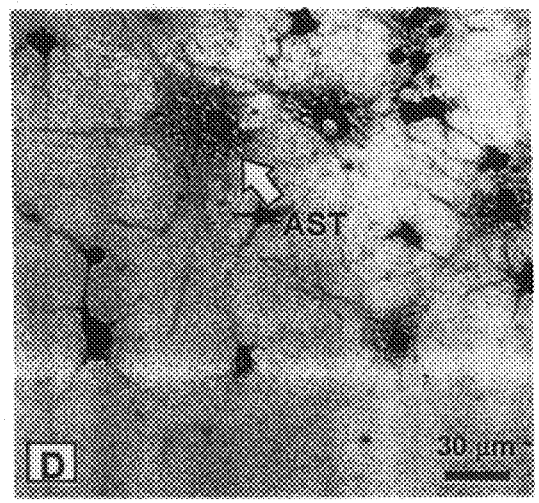

A small proportion of cells displayed a flattened morphology with a large round nucleus. These cells immunoreacted to the antibody glial fibrillary acidic protein (GFAP) as shown in FIG. 2F. The cells also possessed GFAP positive reticulated somal areas. These observations led to the identification of the GFAP positive cells as ASTs (Raff et al., 1979). Less than 1% of the cells in culture showed a non-process bearing amoeboid morphology and were identified as microglia.

Typically, 16 DIV culture comprised of 4% AST, 2% O-2A, 32% PROL and 62% OL (see FIG. 5 below). Since the differentiated PROL and OLs accounted for more than 93% of the total cells at 16 DIV, all the experiments reported in this thesis used 16 DIV cultures. The progressive increase in OLs and PROLs and the progressive decrease in O-2As between DIV 12 and 16 and the small numbers of ASTs at 16 DIV showed that the base media, with IGF-I and insulin added, favored the differentiation of O-2As along the oligodendrocyte pathway rather than along the type 2 astrocyte pathway. The methods reliably provided large number of identifiable PROLs and OLs at 16 DIV. The studies of apoptosis were therefore carried out at 16 DIV.

3.2 Decreased Survival of Oligodendroglial Cells after Insulin and IGF-I Withdrawal Cultures on 16 DIV were washed free of serum, insulin and IGF-I. The wash media was then replaced with BM. Control cultures were placed in IM. The washing and replacement with defined media served to suddenly withdraw IGF-I and insulin from the cells. The cells were exposed to either BM or IM for a 24 h period after which cell survival was estimated using counts of intact nuclei. Two independent series of experiment were carried out at different plating densities.

3.2.1 Counts Of Intact Nuclei

IGF-I and insulin withdrawal resulted in a decrease in numbers of intact nuclei at 24 h after washing. In experimental series-I (plating density of $5.3 \times 10^3$ cell/mm$^2$), counts of intact nuclei decreased to 54.8% (bar labeled BM in FIG. 3A1) compared to the intact nuclear counts for cells that were washed and replaced in media with IGF-I and insulin (bar labeled IM in FIG. 3A1). A similar decrease to 51.4% was observed in experimental series-II (plating density of $15.8 \times 10^3$ cell/mm$^2$) as shown by the bars labeled IM and BM in FIGS. 3A2. Table 1 presents the statistical probabilities for experimental series I and II. Each experimental series for the total intact cell counts consisted of three or four independent experiments.

Figures 1, 14A:
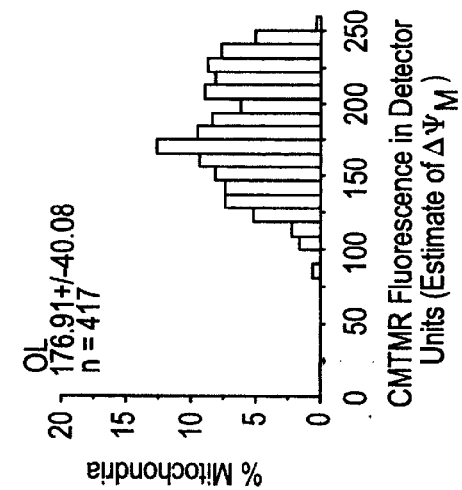
Figures 2, 14A:
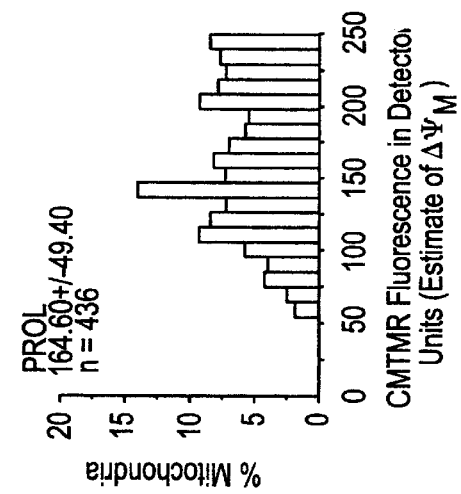
Figures 3, 14A:
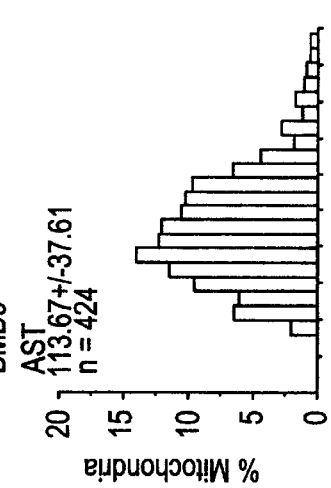
FIG. 3: Withdrawal of insulin and IGF-I decreases the number of intact nuclei and intact cells. (-)-Deprenyl increased the survival of oligodendrocytes in a serum free, insulin and IGF-I deprived base medium (BM). After 16 DIV, cells were washed and incubated in BM or BM supplemented with $10^{-9}$ M (-)-deprenyl (BM-D9) for 24 h. For controls, washed cells were replaced in media (IM) containing insulin (5 μg/ml) and IGF-I (2.5 ng/ml) or IM supplemented with $10^{-9}$ M (-)-deprenyl (IM-D9). Intact nuclei were counted using a haemocytometer after Zap-oglobin lysis. Total cell numbers indicate counts of intact methylene blue stained cells by a random method (see Materials and Methods). Data shown are mean percentage+SEM of nuclei (A1, A2) or cells (B1, B2) relative to IM counted in two experimental series in which the cells were grown at seeding densities of $5.3 \times 10^3$ cells/cm$^2$ (experimental series-I) and $15.8 \times 10^3$ cells/cm$^2$ (experimental series-II).
Figures 1, 14B:
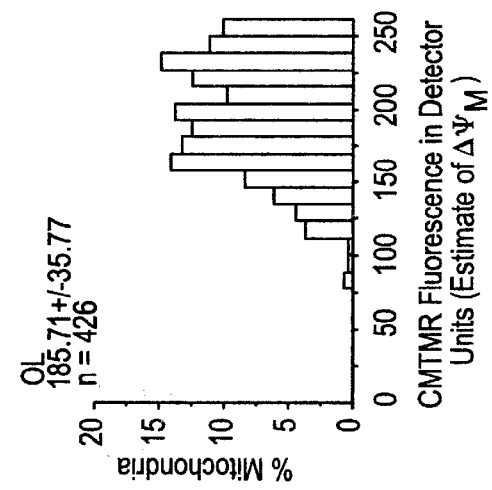
Figures 2, 14B:
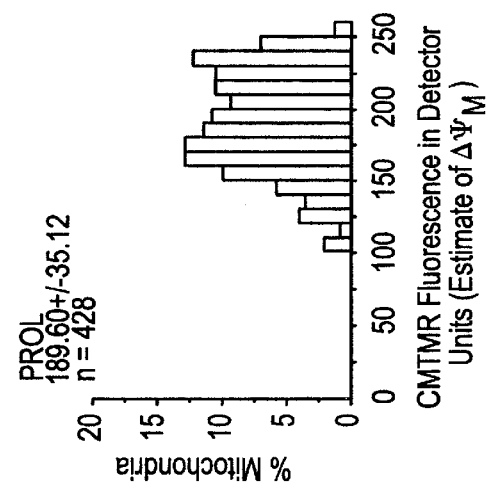
Figures 3, 14B:
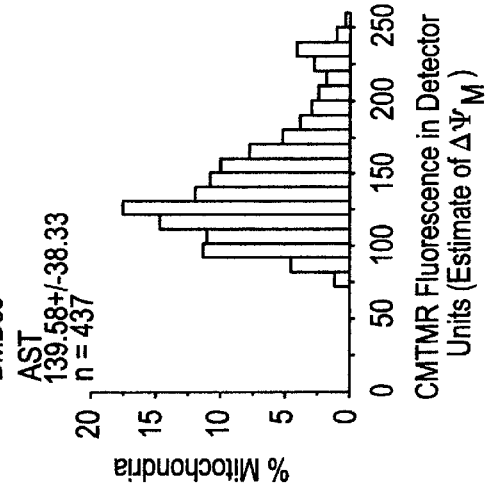

Experiments were carried out to determine whether (−)-deprenyl altered the reduction in the counts of intact nuclei induced by IGF-I and insulin withdrawal. After washing and placement in insulin and IGF-I free media supplemented with $10^{-9}$ M (−)-deprenyl (bars labeled BM-D9 in FIG. 3A1), the numbers of intact nuclei were 119% of those in IM in experimental series-I so that (−)-deprenyl increased the number of cells after IGF-I and insulin withdrawal by 217% (compare bars labeled BM-D9 and BM in FIG. 3A1). The BM decrease to 84.45% of IM was smaller in experimental series-II but BM-D9 still showed an increase of 164% compared to BM (compare BM and BM-D9 bars in FIG. 3A2). When cells were placed in IM with $10^{-9}$ M (−)-deprenyl (IM-D9 bars), the number of intact nuclei were 135.6% compared to IM in experimental series-I) and 102.4% compared to IM for experimental series-II (FIG. 3A2).

According to the counts of intact nuclei, treatment with $10^{-9}$ M (−)-deprenyl induced a significant increase in numbers of intact nuclei both for cells washed and replaced in media with IM and those washed and placed in BM (see table 1).

TABLE 1

Statistical testing of data for intact nuclear and cell counts

| Experimental Series - I | | | Experimental series - II | | |
|---|---|---|---|---|---|
| Treatment | Intact nuclear counts | Intact cell counts | Treatment | Intact nuclear counts | Intact cell counts |
| T-test for independent samples | | | T-test for independent samples | | |
| IM-D9/IM | $1.9 \times 10^{-5}$ | $1.0 \times 10^{-1}$ | IM-D9/IM | $5.3 \times 10^{-1}$ | $3.2 \times 10^{-3}$ |
| BM/IM | $1.1 \times 10^{-13}$ | $4.8 \times 10^{-10}$ | BM/IM | $1.2 \times 10^{-7}$ | $2.1 \times 10^{-17}$ |
| BM-D9/IM | $2.8 \times 10^{-4}$ | $6.5 \times 10^{-1}$ | BM-D9/IM | $9.9 \times 10^{-5}$ | $9.5 \times 10^{-1}$ |
| BM-D9/BM | $1.4 \times 10^{-13}$ | $5.9 \times 10^{-14}$ | BM-D9/BM | $4.7 \times 10^{-7}$ | $2.1 \times 10^{-16}$ |
| Mann - Whitney U test | | | Mann - Whitney U test | | |
| IM-D9/IM | $1.1 \times 10^{-5}$ | $1.4 \times 10^{-3}$ | IM-D9/IM | $3.9 \times 10^{-1}$ | $2.0 \times 10^{-2}$ |
| BM/IM | $1.3 \times 10^{-8}$ | $1.4 \times 10^{-4}$ | BM/IM | $6.6 \times 10^{-4}$ | $4.9 \times 10^{-11}$ |
| BM-D9/IM | $7.1 \times 10^{-5}$ | $9.4 \times 10^{-2}$ | BM-D9/IM | $1.3 \times 10^{-3}$ | $6.7 \times 10^{-1}$ |
| BM-D9/BM | $1.3 \times 10^{-8}$ | $7.8 \times 10^{-10}$ | BM-D9/BM | $1.6 \times 10^{-4}$ | $3.7 \times 10^{-9}$ |

The increase in numbers of intact nuclei for cells that were washed and replaced in media with IM was compatible with two interpretations: 1) that (−)-deprenyl induced the increased number of intact nuclei in cells that were washed and placed in media BM by increasing the replication rates of the cells, and 2) that (−)-deprenyl decreased the death of the cells caused by IGF-I and insulin withdrawal and also decreased a baseline death process that was present in cells washed and replaced in IM.

3.2.2 Total Counts of Methylene Blue Stained Cells

The counting of methylene blue stained cells plated on coverslips resulted in data, which paralleled that found for counts of intact nuclei above. In experimental series-I, washing and placement of cells in BM (bar labeled BM in FIG. 3B1) decreased in the intact cell counts of 16.2% with respect to cells that were washed and replaced in media IM (bar labeled IM in FIG. 3B1). Similarly, the BM intact cell counts decreased to 39.4% of IM in experimental series-II (FIG. 3B2). Similar to the intact cell counts, treatment with (−)-deprenyl (BM-D9) increased the number of intact methylene blue stained cells to 576% of those in BM in experimental series-I (FIG. 3B1) and 255% of those in BM in experimental series-II (FIG. 3A2).

Figures 1, 6A:
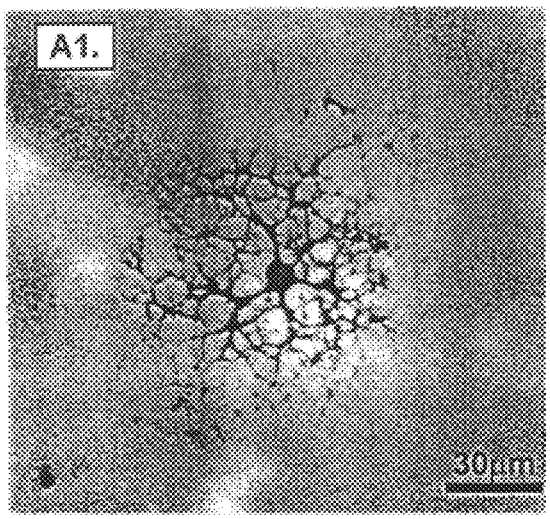
Figures 1, 6B:
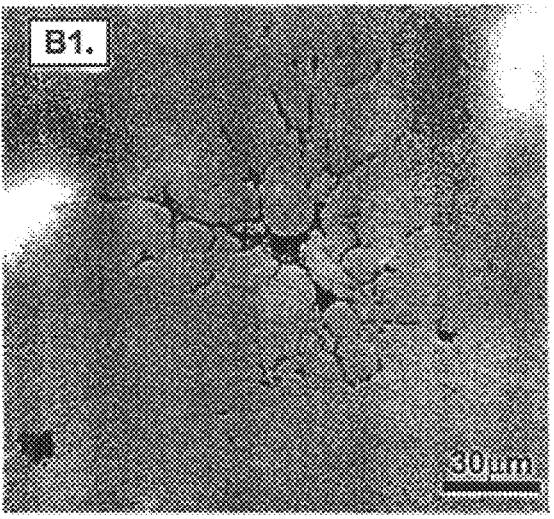
Figures 2, 6A:
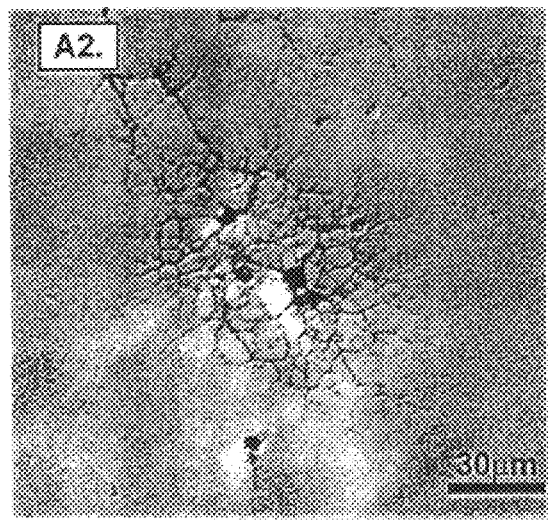
Figures 2, 6B:
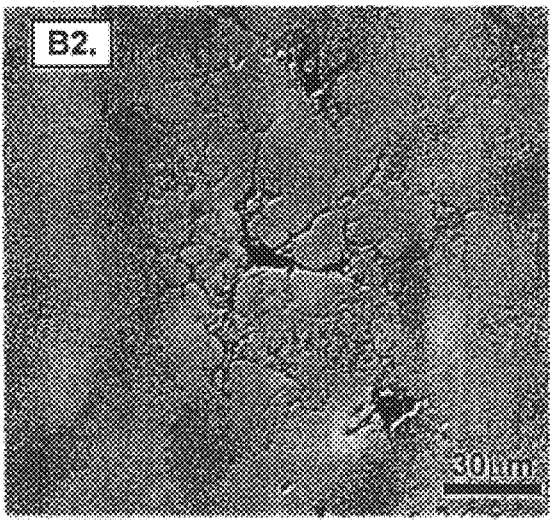

The number of intact methylene blue stained cells in IM-D9 were 128.9% (experimental series-I) and 130.6% (experimental series-II) relative to IM (FIGS. 3B1, and 3B2). The data obtained from the intact nuclear counts and cell counts showed that (−)-deprenyl increased the numbers of oligodendroglial cells when administered in combination with either BM or IM. Like the data for counts of intact nuclei, the changes induced by (−)-deprenyl could result from an increase in replication or a decrease in cell death.

3.2.3 Intact Cell Counts for Individual Cell Types in Cultures

The characteristic morphologies for the O-2A, PROL, OL and AST cells as revealed by immunocytochemical identification above allowed the identification of the cell types on methylene blue stained coverslips. FIGS. 4A–D shows typical methylene blue stained O-2A, PROL, OL and AST cell types.

Figure 5A:
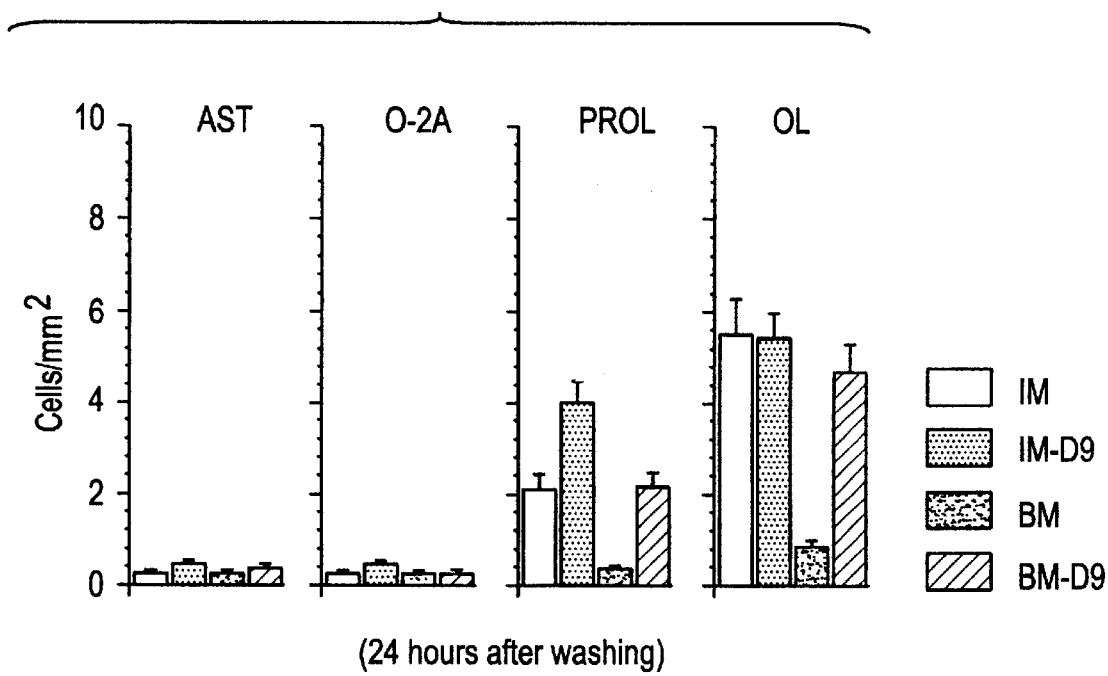
FIG. 5: Effects of insulin and IGF-I withdrawal and treatment with R(-)-deprenyl on oligodendroglial cell numbers. Cells grown on coverslips on 16 DIV were incubated in BM, BM-D9, IM or IM-D9 for 24 hours. After the treatment period cells were stained with 1% methylene blue solution containing 1% AgNO$_3$. Methylene blue stained positive cell types were morphologically identified as 0-2As, PROLs, OLs or AST and counted in 25 randomly chosen 100 power fields on triplicate coverslips. Results are expressed as mean+SEM of experiments series-I (A) and experimental series-II (B).
Figure 5B:
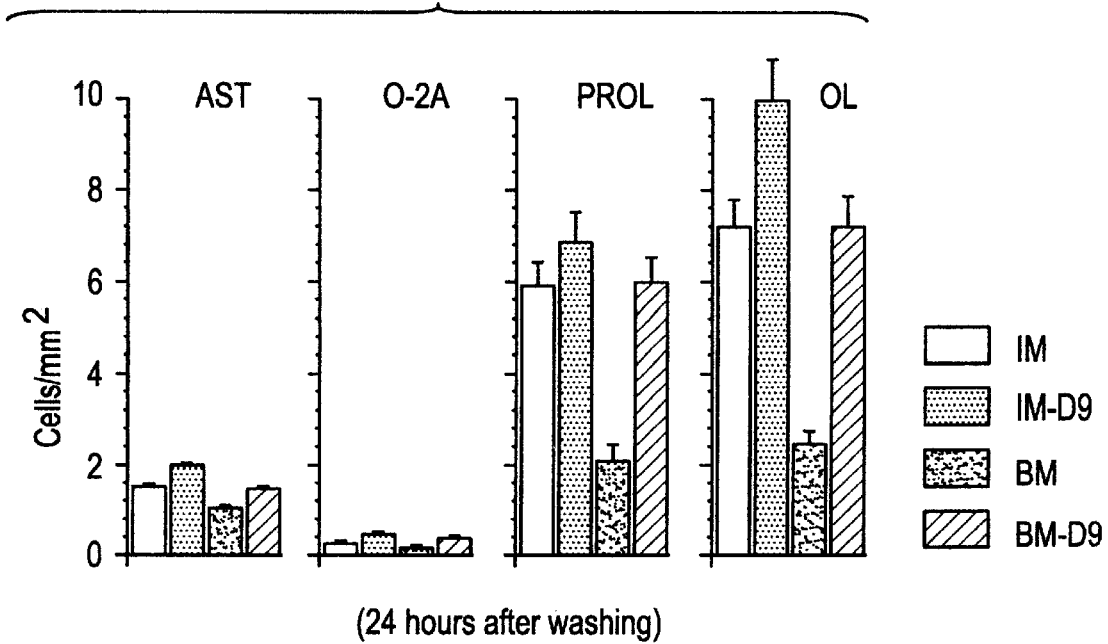

On washing and placement in BM, the counts of all four cell types showed a significant reduction in numbers (see FIG. 5). In experimental series-I, the numbers for BM, when compared to IM, were 30.3%, 69.2%, 14.0%, 15.1% for ASTs, O-2As, PROLs and OLs respectively (FIG. 5A). As above for the total cell counts, relatively less cell death was observed in experimental series-II. The survival in BM compared to IM for experimental series-II was 71.2%, 42.2%, 37.3%, 35.0% for ASTs, O-2As, PROLs and OLs respectively (FIG. 5B). Note that among the four cell populations, maximum decreases in numbers were seen in the more differentiated PROL and OL cells. (−)-Deprenyl increased the numbers of all the four types of cells in the IGF-I and insulin withdrawn cultures. For BM-D9, cell numbers increased compared to those in BM to 570% for ASTs, 244% for O-2As, 739.2% for PROLs and a 565.0% for OLs in experimental series-I (FIG. 5A) and to 132% for ASTs, 176% for O-2As, 275% for PROLs and 291% for OLs for experimental series II (FIG. 5B).

TABLE 2

Statistical testing of data for counts of individual cell types

| | Experimental Series - I | | | | | Experimental Series - II | | | |
|---|---|---|---|---|---|---|---|---|---|
| | T-test for independent samples | | | | | T-test for independent samples | | | |
| Treatment | AST | O-2A | PROL | OL | Treatment | AST | O-2A | PROL | OL |
| IM-D9/IM | $4.2 \times 10^{-3}$ | $1.1 \times 10^{-2}$ | $7.2 \times 10^{-4}$ | $9.5 \times 10^{-1}$ | IM-D9/IM | $2.1 \times 10^{-4}$ | $1.0 \times 10^{-2}$ | $5.9 \times 10^{-2}$ | $1.1 \times 10^{-3}$ |
| BM/IM | $8.9 \times 10^{-3}$ | $5.0 \times 10^{-1}$ | $1.0 \times 10^{-6}$ | $6.0 \times 10^{-9}$ | BM/IM | $1.5 \times 10^{-4}$ | $2.7 \times 10^{-4}$ | $3.2 \times 10^{-1}$ | $1.3 \times 10^{-12}$ |
| BM-D9/IM | $5.8 \times 10^{-2}$ | $2.3 \times 10^{-1}$ | $8.6 \times 10^{-1}$ | $3.1 \times 10^{-1}$ | BM-D9/IM | $4.5 \times 10^{-1}$ | $1.2 \times 10^{-1}$ | $8.1 \times 10^{-1}$ | $8.6 \times 10^{-1}$ |
| BM-D9/BM | $7.0 \times 10^{-6}$ | $5.4 \times 10^{-2}$ | $2.7 \times 10^{-9}$ | $3.0 \times 10^{-12}$ | BM-D9/BM | $1.6 \times 10^{-3}$ | $1.3 \times 10^{-2}$ | $1.3 \times 10^{-12}$ | $1.1 \times 10^{-12}$ |
| | Mann-Whitney U Test | | | | | Mann-Whitney U Test | | | |
| Treatment | AST | O-2A | PROL | OL | Treatment | AST | O-2A | PROL | OL |
| IM-D9/IM | $2.7 \times 10^{-2}$ | $8.6 \times 10^{-2}$ | $1.3 \times 10^{-3}$ | $6.5 \times 10^{-1}$ | IM-D9/IM | $5.5 \times 10^{-5}$ | $2.4 \times 10^{-2}$ | $3.3 \times 10^{-2}$ | $3.5 \times 10^{-3}$ |
| BM/IM | $1.0 \times 10^{-1}$ | $9.3 \times 10^{-1}$ | $5.7 \times 10^{-4}$ | $4.8 \times 10^{-7}$ | BM/IM | $3.6 \times 10^{-4}$ | $5.9 \times 10^{-3}$ | $4.2 \times 10^{-1}$ | $2.1 \times 10^{-11}$ |
| BM-D9/IM | $4.5 \times 10^{-2}$ | $3.1 \times 10^{-1}$ | $5.3 \times 10^{-1}$ | $6.7 \times 10^{-1}$ | BM-D9/IM | $4.5 \times 10^{-1}$ | $3.1 \times 10^{-1}$ | $8.1 \times 10^{-1}$ | $9.6 \times 10^{-1}$ |
| BM-D9/BM | $1.0 \times 10^{-4}$ | $2.5 \times 10^{-1}$ | $9.7 \times 10^{-8}$ | $9.5 \times 10^{-9}$ | BM-D9/BM | $3.1 \times 10^{-3}$ | $6.5 \times 10^{-2}$ | $4.0 \times 10^{-11}$ | $6.7 \times 10^{-10}$ |

For IM-D9, the numbers of cells relative to those for IM were 227% for AST, 315% for O-2As, 196% for PROLs and 99% for OLs for experimental series-I (FIG. 6A). In experimental series-II, IM-D9 cell numbers relative to IM were 132% for AS, 160% for O-2As, 120% for PROLs and 140% for OLs for experimental series-II (FIG. 5B). Table 2 summarizes the statistical probabilities.

3.3 Oligodendroglial Cell Death on Withdrawal of Insulin and IGF-I 3.3.1 Morphological Changes After washing and placement in BM, the web-like processes of OLs underwent fragmentation. FIG. 6 show typical transmission (A1 and B1) interference contrast images (A2 and B2) of OLs at 18 h after washing that were immunoreacted for MBP. A1 and A2 are for cells that were washed and replaced in IM while B1 and B2 are for cells that were washed and placed in media only. B1 and B2 show the fragmentation of the OL processes with relative maintenance of cell body structure. The process fragmentation was noted increasing after 6 h following IGF-I and insulin withdrawal.

3.3.2 Evidence For Apoptotic Degradation after IGF-I and Insulin Withdrawal

Figure 7A:
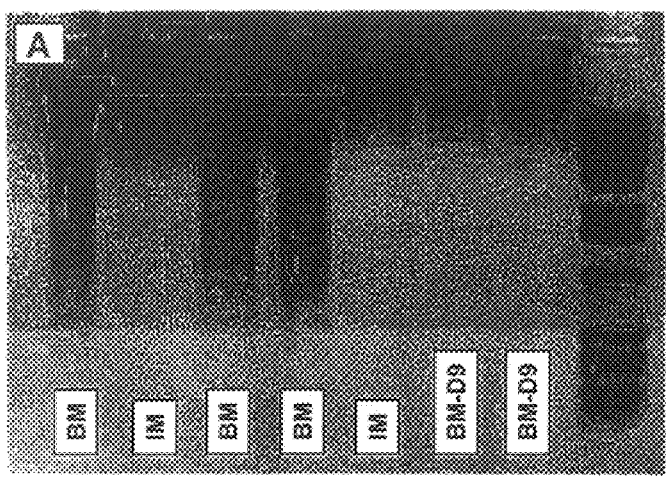
FIG. 7: Apoptosis of PROLs and OLs on IGF-I and insulin withdrawal. Panel (A) shows the internucleosomal DNA degradation of PROLs and OLs. DNA "ladders" showing internucleosomal DNA digestion can be observed when cells were placed in BM for 18 h after washing. The ladder pattern is not seen when cells were incubated in IM or BM-D9. Panel (B) shows the nuclear DNA cleavage of apoptotic oligodendrocytes. Insulin and IGF-I withdrawn cells were stained for free 3' ends of cut DNA using the Apop Tag™ method (see Materials and Methods). Inset in panel (B) shows apoptotic OLs. The apoptotic nuclei typically show pyknosis and DNA fragmentation. Panel (C) shows an interference contrast micrograph of an apoptotic OL, as revealed by the Apop Tag method, displaying shrinkage of the cell body and fragmentation of processes. Panels (D1) and (D2) show fluorescence photomicrographs of PROLs and OLs deprived of insulin and IGF-I for 18 hours and stained with Hoechst 33258. Apoptotic cells show bright, condensed chromatin (open arrows) while non-apoptotic cells show nuclei with diffuse and granular pattern of staining (white arrows). Panel (D1) also shows an intensely fluorescent lobular structure (empty arrow) characteristic of an apoptotic body.

Electrophoresis gels for DNA extracted from the cells at 18 h after washing on 16 DIV showed DNA ladders with a period of about 180 bp for BM while electrophoresis for IM and BM-D9 did not show detectable laddering (FIG. 7A).

Figure 7B:
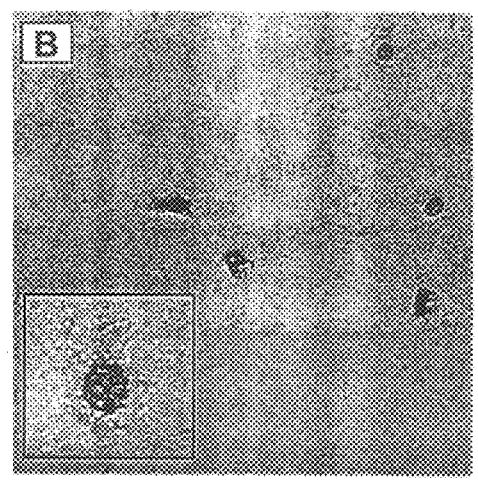
Figure 7C:
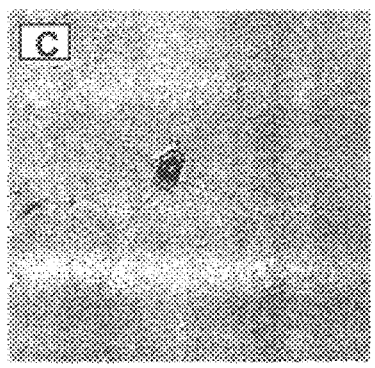
Figures 1, 7D:
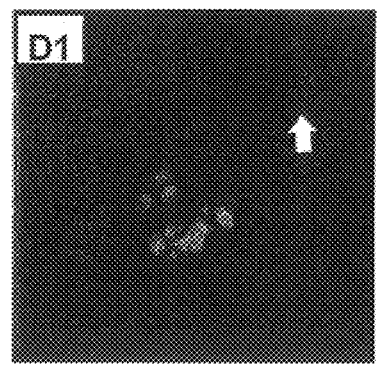
Figures 2, 7D:
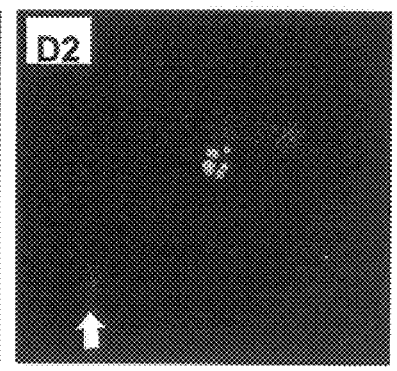
Figure 8A:
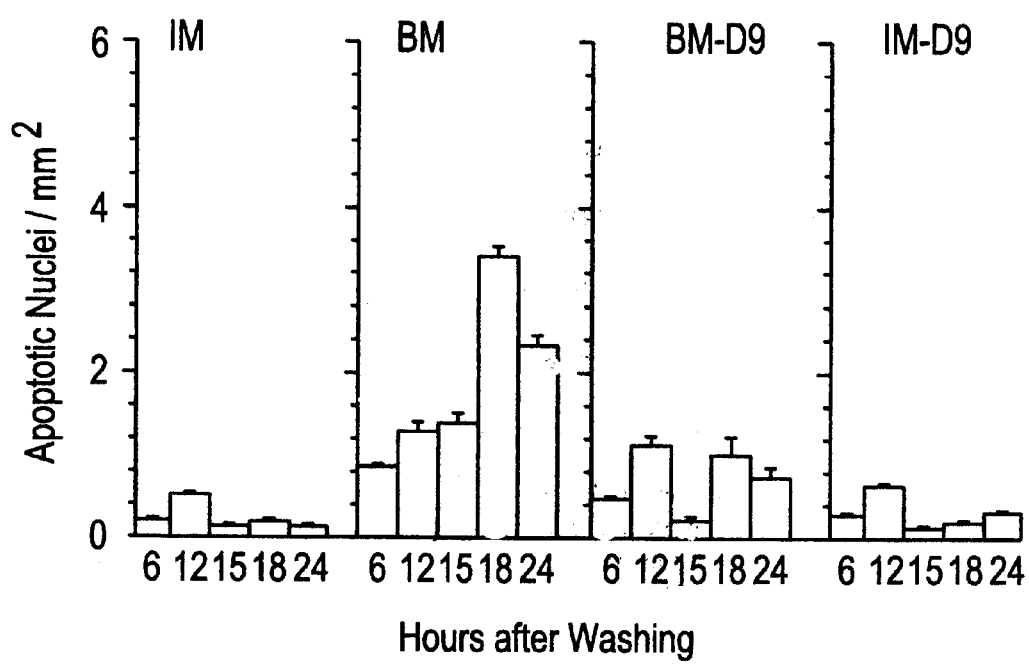
FIG. 8: Time course of apoptotic death of PROLs and OLs. Oligodendroglial cultures grown on coverslips at 16 DIV were incubated in IM/BM/BM-D9 or IM-D9 for 6, 12, 15, 18 and 24 h. Staining of fragmented nuclear DNA in OLs was performed using the Apop Tag method (see Materials and Methods). Apop Tag positive nuclei were counted in 25 randomly chosen 100 power fields on triplicate coverslips. Data from experimental series I and II (A and B) are expressed as mean number+SEM of apoptotic nuclei/mm2. Note the occurrence of apoptotic nuclei after 6 h of trophic withdrawal, peaking at 18 h. (−)-Deprenyl reduced the incidence of apoptotic nuclei at all the time points after IGF-I and insulin withdrawal.
Figure 8B:
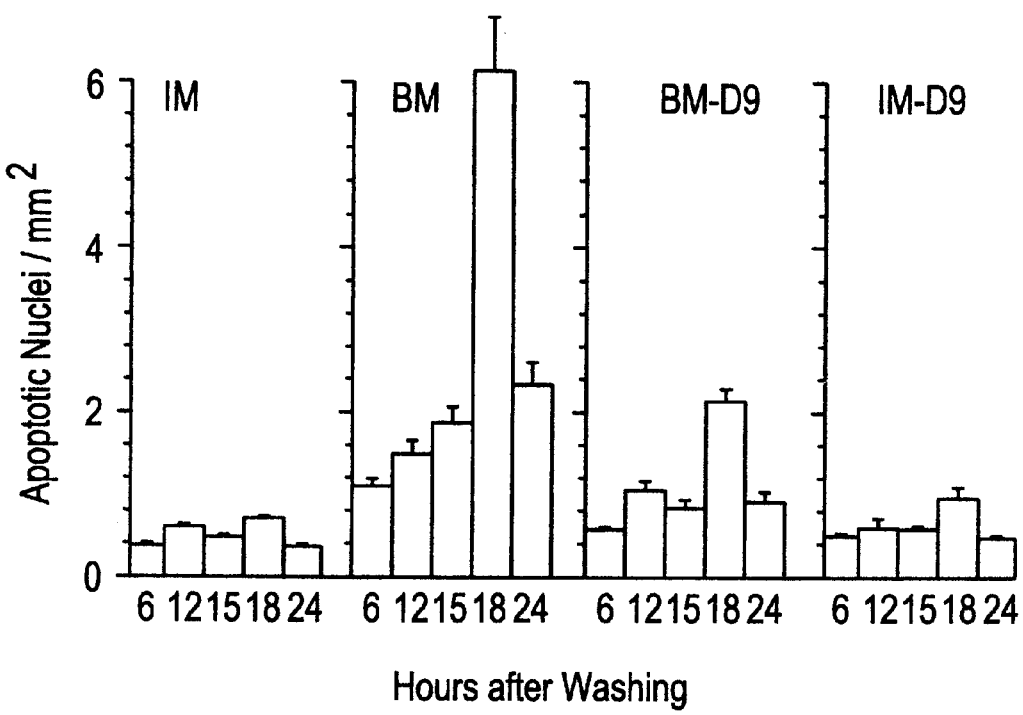

Staining of the oligodendroglial cells with a supravital, bisbenzimide dye, Hoechst 33258 revealed nuclear chromatin condensation and typical apoptotic bodies (see fluorescence images in FIGS. 7D1 and 7D2 for BM at 18 hours after washing, apoptotic bodies and condensed DNA are marked by open arrows while normally staining nuclei are marked by the white arrows). The Hoechst 33258 staining was identical to that which our laboratory found in neuronally differentiated PC 12 cells after serum and NGF withdrawal (see (Wadia et al., 1998)).

Similarly in situ end labeling (ISEL) using the ApopTag™ method revealed a proportion of nuclei in both BM and IM with evidence for DNA fragmentation as shown in the FIGS. 7B and 7C (the images are for cells in BM at 18 hours after washing). Taken together the DNA ladders, chromatin staining and ISEL indicated that a significant proportion of the cells died by the process of apoptosis and the apoptosis was more evident after IGF-I and insulin withdrawal than it was for cells supported by IGF-I and insulin.

3.3.3 Time Course and Magnitude of Apoptotic Nuclear Changes

Counts of ApopTag™ positive nuclei were obtained for 5 of the time points after washing to determine the time course of the appearance of apoptotic nuclear degradation in the cultures. Significant numbers of ApopTag™ positive nuclei were found are all time points for cells in IM (2.3% and 3.4% of total intact cell counts/mm² for the two series respectively). This finding indicated a baseline level of apoptosis in the cultures supported by IGF-I and insulin. A significant level of baseline apoptosis has been found in most neural culture systems (see (Wadia et al., 1998)). The baseline level therefore must be taken into accord when judging the effect of agents that promote or reduce apoptosis. Addition of $10^{-9}$M (−)-deprenyl to the IM did not significantly change the number of ApopTag™ positive nuclei at any time point in either experimental series.

Withdrawal of IGF-I and insulin induced a gradual but marked increase in the number of ApopTag™ nuclei that reached a maximum at 18 hours after washing. Comparison of the values at each time point for BM and IM shows that the withdrawal of IGF-I and insulin markedly increased the number of ApopTag™ nuclei above the baseline values found for IM. Addition of $10^{-9}$M (−)-deprenyl to the base media, significantly decreased the numbers of ApopTag™ nuclei in both experimental series (see table 3 for statistical probabilities). These data clearly establish that the cultured oligodendroglial cells die by apoptosis after IGF-I and insulin withdrawal and that (−)-deprenyl significantly reduces that apoptosis. It establishes that the increase in numbers of intact nuclei and methylene blue stained cells resulted at least in part from an anti-apoptotic action of (−)-deprenyl.

TABLE 3

Statistical analysis of data for time course of apoptosis of oligodendroglial cells

| Experimental series - I | | | | | | Experimental series - II | | | | | |
|---|---|---|---|---|---|---|---|---|---|---|---|
| T-test for independent samples | | | | | | T-test for independent samples | | | | | |
| Treatment | 6 h | 12 h | 15 h | 18 h | 24 h | Treatment | 6 h | 12 h | 15 h | 18 h | 24 h |
| IM-D9/M | $4.8 \times 10^{-1}$ | $1.8 \times 10^{-1}$ | 1.0 | $8.4 \times 10^{-1}$ | $1.6 \times 10^{-1}$ | IM-D9/IM | $3.5 \times 10^{-1}$ | $7.7 \times 10^{-1}$ | $7.8 \times 10^{-2}$ | $2.0 \times 10^{-1}$ | $7.4 \times 10^{-1}$ |
| BM/IM | $1.9 \times 10^{-7}$ | $2.2 \times 10^{-4}$ | $1.0 \times 10^{-13}$ | $1.3 \times 10^{-8}$ | $1.2 \times 10^{-5}$ | BM/IM | $1.5 \times 10^{-9}$ | $1.7 \times 10^{-5}$ | $4.5 \times 10^{-8}$ | $7.5 \times 10^{-10}$ | $3.8 \times 10^{-12}$ |
| BM-D9/M | $2.5 \times 10^{-4}$ | $5 \times 10^{-6}$ | $2.3 \times 10^{-1}$ | $1.3 \times 10^{-4}$ | $9.0 \times 10^{-4}$ | BM-D9/IM | $2.2 \times 10^{-2}$ | $1.8 \times 10^{-3}$ | $3.6 \times 10^{-2}$ | $3.7 \times 10^{-8}$ | $2.0 \times 10^{-4}$ |
| BM-D9/BM | $8.4 \times 10^{-4}$ | $3.8 \times 10^{-1}$ | $1.7 \times 10^{-12}$ | $3.5 \times 10^{-5}$ | $5 \times 10^{-6}$ | BM-D9/BM | $2.0 \times 10^{-6}$ | $3.6 \times 10^{-2}$ | $3.4 \times 10^{-5}$ | $2.4 \times 10^{-8}$ | $3.2 \times 10^{-7}$ |
| Mann-Whitney U Test | | | | | | Mann-Whitney U Test | | | | | |
| Treatment | 6 h | 12 h | 15 h | 18 h | 24 h | Treatment | 6 h | 12 h | 15 h | 18 h | 24 h |
| IM-D9/IM | $7.9 \times 10^{-1}$ | $4.9 \times 10^{-1}$ | $7.6 \times 10^{-1}$ | $9.9 \times 10^{-1}$ | $3.9 \times 10^{-1}$ | IM-D9/IM | $3.4 \times 10^{-1}$ | $2.3 \times 10^{-1}$ | $8.3 \times 10^{-1}$ | $5.4 \times 10^{-1}$ | $7.9 \times 10^{-1}$ |
| BM/IM | $4.6 \times 10^{-5}$ | $1.3 \times 10^{-2}$ | $6.2 \times 10^{-13}$ | $2.2 \times 10^{-10}$ | $1.2 \times 10^{-5}$ | BM/IM | $5.9 \times 10^{-8}$ | $3.0 \times 10^{-3}$ | $4.0 \times 10^{-6}$ | $2.1 \times 10^{-10}$ | $7.2 \times 10^{-9}$ |
| BM-D9/IM | $1.1 \times 10^{-3}$ | $2.0 \times 10^{-5}$ | $4.3 \times 10^{-1}$ | $3.0 \times 10^{-3}$ | $1.6 \times 10^{-3}$ | BM-D9/IM | $2.8 \times 10^{-2}$ | $6.7 \times 10^{-3}$ | $2.4 \times 10^{-1}$ | $1.1 \times 10^{-7}$ | $3.4 \times 10^{-3}$ |
| BM-D9/BM | $1.3 \times 10^{-2}$ | $7.8 \times 10^{-1}$ | $7.9 \times 10^{-12}$ | $1.0 \times 10^{-5}$ | $7.3 \times 10^{-4}$ | BM-D9/BM | $5.3 \times 10^{-5}$ | $8.2 \times 10^{-2}$ | $4.4 \times 10^{-4}$ | $2.9 \times 10^{-5}$ | $7.1 \times 10^{-5}$ |

3.4 (−)-Deprenyl But Not (+)-Deprenyl Increases Oligodendroglial Survival

Figure 9:
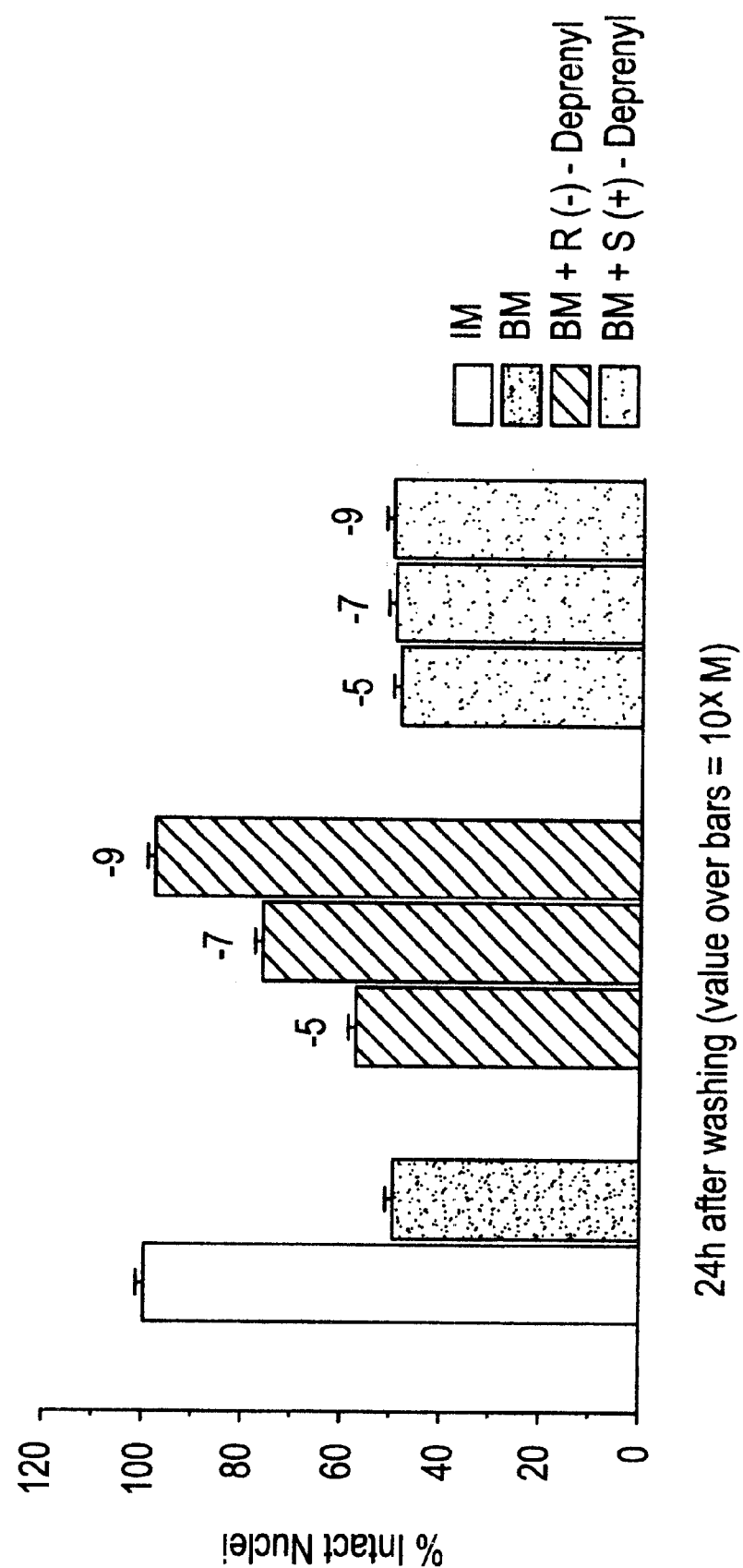
FIG. 9: Concentration-survival relationship on treatment with S (+) and R (−)-deprenyl. After 16 DIV, cells were washed and incubated in BM or BM with $10^{-5}$M, $10^{-7}$M and $10^{-9}$M, S (+) or R (−)-deprenyl for 24 h. For controls, washed cells were replaced in IM. Intact nuclei were counted using a hemocytometer after Zap-oglobin lysis (see Materials and Methods). Data shown are mean percentage±SEM of intact nuclei relative to IM.

Studies in neuronally differentiated PC12 cells after serum and NGF withdrawal (Tatton et al., 1994) and immature facial neurons after axotomy (Ansari et al., 1993) showed that (−)-deprenyl decreased the apoptotic death of the cells while (+)-deprenyl did not have any effect on the survival of the cells. I examined the relative effects of the two enantiomers on oligodendroglial survival after IGF/insulin withdrawal at three different concentrations (see FIG. 9). The (−)-enantiomer induced a graded increase in the numbers of intact nuclei with the greatest increase for $10^{-9}$ M. The gradual decrease in cell numbers with increasing concentration from $10^{-9}$ to $10^{-5}$ M is similar to that found for neuronally differentiated PC12 cells after serum and NGF withdrawal (Tatton et al., 1994). In that model, (−)-deprenyl was also most effective in reducing apoptosis at $10^{-9}$ M.

In the oligodendroglial cells, the (+)-enantiomer did not alter the numbers of intact nuclei from the values found for BM for any of the three concentrations tested. Accordingly, these results indicate that the anti-apoptotic action of (−)-deprenyl on the oligodendroglial cells is stereospecific.

3.5 Alterations in the Levels of Proligodendrocyte and Oligodendrocyte Specific Marker Proteins To determine the changes in the levels of proteins specific to the PROLs and the OLs, Western blots were performed for protein extracts from cultures washed and placed in BM/IM/BM-D9/BM-Ds9/IM-D9 for 18 hours. Anti-MBP (OL marker), anti-PLP (OL marker), anti-GC (PROL marker) and anti-CNP (PROL marker) antibodies were used to determine the levels of the OL and PROL marker proteins.

The anti-MBP antibody recognized two distinct isoforms of myelin basic protein at 21 and 14 kDa. As shown in the Western blot labeled myelin basic protein in FIG. 10, the immunodensity of the 21 and 14 kDa bands for the BM sample were reduced compared to the IM sample indicating that withdrawal resulted in a decrease in the level of MBP. Since an equal amount of total protein was loaded into each of the lanes, the decrease indicates a decreased proportion of MBP in the sample. The decrease could result from a net decrease in OLs relative to other cell types in samples which would correspond, at least in part, to the greater proportional loss of PROLs and OLs than O2-A cells and AST cells shown above. It could also result from an induction of decreased expression of the MBP gene in response to IGF-I and insulin withdrawal.

Figure 10:
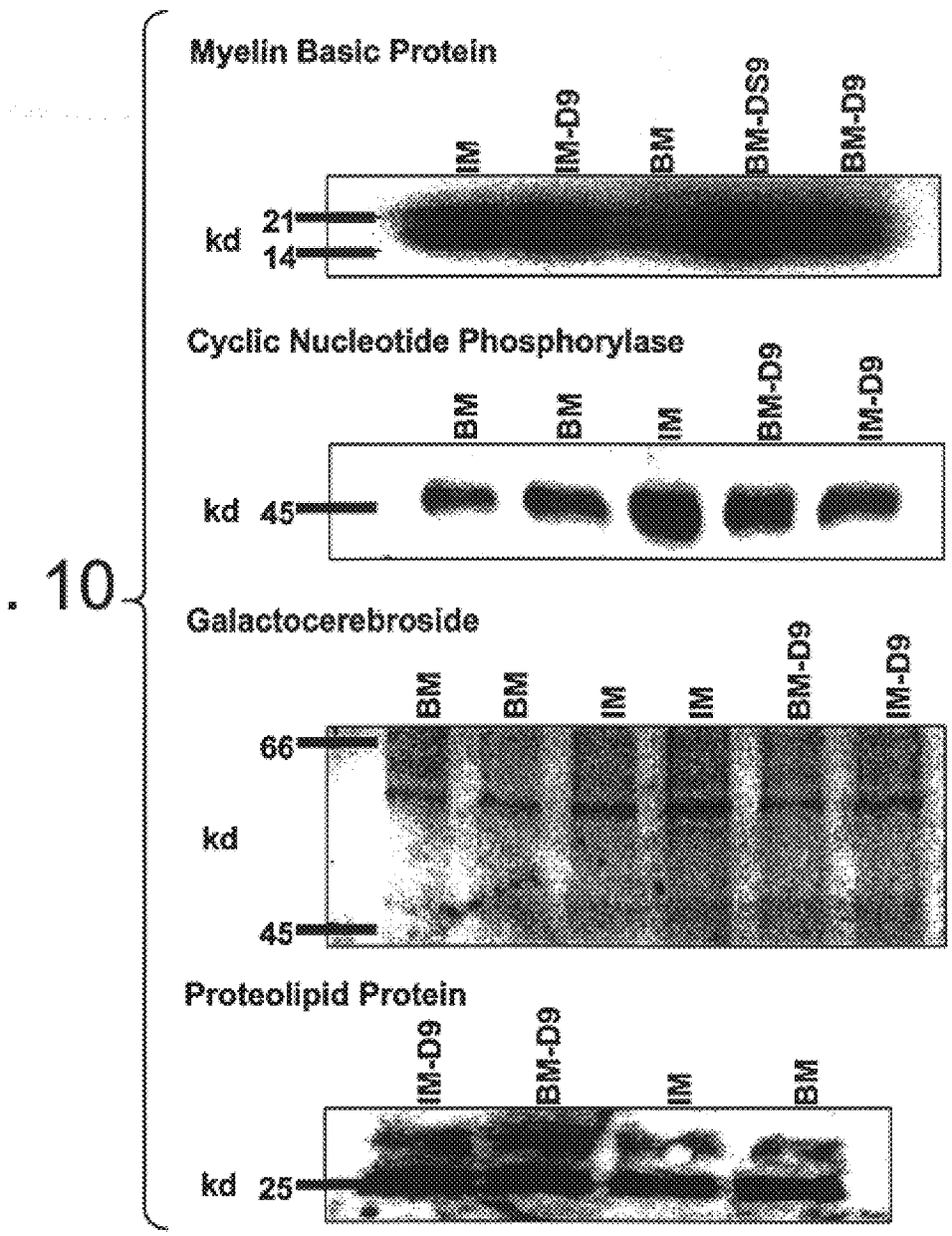
FIG. 10: Effects of insulin/IGF-I withdrawal and anti-apoptotic compounds on oligodendroglial protein levels. Total protein extracted from the cells placed in BM, IM, BM-D9/BM-Ds9 or IM-D9 for 18 h after washing. Western blot analysis of the proteins was performed and the blots were probed with antibodies to MBP, CNP, GC and PLP. MBP, CNP and GC show decreased immunodensity when placed in BM. (−)-Deprenyl as well as (−)-desmethyldeprenyl markedly increased the immunodensity of the proteins.

Probing of the blots for the second OL protein marker, PLP, revealed a visible 25 kDa band together with a faintly visible 30 kDa (Western blot labeled Proteolipid protein in FIG. 10). As in this example, there was no apparent change in the immunodensity for the anti-PLP antibody when the BM and IM samples were compared. A decrease in band density might be expected given the count data above that revealed a proportionally greater loss of PROLs than O-2As and ASTs. A decrease in band density due to decreased numbers of PROLs containing PLP may have been offset by an overall increase in PLP expression at the time of the samples.

Similar to MBP, both GC (see the distinct 60 kDa single band in the Western blot in FIG. 10 labeled galactocerebroside) and CNPase-I (see the distinct 45 kDa single bands in the Western blot in FIG. 9 labeled cyclic nucleotide phosphorylase) showed a decrease in immunodensity for BM compared to IM which indicates an effect of IGF-I and insulin withdrawal on PROLs.

The dramatic findings on the western blots were provided by the treatment of the IGF-I/insulin withdrawn cells with $10^{-9}$ M (−)-deprenyl (lanes labeled BMD9) and $10^{-9}$ M (−)-desmethyldeprenyl, the major metabolite of (−)-deprenyl (lanes labeled BMDS9). For each of the marker proteins, including PLP, which did not show a decrease after IGF-I/insulin withdrawal, treatment with either of the compounds resulted in a marked increase in immunodensity compared to BM. The increases are in keeping the increased survival of the PROLs and OLs induced by (−)-deprenyl and (−)-desmethyldeprenyl (see below). For MBP, CNP-ase I and PLP, the band densities for BMD9 or BMDs9 exceed those for IM, suggesting that (−)-deprenyl and (−)-desmethyldeprenyl induced an increase in expression of the genes for the proteins.

3.6 (−)-Desmethyldeprenyl, An Active Metabolite of (−)-Deprenyl Is Responsible For the Reduction in Oligodendroglial Apoptosis (−)-Deprenyl on oral administration is rapidly metabolized in the liver and the gastrointestinal tract by cytochrome P450 enzymes to three principal metabolites, (−) desmethyldeprenyl, (−)-methamphetamine and (−)-amphetamine (Heinonen et al., 1994; Rohatagi et al., 1997a; Rohatagi et al., 1997b). Experiments were carried out to determine the effects of the principal metabolites of (−)-deprenyl on oligodendroglial survival.

Figure 11:
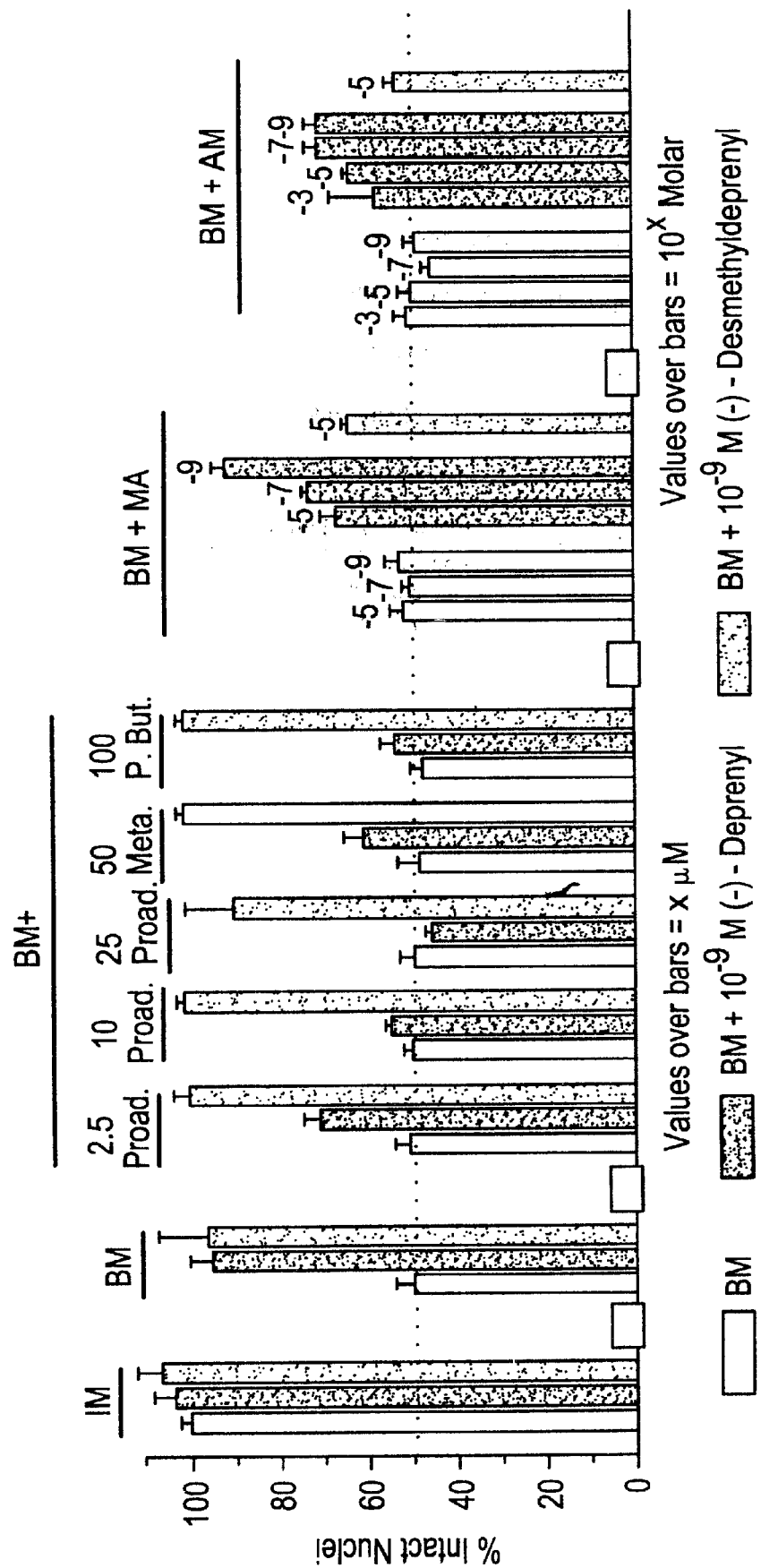
FIG. 11: Effects of general cytochrome P450 blockers on (−)-deprenyl and (−)-desmethyldeprenyl induced changes in OL cell survival. OLs grown on glass coverslips were incubated in BM supplemented with $10^{-9}$ M (−)-deprenyl or (−)-desmethyldeprenyl and treated with the general cytochrome P450 blockers proadifen, metapyrone, or piperonyl butoxide for 24 h. Cells were also treated with (−)-methamphetamine or (−)-amphetamine alone in BM or with $10^{-9}$ M (−)-deprenyl or (−)-desmethyldeprenyl. Concentrations of the P450 blockers as well as of (−)-methamphetamine or (−)-amphetamine are indicated above the respective bars. Intact nuclei were counted on a haemocytometer following Zap-oglobin lysis. Control cells were washed and incubated in IM. Data shown represent the mean percentage of intact nuclei±SEM relative to IM.

Withdrawal of insulin and IGF-I for 24 hours led to intact nuclear counts in BM decreasing to 48.7% compared to those replaced into IM (compare white bars in the groups of bars labeled IM and BM in FIG. 11). As shown in the experiments presented above, washing and placement of the cells in media without IGF-I and insulin, addition of $10^{-9}$ M (−)-deprenyl increased the counts of intact nuclei by 194% compared to those for BM (compare the white and black bars in the BM group of FIG. 11). Treatment of cultures with $10^{-9}$ M (−)-desmethyldeprenyl induced an almost identical 197% increase in the counts (compare the white and gray bars in the BM group of FIG. 11). Controls of adding (−)-deprenyl or (−)-desmethyldeprenyl to cells supported by IGF-I and insulin resulted in the numbers of intact nuclei that were 107% and 103% relative to IM (group labeled IM in FIG. 11).

In contrast to (−)-desmethyldeprenyl, (−)-methamphetamine (MA) or (−)-amphetamine (AM) did alter the counts of intact nuclei. Each was tested at three concentrations of $10^{-5}$, $10^{-7}$ and $10^{-9}$ M (compare white bars in the groups labeled BM+MA and BM+AM to the white bar in the BM group of FIG. 11). The statistical probabilities are shown in Table 5. This data suggests that (−)-desmethyldeprenyl but not (−)-methamphetamine or (−)-amphetamine may mediate the anti-apoptotic actions of (−)-deprenyl on the oligodendroglial cells. It has previously been shown that (−)-desmethyldeprenyl and (−)-desmethyldeprenyl are similarly effective in reducing apoptosis in primary cultures of rat dopaminergic cells after exposure to excitotoxicity (Mytilineou et al., 1997) but it is not known whether one or both of the agents mediate the anti-apoptotic effect. I used blockade of P450 enzyme metabolism of (−)-deprenyl to determine whether one or both mediated the anti-apoptosis.

Three general inhibitors of P450 enzymes, proadifen, metapyrone and piperonyl butoxide, were used to block the P450 enzyme dependent metabolism of (−)-deprenyl into its metabolites. Addition of proadifen at 2.5, 10 and 25 $\mu$M with $10^{-9}$ M (−)-deprenyl resulted in a decrease in the number of intact nuclei to 144%, 109% and 91% when compared to IM (compare the black bars in the groups labeled BM+Proad to that in the BM group in FIG. 11). Importantly, the three concentrations of proadifen did alter the values for BM only (compare the white bars in the groups labeled BM+Proad to that in the BM group in FIG. 11). Furthermore, the three concentrations of proadifen did not reduce the increase in intact nuclei induced by $10^{-9}$ M (−)-desmethyldeprenyl (compare the gray bars in the groups labeled BM+Proad to that in the BM group in FIG. 11). The two other cytochrome P450 enzyme blockers, metapyrone at 50 $\mu$M and piperonyl butoxide at 100 $\mu$M had similar actions to proadifen (groups labeled BM+Meta and BM+P.But. in FIG. 11).

The statistical probabilities for these data are indicated in Table 4. The results obtained show that the general cytochrome P450 blockers completely eliminated the survival enhancing effect of (−)-deprenyl but did not alter the capacity of (−)-desmethyldeprenyl to increase the survival of oligodendroglial cells. Hence the anti-apoptotic effect of (−)-deprenyl on the oligodendroglial cells requires its metabolism to (−)-desmethyldeprenyl.

3.7 (−)-Methamphetamine and (−)-Amphetamine Competitively Reduce the Capacity of (−)-Desmethyldeprenyl to Reduce Oligodendroglial Apoptosis Studies of facial motoneuron survival after axotomy in mice showed that treatment with (−)-methamphetamine and (−)-amphetamine reduced the effectiveness of (−)-deprenyl in improving the survival of the motoneurons (Oh et al., 1994). The basis for the reduction in effectiveness is not known. I therefore undertook competition experiments to determine whether either of the metabolites reduced the capacity of (−)-deprenyl or (−)-desmethyldeprenyl to increase oligodendroglial survival after IGF-I and insulin withdrawal.

Methamphetamine when used in $10^{-5}$ M, $10^{-7}$ M and $10^{-9}$ M concentrations in combination with $10^{-9}$ M (−)-deprenyl significantly reduced the increase in numbers of intact nuclei induced by (−)-deprenyl in a graded concentration dependent manner (compare the black bars in the BM+MA group with the black bar in the BM group of FIG. 11) and $10^{-5}$ M (−)-methamphetamine had a similar competitive action on $10^{-9}$ M (−)-desmethyldeprenyl (compare the gray bar in the BM+MA group with the black bar in the BM group of FIG. 11).

Similarly (−)-amphetamine was used at $10^{-3}$ M, $10^{-5}$ M, $10^{-7}$ M and $10^{-9}$ M concentrations in combination with $10^{-9}$ M (−)-deprenyl or $10^{-9}$ M (−)-desmethyldeprenyl (compare the black and gray bars in the group labeled BM+AM with the black and gray bar in the BM group). Although, the addition of (−)-amphetamine markedly reduced the capacity of (−)-deprenyl to increase the survival of the oligodendroglial cells after IGF-I and insulin withdrawal, grading with concentration not as evident as with (−)-methamphetamine, in part due to greater sample to sample variation (see table 5 for statistical probabilities). (−)-Amphetamine at $10^{-5}$ M completely eliminated the capacity of $10^{-9}$ M (−)-desmethyldeprenyl to increase the survival of the oligodendroglial cells.

These data indicate suggest that the tissue levels of (−)-methamphetamine and/or (−)-amphetamine can be major factors in determining the effectiveness of (−)-deprenyl or (−)-desmethyldeprenyl in reducing oligodendroglial apoptosis. As shown above, the competition does not appear to reflect a pro-apoptotic effect of (−)-methamphetamine or (−)-amphetamine but rather seems to depend on an interference with the mechanism(s) underlying the anti-apoptosis by (−)-desmethyldeprenyl.

TABLE 4

Statistical analysis of data for intact nuclear counts after drug treatments

| Treatment | T-test for independent samples Intact nuclear counts | Mann-Whitney U test Intact nuclear counts |
|---|---|---|
| BM/IM | $7.5 \times 10^{-29}$ | $6.3 \times 10^{-8}$ |
| IM + (−)-Depr/BM | 0.0 | $2.7 \times 10^{-10}$ |
| IM + (−)-Desmeth/BM | $3.4 \times 10^{-26}$ | $3.0 \times 10^{-7}$ |
| BM + (−)-Depr/BM | 0.0 | $3.5 \times 10^{-7}$ |
| BM + (−)-Desmeth/BM | $5.8 \times 10^{-21}$ | $2.7 \times 10^{-10}$ |

TABLE 4-continued

Statistical analysis of data for intact nuclear counts after drug treatments

| Treatment | T-test for independent samples Intact nuclear counts | Mann-Whitney U test Intact nuclear counts |
|---|---|---|
| BM + 2.5 µM Proad/BM | $3.3 \times 10^{-1}$ | $4.4 \times 10^{-1}$ |
| BM + 10 µM Proad/BM | 1.0 | $3.7 \times 10^{-1}$ |
| BM + 25 µM Proad/BM | $8.3 \times 10^{-1}$ | $8.8 \times 10^{-1}$ |
| BM + 50 µM Metyr/BM | $9.6 \times 10^{-2}$ | $1.1 \times 10^{-1}$ |
| BM + 100 µM Pip.But/BM | $1.3 \times 10^{-2}$ | $3.1 \times 10^{-2}$ |
| BM + 2.5 µM Proad + (-)-Depr/BM | $2.7 \times 10^{-9}$ | $1.6 \times 10^{-4}$ |
| BM + 2.5 µM Proad + (-)-Desmeth/BM | $7.8 \times 10^{-11}$ | $1.6 \times 10^{-4}$ |
| BM + 10 µM Proad + (-)-Depr/BM | $5.3 \times 10^{-4}$ | $4.0 \times 10^{-3}$ |
| BM + 10 µM Proad + (-)-Desmeth/BM | $2.3 \times 10^{-10}$ | $4.0 \times 10^{-3}$ |
| BM + 25 µM Proad + (-)-Depr/BM | $4.9 \times 10^{-1}$ | $5.7 \times 10^{-1}$ |
| BM + 25 µM Proad + (-)-Desmeth/BM | $9.3 \times 10^{-10}$ | $4.0 \times 10^{-3}$ |
| BM + 50 µM Metyr + (-)-Depr/BM | $5.0 \times 10^{-6}$ | $1.6 \times 10^{-4}$ |
| BM + 50 µM Metyr + (-)-Desmeth/BM | $2.3 \times 10^{-10}$ | $4.0 \times 10^{-3}$ |
| BM + 100 µM Pip.But + (-)-Depr/BM | $1.0 \times 10^{-1}$ | $1.0 \times 10^{-1}$ |
| BM + 100 µM Pip.But + (-)-Desmeth/BM | $2.3 \times 10^{-10}$ | $4.0 \times 10^{-3}$ |

TABLE 5

Statistical analysis of data for intact nuclear counts after methamphetamine and amphetamine treatments

| Treatment | T-test for independent samples Intact nuclear counts | Mann-Whitney U test Intact nuclear counts |
|---|---|---|
| BM + (-)-Meth $10^{-5}$ M/BM | $7.4 \times 10^{-1}$ | 1.07 |
| BM + (-)-Meth $10^{-7}$ M/BM | 1.0 | 1.0 |
| BM + (-)-Meth $10^{-9}$ M/BM | $3.2 \times 10^{-1}$ | $4.9 \times 10^{-1}$ |
| BM + (-)-Meth $10^{-5}$ M + (-)-Depr/BM | $1.0 \times 10^{-6}$ | $4.0 \times 10^{-3}$ |
| BM + (-)-Meth $10^{-5}$ M + (-)-Desmeth/BM | $6.5 \times 10^{-5}$ | $2.9 \times 10^{-2}$ |
| BM + (-)-Meth $10^{-7}$ M + (-)-Depr/BM | $5.7 \times 10^{-7}$ | $2.9 \times 10^{-2}$ |
| BM + (-)-Meth $10^{-9}$ M + (-)-Depr/BM | $5.1 \times 10^{-8}$ | $2.9 \times 10^{-2}$ |
| BM + (-)-Amph $10^{-3}$ M/BM | $2.6 \times 10^{-1}$ | $2.8 \times 10^{-1}$ |
| BM + (-)-Amph $10^{-5}$ M/BM | 1.0 | $2.6 \times 10^{-1}$ |
| BM + (-)-Amph $10^{-7}$ M/BM | $2.9 \times 10^{-3}$ | $4.0 \times 10^{-3}$ |
| BM + (-)-Amph $10^{-9}$ M/BM | $2.0 \times 10^{-1}$ | $2.8 \times 10^{-1}$ |
| BM + (-)-Amph $10^{-3}$ M + (-)-Depr/BM | $1.5 \times 10^{-1}$ | $5.0 \times 10^{-1}$ |
| BM + (-)-Amph $10^{-5}$ M + (-)-Depr/BM | $1.0 \times 10^{-1}$ | $4.0 \times 10^{-3}$ |
| BM + (-)-Amph $10^{-5}$ M + (-)-Desmeth/BM | $1.7 \times 10^{-2}$ | $2.8 \times 10^{-2}$ |
| BM + (-)-Amph $10^{-7}$ M + (-)-Depr/BM | $3.0 \times 10^{-7}$ | $4.0 \times 10^{-3}$ |
| BM + (-)-Amph $10^{-9}$ M + (-)-Depr/BM | $3.0 \times 10^{-7}$ | $4.0 \times 10^{-3}$ |

Figure 12:
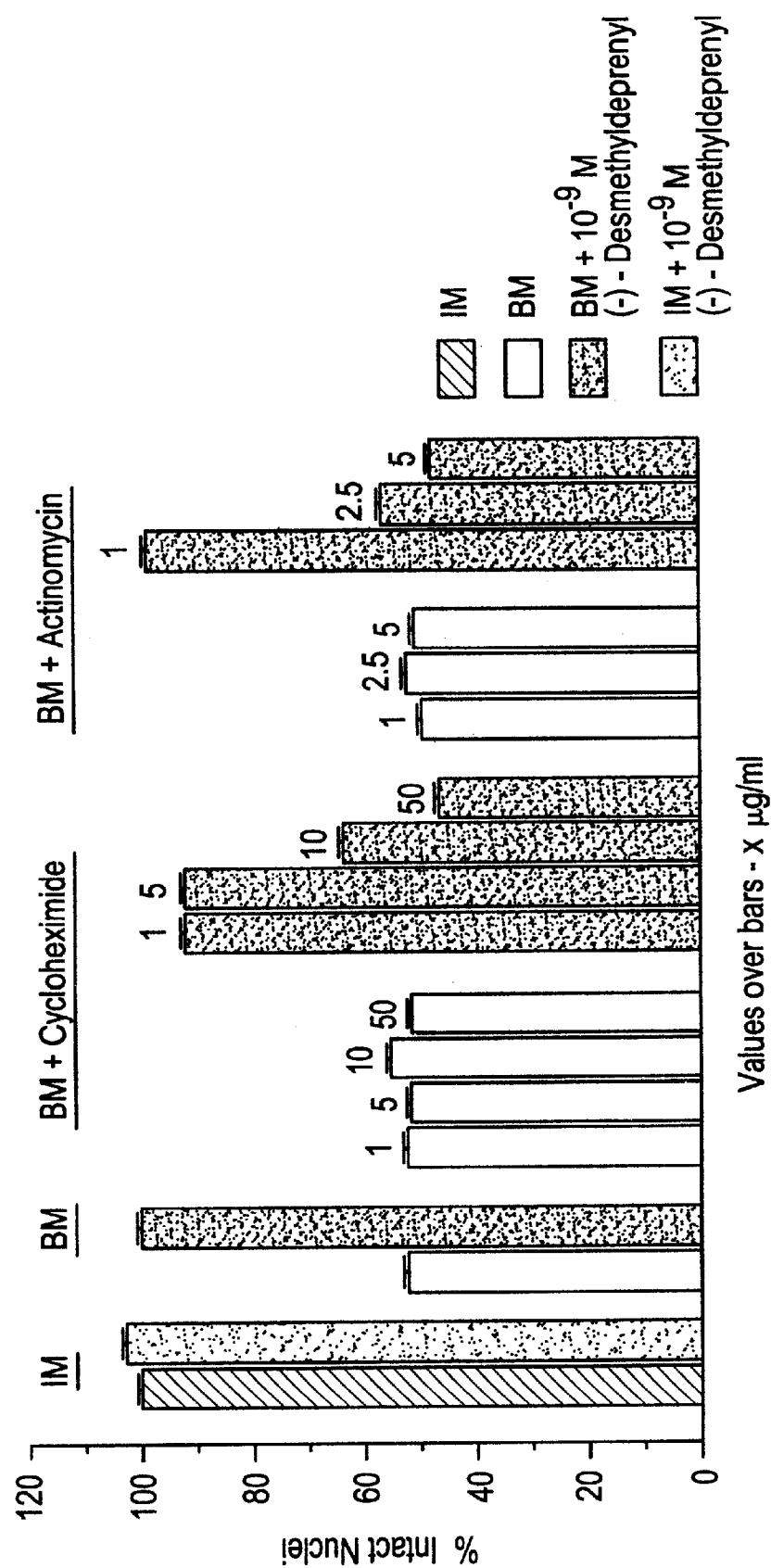
FIG. 12: Reduction of oligodendroglial apoptosis by (−)-desmethyldeprenyl is protein synthesis dependent. After 16 DIV, cells were washed and incubated in BM, BM-Ds9 or BM-Ds9 plus the translation or transcription blockers cycloheximide or actinomycin respectively. Concentrations of cycloheximide and actinomycin are indicated above the respective bars. Intact nuclei were counted on a hemocytometer following Zap-oglobin lysis. Control cells were washed and incubated in IM. Data shown represent the mean percentage of intact nuclei±SEM relative to IM.

3.8 (-)-Desmethyldeprenyl Increases the Survival of Oligodendroglial Cells by Inducing New Protein Synthesis To determine if the increases in survival effected by (-)-desmethyldeprenyl were dependent on transcription or translation in a similar manner to that previously shown for the neuronally differentiated PC12 cells (Tatton et al., 1994), the oligodendroglial cultures were treated with a transcriptional blocker, actinomycin and a translational blocker, cycloheximide. Actinomycin was used at 1, 2.5 and 5 µg/ml while cycloheximide was used at 1, 5, 10, and 50 µg/ml concentrations. Neither agent altered the numbers of intact nuclei for cells that had undergone withdrawal of IGF-I and insulin (compare the white bar in the BM group to the white bars in the BM+Cycloheximide and the BM+Actinomycin groups in FIG. 12). Similar to undifferentiated PC12 cells after serum withdrawal (Rukenstein et al., 1991) and neuronally differentiated PC12 cells after serum and NGF withdrawal (Tatton et al., 1994), this data indicates that apoptosis in the oligodendroglial cells is independent of a requirement for new protein synthesis and proceeds through signaling by constitutive proteins.

In contrast to their action on apoptosis itself, both agents reduced the capacity of $10^{-9}$ M (-)-desmethyldeprenyl to increase the number of the oligodendroglial cells after IGF-I and insulin withdrawal. The reduction in the capacity of (-)-desmethyldeprenyl to increase cell numbers was concentration dependent and induced a complete loss of the (-)-desmethyldeprenyl induced survival at concentrations between 10 and 50 µg/ml for cycloheximide and 2.5 and 5.0 µg/ml for actinomycin D. See tables 6 and 7 for statistical probabilities.

TABLE 6

Statistical analysis of data for intact nuclear counts for cycloheximide treatment

| Treatment | T-test for independent samples Intact nuclear counts | Mann-Whitney U test Intact nuclear counts |
|---|---|---|
| BM/IM | $2.5 \times 10^{-16}$ | $7.7 \times 10^{-4}$ |
| BM + (-)-Desmeth/BM | $1.6 \times 10^{-17}$ | $7.7 \times 10^{-4}$ |
| IM + (-)-Desmeth/BM | $3.7 \times 10^{-17}$ | $7.2 \times 10^{-4}$ |
| BM + 1 µM CHX/BM | $7.4 \times 10^{-1}$ | $8.7 \times 10^{-1}$ |
| BM + 5 µM CHX/BM | $5.3 \times 10^{-1}$ | $6.2 \times 10^{-1}$ |
| BM + 10 µM CHX/BM | $8.0 \times 10^{-2}$ | $1.1 \times 10^{-1}$ |
| BM + 50 µM CHX/BM | $3.0 \times 10^{-1}$ | $5.2 \times 10^{-1}$ |
| BM + 1 µM CHX + Desmeth./BM | $4.2 \times 10^{-14}$ | $7.7 \times 10^{-4}$ |
| BM + 5 µM CHX + Desmeth./BM | $7.9 \times 10^{-16}$ | $7.7 \times 10^{-4}$ |
| BM + 10 µM CHX + Desmeth./BM | $2.4 \times 10^{-8}$ | $7.7 \times 10^{-4}$ |
| BM + 50 µM CHX + Desmeth./BM | $4.2 \times 10^{-5}$ | $7.7 \times 10^{-5}$ |

TABLE 7

Statistical analysis of data for intact nuclear counts for actinomycin treatment

| Treatment | T-test for independent samples Intact nuclear counts | Mann-Whitney U test Intact nuclear counts |
|---|---|---|
| BM/IM | $2.5 \times 10^{-16}$ | $7.7 \times 10^{-4}$ |
| BM + (-)-Desmeth/BM | $1.6 \times 10^{-17}$ | $7.7 \times 10^{-4}$ |
| IM + (-)-Desmeth/BM | $3.7 \times 10^{-17}$ | $7.2 \times 10^{-4}$ |
| BM + 1 µg/ml ACT/BM | $1.3 \times 10^{-1}$ | $1.5 \times 10^{-1}$ |
| BM + 2.5 µg/ml ACT/BM | $7.7 \times 10^{-1}$ | $7.9 \times 10^{-1}$ |
| BM + 5 µg/ml ACT/BM | $6.0 \times 10^{-1}$ | $5.2 \times 10^{-1}$ |
| BM + 1 µg/ml ACT + Desmeth./BM | $4.0 \times 10^{-17}$ | $7.7 \times 10^{-4}$ |
| BM + 2.5 µg/ml ACT + Desmeth./BM | $3.6 \times 10^{-4}$ | $3.2 \times 10^{-3}$ |
| BM + 5 µg/ml ACT + Desmeth./BM | $3.9 \times 10^{-3}$ | $1.1 \times 10^{-2}$ |

Those concentrations are within the range that reduces new protein synthesis to 10% or less in other cell culture systems (see (Rukenstein et al., 1991; Tatton et al., 1994)). Accordingly, (-)-desmethyldeprenyl appears to require new protein synthesis to reduce apoptosis caused by IGF-I and insulin withdrawal in oligodendroglial cells. The interpretation of a need for new protein synthesis is strengthened by the finding that both a translational and a transcriptional inhibitor block the increased survival induced by desmethyldeprenyl.

3.9 Mitochondrial Membrane Potential In Oligodendroglial Apoptosis

Studies in primary cultures of cerebellar neurons (Paterson et al., 1998) and in neuronally differentiated PC12 cells (Wadia et al., 1998) have shown that (-)-deprenyl prevents the decrease in $\Delta\psi_M$ that occurs early in many forms of apoptosis and results in opening of the PTP (see details above). Measurements of mitochondrial CMTMR fluorescence intensities imaged with laser confocal microscopy were used to estimate the $\Delta\psi_M$ in the oligodendroglial cells. CMTMR has been compared to other mitochondrial potentiometric dyes and has been shown to offer a reliable estimate of $\Delta\psi_M$ in individual mitochondria in situ (see (Wadia et al., 1998)). $\Delta\psi_M$ was measured at 18 hours after washing, the time point at which maximum numbers of apoptotic nuclei were found to be present in the oligodendroglial cells (see above).

The distributions of mitochondrial CMTMR fluorescence for PROLs, OLs and ASTs in IM indicated that OL and PROL mitochondria have significantly higher levels of $\Delta\psi_M$ than AST mitochondria (see the upper row of distributions in FIG. 13, typical CMTMR laser confocal microscope images for each type under the corresponding treatment conditions are superimposed on each distribution in FIGS. 13–16). The shape of the distributions indicates that OLs and PROLs have a high proportion of mitochondria with relatively high level $\Delta\psi_M$. Withdrawal of IGF-I and insulin shifted with mitochondrial CMTMR distributions to significantly lower values for the ASTs, PROLs and OLs (see the lower row of distributions in FIG. 13). The relative decreases were particularly marked for the PROL and OL mitochondria. These finding indicate that apoptosis induced in PROLs and OLs by IGF-I and insulin withdrawal involves a decrease in $\Delta\psi_M$ and likely is mitochondrially dependent apoptosis (see above).

Treatment with $10^{-9}$ M (–)-deprenyl (see the upper row of distributions in FIG. 14) and $10^{-9}$ M (–)-desmethyldeprenyl (see the lower row of distributions in FIG. 14) shifted the CMTMR fluorescence distributions for mitochondria in (–)-deprenyl showed that prevention of (–)-deprenyl metabolism by cytochrome P450 inhibition blocked the increases in $\Delta\psi_M$ induced by (–)-deprenyl on OL mitochondria (see the upper row of distributions in FIG. 15). Similar experiments using the three P450 inhibitors with (–)-desmethyldeprenyl, rather than (–)-deprenyl, showed prevention of (–)-deprenyl metabolism did not compromise the capacity of (–)-desmethyldeprenyl to maintain $\Delta\psi_M$ in OL mitochondria after IGF-I/insulin withdrawal (see the lower row of distributions in FIG. 15). These findings appear to correspond to those above in which the three P450 inhibitors blocked the capacity of (–)-deprenyl to increase oligodendroglial survival but did not affect the capacity of (–)-desmethyldeprenyl to increase the survival.

In a final series of experiments, CMTMR mitochondrial fluorescence was measured in IGF-I/insulin withdrawn OL mitochondria treated with $10^{-9}$ M (–)-deprenyl in combination with $10^{-5}$ M (–)-methamphetamine or $10^{-5}$ M (–)-amphetamine (see upper row of distributions in FIG. 16). Similar experiments were carried out with $10^{-9}$ M (–)-desmethyldeprenyl rather than (–)-deprenyl (see lower row of distributions in FIG. 16). These data show that (–)-methamphetamine and (–)-amphetamine competition reduce the capacity of (–)-deprenyl and (–)-desmethyldeprenyl to maintain $\Delta\psi_M$ in OL mitochondria after IGF-I and insulin withdrawal. These findings appear to correspond to the findings presented above showing that (–)-methamphetamine and (–)-amphetamine competition reduces the capacity of (–)-deprenyl and (–)-desmethyldeprenyl to increase the survival of oligodendroglial cells after IGF-I and insulin withdrawal.

TABLE 8

Statistical testing of data for the mitochondrial membrane potential ($\Delta\psi_M$) of oligodendroglial cells

| Treatment | Mann-Whitney U Test | | | Treatment | T-test for independent samples | | |
| --- | --- | --- | --- | --- | --- | --- | --- |
| | AST | PROL | OL | | AST | PROL | OL |
| BM/IM | $>1.00 \times 10^{-15}$ | $>1.00 \times 10^{-15}$ | $>1.00 \times 10^{-15}$ | BM/IM | $>1.00 \times 10^{-15}$ | $>1.00 \times 10^{-15}$ | $>1.00 \times 10^{-15}$ |
| BM-D9/BM | $>1.00 \times 10^{-15}$ | $>1.00 \times 10^{-15}$ | $>1.00 \times 10^{-15}$ | BM-D9/BM | $>1.00 \times 10^{-15}$ | $>1.00 \times 10^{-15}$ | $>1.00 \times 10^{-15}$ |
| BM-D9/IM | $4.4 \times 10^{-5}$ | $2.6 \times 10^{-7}$ | $8.8 \times 10^{-5}$ | BM-D9/IM | $4.9 \times 10^{-5}$ | $2.0 \times 10^{-7}$ | $3.6 \times 10^{-14}$ |
| BM-DS9/BM | $>1.00 \times 10^{-15}$ | $>1.00 \times 10^{-15}$ | $>1.00 \times 10^{-15}$ | BM-DS9/BM | $>1.00 \times 10^{-15}$ | $>1.00 \times 10^{-15}$ | $>1.00 \times 10^{-15}$ |
| BM-DS9/IM | $>1.00 \times 10^{-15}$ | $1.1 \times 10^{-3}$ | $8.8 \times 10^{-14}$ | BM-DS9/IM | $>1.0 \times 10^{-15}$ | $1.8 \times 10^{-2}$ | $6.9 \times 10^{-1}$ |
| BM-D9 + Proad./BM | — | — | $4.23 \times 10^{-13}$ | BM-D9 + Proad./BM | — | — | $1.2 \times 10^{-10}$ |
| BM-Ds9 + Proad./BM | — | — | $>1.00 \times 10^{-15}$ | BM-Ds9 + Proad./BM | — | — | $>1.00 \times 10^{-15}$ |
| BM-D9 + Meta./BM | — | — | $2.9 \times 10^{-1}$ | BM-D9 + Meta./BM | — | — | $7.7 \times 10^{-1}$ |
| BM-Ds9 + Meta./BM | — | — | $>1.00 \times 10^{15}$ | BM-Ds9 + Meta./BM | — | — | $>1.00 \times 10^{-15}$ |
| BM-D9 + P. But/BM | — | — | $4.8 \times 10^{-14}$ | BM-D9 + P. But/BM | — | — | $9.5 \times 10^{-1}$ |
| BM-Ds9 + P. But/BM | — | — | $>1.00 \times 10^{-15}$ | BM-Ds9 + P. But/BM | — | — | $>1.00 \times 10^{-15}$ |
| BM-D9 + MA./BM | — | — | $3.6 \times 10^{-4}$ | BM-D9 + MA/BM | — | — | $3.7 \times 10^{-5}$ |
| BM-Ds9 + MA./BM | — | — | $6.4 \times 10^{-1}$ | BM-Ds9 + MA/BM | — | — | $1.0 \times 10^{-1}$ |
| BM-D9 + AM/BM | — | — | $2.0 \times 10^{-1}$ | BM-D9 + AM/BM | — | — | $2.0 \times 10^{-1}$ |
| BM-Ds9 + AM/BM | — | — | $1.3 \times 10^{-1}$ | BM-Ds9 + AM/BM | — | — | $4.7 \times 10^{-1}$ |

ASTs, PROLs and OLs to levels that were not significantly different to those found for IM (see Table 8). Similar to cultured cerebellar neurons (Paterson et al., 1998) and neuronally differentiated PC12 cells (Paterson et al., 1998), (–)-deprenyl prevented the decreases in PROLs and OLs which may account for its capacity to reduce apoptosis in the cells. This is the first study to show that (–)-desmethyldeprenyl shares the capacity of (–)-deprenyl to maintain $\Delta\psi_M$ in cells that have sustained an insult that leads to apoptosis, in this case IGF-I and insulin withdrawal.

Experiments in which proadifen (10 $\mu$M), metyapone (50 $\mu$M) or piperonyl butoxide (100 $\mu$M) were added to IGF-I/insulin withdrawn cells that were treated with $10^{-9}$ M 4.0 Discussion 4.1 An In Vitro Model System This thesis describes a primary culture model established to study the death of PROLs and OLs after IGF-I and insulin-withdrawal. There are certain advantages to the use of glial primary cultures. First, the purity of the cell populations derived from the primary mixed glial cultures is considerably higher when compared to the cell populations obtained from explants or reaggregate cultures. Second, mixed glial primary cultures offer the advantage of the presence of a stratified layer of O-2A progenitor cells over an astrocytic cell layer therefore purified populations of oligodendrocytes or astrocytes can be obtained from the same culture using a replating procedure.

O-2A progenitors can be isolated from the underlying astrocytic layer using mechanical shake-off method, by immunoisolation on solid substrates, or by fluorescence activated cell sorting. The isolated progenitors can be then developmentally synchronized to obtain cells at specific phenotypic stages. The use of primary cultures allows for the control of the microenvironment in which the primary cultured cells grow. Defined culture conditions facilitate the developmental synchronization of the O-2A progenitor differentiation. In addition, a controlled culture environment facilitates the identification and testing of the effects of trophic factors or other agents on oligodendroglial differentiation or survival.

An important finding of the studies utilizing in vitro models is that oligodendroglial cells in culture follow a schedule that approximates the timing of differentiation of the progenitor cells in vivo (Gard and Pfeiffer, 1989). Oligodendroglial cells are formed at birth and differentiate postnatally as opposed to neurons, which become established during embryogenesis. It is interesting to note that oligodendrocytes develop later than neuronal cells after the completion of axonal outgrowth. This late development has been postulated to occur because oligodendrocytes exert a strong inhibitory effect on axonal growth (Caroni and Schwab, 1988).

The cerebral O-2A progenitor cells were first identified in a rat optic nerve model (Raff et al., 1983). The current study has utilized O-2A progenitor cells isolated from the cerebral cortices of the rat in its in vitro model system. Several other studies have used the rat cerebral cortex as a source for isolating O-2A progenitor cells instead of the optic nerve (Behar et al., 1988; Espinosa de los Monteros et al., 1988; Espinosa de los Monteros et al., 1986; McMorris et al., 1986). The use of the cerebral cortex offers the advantage of obtaining a higher yield of O-2A progenitor cells in comparison to the optic nerve.

4.2 Immunocytochemical and Morphological Cell Identification

The identification of oligodendroglial cell types on the sole basis of immunocytochemical data is not always practical by itself. This can be illustrated by using the example of the cell stage specific expression of a surface antigen, galactocerebroside (GC). Many earlier studies incorrectly interpreted the expression of GC to be linked to terminal differentiation and maturation of oligodendroglial cells. As the O-2A progenitor cells differentiate into the partially differentiated PROLs, the cells lose their reactivity to A2B5 and begin to express the surface antigen GC and an intracellular antigen, CNPase-I. Therefore, the expression of GC coincides with the appearance of PROLs rather than the OLs. The PROLs mature to form the fully differentiated OLs. Previous studies have shown that that cells at this final stage of differentiation express MBP and PLP. Additionally, the differentiated cells also continue to express the PROL markers, GC and CNPase-I. Since there is a considerable overlap in the expression of antigens in the partially differentiated and fully differentiated oligodendroglial cells, it is necessary to combine the immunocytochemical observations with morphological features of these cells to correctly identify of the cell types found in the oligodendroglial lineage.

In the present study, positive identification of the individual cell types in the cultures was achieved using a combination of approaches including phase contrast microscopy, immunocytochemistry and methylene blue morphological staining. The PROLs were found to express GC and CNPase-I and had three to four primary processes with few secondary processes. The fully differentiated OLs however were seen to possess six to eight primary processes and numerous web-like secondary and tertiary processes and also were immunopositive for antibodies that recognized MBP and PLP. The identification of MBP and PLP immunopositive cells as fully differentiated cells of the oligodendroglial lineage gains support from several studies which have observed that the MBP positive cells are incapable of any further cell division (Wood and Bunge, 1986).

The correlation of the presence of immunocytochemical marker proteins to specific morphological changes in the cells, particularly changes in process morphology, allowed for the counting of changes in the numbers of specific cell types at a number of time points after IGF-I and insulin withdrawal using a simple methylene blue staining process. Because of cell to cell variability in immunoreaction product, dependence on immunocytochemistry alone would have made the procedure considerably less reliable.

4.3 Insulin and IGF-I and Oligodendroglial Proliferation and Differentiation

Insulin and IGF-I are structurally and functionally related polypeptides that regulate a number of cellular processes like proliferation, differentiation and survival. The CNS was thought to be insulin and IGF-I independent since serum insulin and IGF-I do not cross the blood-brain barrier. However, the findings of the presence of insulin and insulin receptors in the rat brain radically changed the view that the CNS was insulin independent (Baskin et al., 1983; Havrankova et al., 1978; Kappy et al., 1984). It is now known that IGF-I and II, their receptors, and IGF binding proteins (IGFBPs; secreted proteins that modulate IGF actions) are expressed early in CNS development (Baxter, 1991). So far six IGFBPs (IGFBP-1 through 6) have been identified. The IGFBPs have been suggested to augment the binding of IGF-I to its cell surface receptors. Binding sites for IGF-I have now been identified in virtually all brain regions of the adult rat brain using quantitative autoradiographic techniques (Bohannon et al., 1988).

IGF-I is synthesized in the subventricular zone of the brain by type-1 astrocytes (Ballotti et al., 1987; Bartlett et al., 1991; Rotwein et al., 1988). In situ hybridization studies have determined that, in the CNS of the rat, IGF-I expression begins by embryonic day 14 (Bartlett et al., 1991) with peak expression of IGF-I occurring postnatally (Rotwein et al., 1988; Werner et al., 1989). The expression pattern of IGF system proteins during brain growth suggests highly regulated and developmentally timed IGF actions on specific populations of neurons. Apart from influencing neuronal development, IGF-I is also critical to oligodendroglial proliferation and differentiation.

In vitro, IGF-I has been shown to stimulate the proliferation of neuron progenitors and/or the survival of neurons and oligodendrocytes, and in some cultured neurons, to stimulate functions like neurite outgrowth and differentiation. McMorris and co-workers (McMorris et al., 1986) found that physiological concentrations of insulin and IGF-I induced the proliferation of O-2A progenitor cells. The proliferative effect of IGF-I on the O-2A progenitor cells was demonstrated by using tritiated thymidine incorporation of newly synthesized DNA as a marker of oligodendrocyte proliferation in vitro (McMorris and Dubois Dalcq, 1988). The same study also observed decreased tritiated thymidine labeling when cells were grown for two weeks or longer suggesting that IGF-I is not mitogenic to the O-2A lineage cells upon their differentiation into oligodendrocytes. It seems likely that both insulin and IGF-I together influence O-2A cell proliferation. This developmental feature gains indirect support from the evidence that both insulin (IR) and IGF receptor (IGFR) mRNAs have been found in O-2A progenitor cells (Han et al., 1987; Shemer et al., 1987; Van Schravendijk et al., 1984). The insulin receptor mRNA levels found in O-2A progenitor cells is about 30 times more than that found in astrocytes or in neuronal cells (Baron Van Evercooren et al., 1991). Accordingly, the facilitation of O-2A cell proliferation by insulin and IGF-I likely accounts for high proportion of O-2A cells found at day 12 in the in vitro model developed in the present thesis work.

Insulin and/or IGF-I act as a differentiation factor for the O-2A progenitor cells. The biological effects of insulin and IGF-I on oligodendroglial differentiation are triggered by the specific binding of these molecules to IR and IGFR (Mozell and McMorris, 1991). Receptor blocking experiments have revealed that the relative potency of induction of oligodendrocyte development depends on the binding affinity to IGFRs (McMorris et al., 1986). The beta subunit of both IR and IGFR consists of a transmembrane polypeptide chain, which contains a highly conserved catalytic tyrosine kinase domain. Within a few seconds of the binding of insulin and IGF-I to its receptors, the tyrosines undergo rapid phosphorylation. This subsequently leads to the phosphorylation of several intracellular substrates like Ras, Raf and phosphoinosityl-3-kinase (PI-3 kinase) which eventually induce oligodendroglial proliferation and subsequent differentiation into the mature oligodendroglia.

The occurrence of IGF-I mRNA in both the gray and white matter areas of the developing rat brain indicated that developing oligodendrocytes might themselves be synthesizing IGF-I for their subsequent maturation (Rotwein et al., 1988). This finding suggests that differentiation of oligodendrocyte precursors is not only regulated by the IGF-I produced by the type-1 astrocytes but also by the release of IGF-I in an autoregulatory manner. The influence of insulin and IGF-I on O-2A differentiation likely contributed to the rapid increase the number of PROLs and OLs between 12 and 16 DIV found in the present in vitro model.

Insulin and IGF-I are considered to be involved in the regulation of myelin gene expression and myelin synthesis. In the present study, data obtained suggests that insulin and IGF-I regulate PROL and OL specific proteins like GC, CNPase-I, MBP and PLP. The western blot data presented in the present study showed a decrease in MBP, GC and CNPase I in the oligodendroglial cells after IGF-I and insulin withdrawal. Although part of the decrease can likely be accounted for by the greater proportion of death of PROLs and OLs than other cell types in the cultures, part of the decrease may result from decreased synthesis of the three proteins caused by the withdrawal of IGF-I and insulin.

Little is known about the functional roles of the four PROL and OL proteins. MBP and PLP together form 80% of the total myelin in the CNS. There have been recent reports on the involvement of PLP in mediating the survival of oligodendrocytes. In mice carrying mutations of PLP, there is a dramatic decrease in the numbers of oligodendrocytes as well as aberrant myelin formation (Jackson and Duncan, 1988). This suggests that PLP is crucial for the survival and myelinating capabilities of oligodendroglial cells.

Paradoxically, other studies have offered evidence that overexpression of the PLP gene leads to OL cell death (Kagawa et al., 1994). A very recent study has demonstrated that the perinuclear accumulation of PLP leads to the apoptotic death of OLs in a mice model of Pelizaeus-Merzbacher disease, a demyelinating disease occurring due to mutations, deletions or duplications of the PLP gene (Gow et al., 1998). The findings of all these studies suggest that PLP may play a role in regulating OL survival.

4.4 Insulin, IGF-I and Oligodendroglial Apoptosis

The in vitro model system of the present study demonstrates that insulin and IGF-I serve to decrease apoptosis in O-2A progenitors, PROLs and OLs. Studies with oligodendrocytes in the rat optic nerve have revealed that oligodendroglial cells are overproduced during development (Barres et al., 1992). Over half of the newly formed oligodendrocyte progenitor cells die due to lack of available trophic signals. Based on their findings, Barres and co-workers hypothesized that survival/trophic factors ultimately decide the final numbers of myelin forming oligodendrocytes in any specific region of the CNS. Insulin and IGF-I, not only affect oligodendroglial differentiation and maturation but also contribute to the regulation of oligodendroglial cell survival (McMorris et al., 1993).

It was previously shown that IGF-I and insulin decrease apoptosis in O-2A progenitors which was thought to be the point of regulation of OL numbers (Barres et al., 1992). Data from the present study is the first to show that insulin and IGF-I can also decrease apoptosis of PROLs and OLs. These findings are consistent with previous studies showing that insulin can increase the numbers of oligodendrocytes grown in serum free conditions (Eccleston and Silberberg, 1984; Saneto and de Vellis, 1985). Other studies have shown that IGF-I produced by developing oligodendrocytes or astrocytes, acts additively with trophic factors like PDGF and NT-3 to promote the proliferation and survival of oligodendrocyte precursor cells (Barres et al., 1993). The present study suggests that similar actions may extend to fully differentiated OLs themselves and those actions may depend on an anti-apoptotic capacity of IGF-I and insulin on the OLs.

Very few studies have focused on glial cell apoptosis, more particularly on PROL and OL apoptosis. The first report showing a possible relationship between trophic factor withdrawal and an O-2A lineage cell apoptosis came from the studies of Barres and colleagues (Barres et al., 1992). Their study demonstrated that newly formed oligodendroglial precursors die with morphological features suggestive of apoptosis when deprived of trophic support. Another study demonstrated that oligodendroglial progenitor cells isolated from the rat forebrain showed apoptotic cell death features upon removal of bFGF (Yasuda et al., 1995). The results of the present study show that differentiated cells of the oligodendroglial lineage like the PROLs and the OLs die by apoptosis upon withdrawal of insulin and IGF-I. The presence of a combination of trophic factors may be essential to prevent oligodendroglial cell apoptosis in vivo.

The insulin and IGF-I withdrawn oligodendroglial cells showed evidence for apoptotic nuclear degradation within 6 hours after IGF-I and insulin withdrawal. Peak apoptotic death was observed at 18 hours after withdrawal of insulin and IGF-I. The time course of apoptosis observed in the present study is similar to that of IGF-I deprived rat optic nerve O-2A progenitor cells which die within 18 hours (Barres et al., 1992). Based upon those findings, it seems likely that after withdrawal of insulin and IGF-I, both undifferentiated O-2A progenitor cells and differentiated PROLs and OLs undergo apoptosis with a similar time course of death. However, the present studies suggested that IGF-I/insulin withdrawal induced apoptotic death seems to be higher in the more differentiated cells of the oligodendroglial lineage.

The time course of apoptotic cell death can vary depending on the cell type and the insult that induces apoptosis.

Apoptosis in neuronally differentiated PC12 cells has been seen to begin between 6 and 12 hours after serum and NGF withdrawal (Wadia et al., 1998). The apoptotic death of insulin and IGF-I deprived oligodendroglial cells appears to occur over a more protracted time course that of the serum and NGF deprived PC12 cells. The time course of apoptosis seems to depend on the intensity of the insult that induces the apoptosis (Hartley et al., 1994), which may account for the longer time course of the oligodendroglial apoptosis induced by IGF-I and insulin withdrawal.

4.5 Cell Density and Apoptosis

Although it is known that the absence of trophic factors, insulin and IGF-I decreases the survival of oligodendroglial cells, it is not known whether extrinsic factors like cell plating density regulates oligodendroglial apoptosis. The present study demonstrates that oligodendroglial cells underwent apoptosis, which was at least in part, mediated by cell plating density. At lower plating density, the number of apoptotic nuclei was approximately 15 fold higher in BM as opposed to IM. Higher plating density however increased the number of apoptotic nuclei in BM approximately 8.5 fold higher than in IM. This data suggests that oligodendroglial cells at lower plating density are more vulnerable to apoptosis induced by trophic withdrawal.

Lower plating densities have been shown to cause apoptotic cell death in several cell types. Lens epithelial cells, rat and chick chondrocytes, HL-60 cells, sciatic nerve fibroblasts and neutrophils die by apoptosis when cultured in low plating densities in the absence of serum or growth factors (Ishizaki et al., 1994; Ishizaki et al., 1995). A number of possibilities emerge that could account for the decreased survival and increased apoptosis when cells are cultured at lower plating densities. First, it seems likely that an absence of extracellular survival promoting signals can decrease cell survival. Secondly, at lower plating densities there might be a decrease in the levels of antioxidant molecules which would thereby facilitate the intracellular build up of oxidative radicals that can cause cell death by apoptosis. Lastly, lower plating densities might induce the release of apoptosis-initiating factor by a mechanism that would involve the activation of ICE like proteases, as described earlier. The released apoptosis initiating factors can induce apoptotic DNA fragmentation.

4.6 New Protein Synthesis and OL and PROL Apoptosis

As shown for the first time by the above studies using actinomycin D and cycloheximide, in a similar manner to the PC12 cell apoptosis caused by serum (Rukenstein et al., 1991) or serum and NGF withdrawal (Tatton et al., 1994), oligodendroglial apoptosis induced by IGF-I and insulin withdrawal is new protein synthesis independent. Those findings contrast with an earlier report that cycloheximide and actinomycin D inhibit the cell death of O-2A progenitor cells (Barres et al., 1992). The study of Barres and colleagues (Barres et al., 1992) hypothesized that oligodendroglial cells possess a suicide program which is activated when cells are deprived of essential trophic support. It is possible that newly formed oligodendroglial precursor cells, which were examined in that study, require the synthesis of "death" proteins to complete the apoptotic process. However, further differentiation into PROLs and OLs may result in a modification of the apoptotic process so that newly synthesized proteins are not required and the process depends on constitutive proteins.

4.7 (−)-Deprenyl and Increased Oligodendroglial Survival

The present study showed that (−)-deprenyl increased the survival of oligodendroglial cells which were deprived of insulin and IGF-I. The anti-apoptotic action of deprenyl seems to be limited to its (−) enantiomer (Ansari et al., 1993) as has been shown for oligodendroglial cells in the present studies. (−)-Deprenyl inhibits MAO-B by forming a non-covalent complex leading to the oxidation of (−)-deprenyl and reduction of the flavine adenine dinucleotide (FAD) moiety. (−)-Deprenyl and the reduced FAD moiety bind covalently. Since MAO-B possesses FAD binding domains, (−)-deprenyl in combination with reduced FAD binds to the enzyme and inactivates it.

However, as discussed above, (−)-deprenyl mediates its survival enhancing action in an MAO-B independent manner. Recent work has suggested that (−)-deprenyl like compounds may reduce apoptosis by binding to glyceraldehyde-3-phosphate dehydrogenase (GAPDH) (Kragten et al., 1998). Although GAPDH facilitates apoptosis in a variety of types of neurons (Ishitani and Chuang, 1996; Ishitani et al., 1996; Ishitani et al., 1996; Ishitani et al., 1997; Sunaga et al., 1995), it is not known whether it plays a role in oligodendroglial apoptosis.

The finding that (−)-deprenyl reduces oligodendroglial apoptosis suggest a possible for GAPDH in that apoptosis, if in fact, binding to GAPDH mediates (−)-deprenyl anti-apoptosis. The P450 cytochrome blockade experiments in present work are the first to establish that (−)-desmethyldeprenyl rather than (−)-deprenyl itself mediates the anti-apoptosis in the oligodendroglial cells. Experiments with three different general P450 cytochrome inhibitors, proadifen (SKF 525A), piperonyl butoxide and metapyrone, all led to the same findings: 1) that prevention of (−)-deprenyl metabolism by P450 cytochromes blocks the capacity of the compound to reduce oligodendroglial apoptosis and 2) prevention of the metabolism of (−)-desmethyldeprenyl by P450 cytochromes does impair the capacity of (−)-desmethyldeprenyl to reduce oligodendroglial apoptosis. Three P450 cytochrome inhibitors were required since most of the inhibitors have several sites of action. For example, proadifen and metapyrone inhibit P450 cytochromes and both also modulate bradykinin-releasable $Ca^{2+}$-pumping pools in cells (Graber et al., 1997; Suarez-Kurtz and Bianchi, 1970). Modulation of the $Ca^{2+}$ pools might be argued to be responsible for the blockade of anti-apoptosis by (−)-deprenyl rather than P450 cytochrome inhibition. Piperonyl butoxide also inhibits P450 cytochromes but does not share the $Ca^{2+}$ action of the other two inhibitors (Benchaoui and McKellar, 1996). Accordingly, the use of three different inhibitors greatly strengthens the interpretation that cytochrome P450 mediated metabolism of (−)-deprenyl is necessary for its anti-apoptotic action. Since (−)-desmethyldeprenyl appears to be the active compound, it might bind to GAPDH, rather than (−)-deprenyl, and the binding may compromise the pro-apoptotic capacity of GAPDH, thereby reducing apoptosis in the oligodendroglial cells. It is possible that (+)-desmethyldeprenyl may not bind to the protein, which would account for the stereospecificity of the anti-apoptotic action on the oligodendroglial cells.

The anti-apoptotic effects of (−)-deprenyl on neuronally differentiated PC12 cells has been attributed to a capacity to alter gene transcription and induce selective changes in new protein synthesis (Tatton and Chalmers Redman, 1996). It is likely that similar changes in new protein synthesis are induced in the oligodendroglial cells, given the above findings which show that transcriptional or translational inhibition prevents either (−)-deprenyl or (−)-desmethyldeprenyl from reducing oligodendroglial apoptosis.

As detailed above, (−)-deprenyl treatment induces changes in the levels of a large number of proteins in different cell types, including increases in BCL-2 (Tatton et al., 1994). BCL-2 has been shown to be located, in part, in the outer membranes of mitochondria (Lithgow et al., 1994; Riparbelli et al., 1995), near to or at the peripheral bezodiazepine binding protein of the PTP (Carayon et al., 1996). Kroemer and colleagues have shown that the presence of BCL-2 near the PTP serves to maintain PTP closure and maintain $\Delta\psi_M$ (Marchetti et al., 1996; Zanzami et al., 1996). In early apoptosis, BCL-2 decreases in the mitochondrial membranes (Gillardon et al., 1995), which results in PTP opening and likely contributes to the early apoptotic decrease in $\Delta\psi_M$. Opening of the PTP, associated with the decrease in ATM, results in the free exchange of solutes between the mitochondrial matrix and the cytosol, mitochondrial swelling and the escape of mitochondrial factors which induce the degradative phase of apoptosis (see (Kroemer et al., 1997)). Mitochondrial BCL-2 has been shown to prevent the release of pro-apoptotic factors from mitochondria (Susin et al., 1996; Yang et al., 1997). Agents which maintain or increase cellular levels of BCL-2, like (−)-deprenyl, would therefore be expected to maintain $\Delta\psi_M$ and prevent opening of the PTP leading to apoptotic degradation (see (Wadia et al., 1998)).

GAPDH appears to promote apoptosis by down regulation of the increase in BCL-2 synthesis that accompanies cellular damage (Carlile, Chalmers-Redman, Borden and Tatton, personal communication). The above finding that (−)-deprenyl and (−)-desmethyldeprenyl maintain $\Delta\psi_M$ in the oligodendroglial cells could be explained by the binding of (−)-desmethyldeprenyl to GAPDH leading to a maintenance of $\Delta\psi_M$ with maintained closure of the PTP. Prevention of PTP opening would then result in a decrease in apoptosis in the cells. The validity of this model for the action of (−)-desmethyldeprenyl will have to be evaluated in a step by step manner in the oligodendroglial cells.

Rather than acting directly on the oligodendroglial cells to increase BCL-2 levels, (−)-desmethyldeprenyl may act through astroglial intermediaries. (−)-Deprenyl has been shown to increase the synthesis of CNTF, NGF and bFGF in astrocytes (Biagini et al., 1994; Semkova et al., 1996; Seniuk et al., 1994). It has been suggested that increased availability of trophic support may account for the anti-apoptotic capacity of (−)-deprenyl (Koutsilieri et al., 1996). A trophic basis for the decreased apoptosis could also explain the maintenance of $\Delta\psi_M$ in the oligodendroglial cells since some trophic factors have been shown to increase $\Delta\psi_M$ (Mattson et al., 1993).

The present understanding of apoptosis is thought to be associated with a sequence of mitochondrial events involving opening of the PTP and a decrease in $\Delta\psi_M$. Although the studies of Wadia and colleagues (Wadia et al., 1998) as well as Paterson and co-workers (Paterson et al., 1998) make direct measurements of mitochondria to demonstrate a fall in the $\Delta\psi_M$ in early apoptosis, it might be argued, though, that the decrease in $\Delta\psi_M$ is simply a correlate of apoptotic death, but is not one of the steps leading to the death. As shown in my studies, the level of cell survival and $\Delta\psi_M$ covary across a number of different treatments. That is, as shown in table 9, factors which increase or decrease survival have the same effect on $\Delta\psi_M$. These findings strengthen the argument that decreases in $\Delta\psi_M$ play a role in the genesis of oligodendroglial apoptosis.

TABLE 9

Relationship between $\Delta\Psi_M$ and OL cell survival.

| | Survival (24 h) | $\Delta\Psi_M$ (18 h) |
|---|---|---|
| IM | ++++ | ++++ |
| BM | ++ | ++ |
| BM-D9 | ++++ | +++ |
| BM-Ds9 | ++++ | ++++ |
| BM-D9 + Proad. | ++ | ++ |
| BM-D9 + Meta. | ++ | ++ |
| BM-D9 + P.But. | ++ | ++ |
| BM-Ds9 + Proad. | ++++ | ++++ |
| BM-Ds9 + Meta. | ++++ | ++++ |
| BM-Ds9 + P.But. | ++++ | ++++ |
| BM-D9 + MA | ++ | + |
| BM-D9 + AM | ++ | + |
| BM-Ds9 + MA | ++ | + |
| BM-Ds9 + AM | + | + |

++++ = Control Levels
+++ = 60–90% of Control
++ = 30–60% of Control
+ = 0–30% of Control

4.8 Possible Therapeutic Benefits

Given recent evidence that OL apoptosis plays a role in the pathogenesis of MS (see introduction section above), agents like (−)-desmethyldeprenyl that reduce oligodendroglial apoptosis may be of value in slowing the time course of MS and reducing the severity of the neurological deficits associated with the disease.

5.0 Summary

The data presented in this thesis describes a primary culture model established to study glial cell apoptosis and the capacity of (−)-deprenyl and its metabolites to reduce apoptotic death. It is known that the differentiated cells of the O-2A lineage, PROLs and OLs are targets of degeneration and death in demyelinating diseases of the CNS. This primary culture model allows for the study of the cell death process in differentiated PROLs and OLs as opposed to other models, which have largely used O-2A progenitors. The study uses a number of measures to demonstrate the relationship between cellular loss and apoptotic nuclear degeneration apoptosis of differentiated PROLs and OLs upon withdrawal of insulin and IGF-I. Specifically, apoptotic death was confirmed by using two independent in situ methods as well as DNA gel electrophoresis. Peak apoptotic cell death for OLs and PROLs was found to occur at 18 h after withdrawal of IGF-I and insulin. Cell death was also appeared to vary depending on the plating density of the cultures.

Apoptosis of the IGF-I and insulin withdrawn PROLs and OLs was significantly reduced by (−)-deprenyl. The (+) enantiomer of deprenyl did not reduce PROL and OL death showing that the actions of deprenyl is stereospecific. (−)-Deprenyl could reduce death of all the cell types of the O-2A lineage, but most particularly PROLs and OLs. This study demonstrated that a major metabolite of deprenyl, (−)-desmethyldeprenyl was also effective in reducing PROL and OL apoptosis. Blockade of cytochrome P450 enzyme dependent metabolism of (−)-deprenyl but not of (−)-desmethyldeprenyl, established that (−)-desmethyldeprenyl was the active metabolite responsible for the anti-apoptotic effects of (−)-deprenyl. The other two major metabolites of (−)-deprenyl, (−)-methamphetamine and (−)-amphetamine did not improve cell survival after IGF-I and insulin withdrawal but competitively inhibited the anti-apoptotic actions of (−)-deprenyl or (−)-desmethyldeprenyl. The anti-apoptotic effects of (−)-desmethyldeprenyl was found to be blocked by cycloheximide and actinomycin D showing that (−)-desmethyldeprenyl was dependent on the induction of new protein synthesis for its anti-apoptotic action. Furthermore, Western blot analysis of protein levels revealed that insulin and IGF-I withdrawal decreased the levels of PROL proteins like CNP, GC and MBP but not of PLP.

The present study demonstrated that withdrawal of IGF-I and insulin shifted the mitochondrial CMTMR fluorescence intensity distributions to lower values, which represented decreases in $\Delta\psi_M$ in the OLs, PROLs and ASTs. (−)-Deprenyl and its major metabolite (−)-desmethyldeprenyl prevented the shift of the distributions to lower values. Furthermore, experiments with cytochrome P450 inhibitors showed that the effects of (−)-deprenyl on $\Delta\psi_M$ could be blocked but not that of (−)-desmethyldeprenyl. The other metabolites of (−)-deprenyl, (−)-methamphetamine and (−)-amphetamine, at high concentrations, shifted the mitochondrial fluorescence distributions to lower values showing a blockade of the effects of both (−)-deprenyl and (−)-desmethyldeprenyl on $\Delta\psi_M$. These results suggest that mitochondria participate in IGF-I and insulin withdrawal induced apoptosis of OLs and PROLs, and that maintenance of $\Delta\psi_M$ is critical to the survival of the differentiated PROLs and OLs.

6.0 References

Abakumova, O. Y., Podobed, O. V., Tsvetkova, T. A., Yakusheva, I. V., Moskvitina, T. A., Kondakova, L. I., Navasardyantz, D. G., and Medvedev, A. E. (1998). Modulation of glutamate neurotoxicity in the transformed cell culture by monamine oxidase inhibitors, clorgyline and deprenyl. J Neural Transm Suppl, 87–91.

Abney, E. R., Bartlett, P. P., and Raff, M. C. (1981). Astrocytes, ependymal cells, and oligodendrocytes develop on schedule in dissociated cell cultures of embryonic rat brain. Dev Biol 83, 301–10.

Amenta, F., Bongrani, S., Cadel, S., Ricci, A., Valsecchi, B., and Zeng, Y. C. (1994). Neuroanatomy of aging brain. Influence of treatment with L-deprenyl. Ann N Y Acad Sci 717, 33–44.

Anderson, A. J., Su, J. H., and Cotman, C. W. (1996). DNA damage and apaptosis in Alzheimer's disease: colocalization with c-Jun immunoreactivity, relationship to brain area and the effect of postmortem delay. J Neurosci. 16, 1710–1719.

Ansari, K. S., Yu, P. H., Kruck, T. P., and Tatton, W. G. (1993). Rescue of axotomized immature rat facial motoneurons by R(−)-deprenyl: stereospecificity and independence from monoamine oxidas inhibition. J Neurosci 13, 4042–53.

Arends, M. J., Morris, R. G., and Wyllie, A. H. (1990). Apoptosis. The role of the endonuclease. Am J Pathol 136, 593–608.

Armstrong, R. C., Aja, T. J., Hoang, K. D., Gaur, S., Bai, X., Alnemri, E. S., Litwack, G., Karanewsky, D. S., Fritz, L. C., and Tomaselli, K. J. (1997). Activation of the CED3/ICE-related protease CPP32 in cerebellar granule neurons undergoing apoptosis but not necrosis. J Neurosci 17, 553–562.

Ballabriga, J., Pellise, A., and Ferrer, I. (1997). L-deprenyl does not reduce brain damage in global forebrain ischemia in adult gerbils (Meriones ungiculatus). J Neurol Sci 148, 1–5.

Ballotti, R., Nielsen, F. C., Pringle, N., Kowalski, A., Richardson, W. D., Van Obberghen, E., and Gammeltoft, S. (1987). Insulin-like growth factor I in cultured rat astrocytes: expression of the gene, and receptor tyrosine kinase. Embo J 6, 3633–9.

Baron Van Evercooren, A., Olichon Berthe, C., Kowalski, A., Visciano, G., and Van Obberghen, E. (1991). Expression of IGF-I and insulin receptor genes in the rat central nervous system: a developmental, regional, and cellular analysis. J Neurosci Res 28, 244–53.

Barres, B. A., Hart, I. K., Coles, H. S., Burne, J. F., Voyvodic, J. T., Richardson, W. D., and Raff, M. C. (1992). Cell death and control of cell survival in the oligodendrocyte lineage. Cell 70, 31–46.

Barres, B. A., Hart, I. K., Coles, H. S., Burne, J. F., Voyvodic, J. T., Richardson, W. D., and Raff, M. C. (1992). Cell death in the oligodendrocyte lineage. J Neurobiol 23, 1221–30.

Barres, B. A., and Raff, M. C. (1994). Control of oligodendrocyte number in the developing rat optic nerve. Neuron 12, 935–42.

Barres, B. A., Schmid, R., Sendnter, M., and Raff, M. C. (1993). Multiple extracellular signals are required for long-term oligodendrocyte survival. Development 118, 283–95.

Bartlett, W. P., Knapp, P. E., and Skoff, R. P. (1988). Glial conditioned medium enables jimpy oligodendrocytes to express properties of normal oligodendrocytes: production of myelin antigens and membranes. Glia 1, 253–9.

Bartlett, W. P., Li, X. S., Williams, M., and Benkovic, S. (1991). Localization of insulin-like growth factor-1 mRNA in murine central nervous system during postnatal development. Dev Biol 147, 239–50.

Baskin, D. G., Porte, D., Jr., Guest, K., and Dorsa, D. M. (1983). Regional concentrations of insulin in the rat brain. Endocrinology 112, 898–903.

Batistatou, A., and Greene, L. A. (1993). Internucleosomal DNA cleavage and neuronal cell survival/death. J Cell Biol 122, 523–32.

Baxter, R. C. (1991). Biochemical characterization of insulin-like growth factor binding proteins. Acta Endocrinol. (Copenh.) 124(Suppl.2), 33–40.

Behar, T., McMorris, F. A., Novotny, E. A., Barker, J. L., and Dubois Dalcq, M. (1988). Growth and differentiation properties of O-2A progenitors purified from rat cerebral hemispheres. J Neurosci Res 21, 168–80.

Bellamy, C. O. (1997). p53 and Apoptosis. Br. Med. Bull. 53, 522–538.

Benchaoui, H. A., and McKellar, Q. A. (1996). Interaction between fendendazole and piperonyl butoxide: pharmacokinetic and pharmacodynamic implications. J Pharm Pharmacol 48, 753–9.

Bernardi, P., Broekemeier, K. M., and Pfeiffer, D. R. (1994). Recent progress on regulation of the mitochondrial permeability transition pore; A cyclosporin-sensitive pore in the inner mitochondrial membrane. J. Bioenerget. Biomemb. 26, 509–517.

Biagini, G., Frasoldati, A., Fuxe, K., and Agnati, L. F. (1994). The concept of astrocyte-kinetic during in the treatment of neurodegenarative diseases: evidence for L-deprenyl- induced activation of reactive astrocytes. Neurochem Int 25, 17–22.

Biagini, G., Zoli, M., Fuxe, K., and Agnati, L. F. (1993). L-deprenyl increases GFAP immunoreactivity selectively in activated astrocytes in rat brain. Neuroreport 4, 955–8.

Bohannon, N. J., Corp, E. S., Wilcox, B. J., Figlewicz, D. P., Dorsa, D. M., and Baskin, D. G. (1988). Localization of bindings sites for insulin-like growth factor-I (IGF-I) in the rat brain by quantitative autoradiography. Brain Res 444, 205–13.

BossyWetzel, E., Bakiri, L., and Yaniv, M. (1997). Induction of apoptosis by the transcription factor c-Jun. EMBO Journal 16, 1695–1709.

Bottentein, J. E. (1986). Growth requirements in vitro of oligodendrocyte cell lines and neonatal rat brain oligodendrocytes. Proc Natl Acad Sci U S A 83, 1955–9.

Bottenstein, J. E., Hunter, S. F., and Seidel, M. (1988). CNS neuronal cell line-derived factors regualte gliogenesis in neonatal rat brain cultures. J Neurosci Res 20, 291–303.

Bradford, M. M. (1976). A rapid and sensitive method for the quantitation of microgram quantities of protein utilizing the principle of protein-dye binding. Anal Biochem 72, 248–54.

Brown, S. B., Bailey, K., and Savill, J. (1997). Actin is cleaved duing consitutive apoptosis. Biochemical Journal 323, 233–237.

Bruck, W., Schmied, M., Suchanek, G., Bruck, Y., Breitscopf, H., Poser, S., Piddlesden, S., and Lassmann, H. (1994). Oligodendrocytes in the early course of multiple sclerosis. Ann Neurol 35, 65–73.

Buys, Y. M., Trope G. E., Tatton WG (1995). (–)-Deprenyl increases the survival of rat retinal ganglion cells after optic nerve crush. Curr Eye Res 14, 199–26.

Carayon, P., Portier, M., Dussossoy, D., Bord, A., Petipretre, G., Canat, X., Le Fur, G., and Casellas, P. (1996). Involvement of peripheral benzodiazepine receptors in the protection of hematopoietic cells against oxygen radical damage. Blood 87, 3170–3178.

Caroni, P., and Schwab, M. E. (1988). Antibody against myelin-associated inhibitor of neurite growth neutralized nonpermissive substrate properties of CNS white matter. Neuron 1, 85–96.

Carrillo, M. C., Kanai, S., Nokubo, M., and Kitani, K. (1991). (–)-deprenyl induces activities of both superoxide dismutase and catalase but not of glutathione peroxidase in the striatum of yound male rats. Life Sci 48, 517–21.

Carrillo, M.C., Kitani, K., Kanai, S., Sato, Y., and Ivy, G. O. (1992). The ability of (–)deprenyl to increase superoxide dismutase activities in the rat is tissue and brain region selective. Life Sci 50, 1985–92.

Carson, M. J., Behringer, R. R., Brinster, R. L., and McMorris, F. A. (1993). Insulin-like growth factor I increase brain growth and central nervous system myelination in transgenic mice. Neuron 10, 729–40.

Chalmers-Redman, R. M. E., Fraser, A. D., Ju, W. J. H., Wadia, J., Tatton, N. A., and Tatton, W. G. (1996). Mechanisms of nerve cell death: Apoptosis or necrosis after cerebral ischemia. In Neuroprotective Agents and Cerebral Ischemia, A. Coss and G. Richards, eds. (London: Academic Press), pp. 1–25.

Chernyak, B. V., and Bernardi, P. (1996). The mitochondrial permeability pore is modulated by oxidative agents through both pyridine nucleotides and glutathione at two separates sites. Eur. J. Biochem. 238, 623–630.

Cohen, G., Pasik, P., Cohen, B., Leist, A., Mytilineau, C., and Yahr, M. D. (1984). Pargyline and deprenyl prevent the neurotoxicity of 1-methyl-4-phenyl -1,2,3,6- tetrahydropyridine (MPTP) in monkeys. Eur.J.Pharmacol. 106.

Cohen, G. M. (1997). Caspases: the executioners of apoptosis. Biochemical Journal 326, 1–16.

Curtis, R., Cohen, J., Fok Seang, J., Hanley, M. R., Gregson, N. A., Reynolds, R., and Wilkin, G. P. (1988). Development of macroglial cells in rat cerebellum. I. Use of antibodies to follow early in vivo development and migration of oligodendrocytes. J Neurocytol 17, 43–54.

Darzynkiewicz, Z., Bruno, S., Del Bino, G., Gorczyca., W., Hotz, M. A., Lassota, P., and Traganos, F. (1992). Features of apoptotic cells measured by flow cytometry. Cytometry 13, 795–808.

Depraetere, V., and Goistein, P. (1997). Fas and other cell death signaling pathways. Semin Immunol 9, 93–107.

Deshpande, J., Bergstedt, K., Linden, T., Kalimo, I—I., and Wieloch, T. (1992). Ultrastructural changes in the hippocampal CA1 region following transient cerebral ischemia: evidence against programmed cell death. Exp Brain Res 88, 9 1–105.

Dragunow, M., and Preston, K. (1995). The role of inducible transcription factors in apoptotic nerve cell death. Brain Res. Rev. 21, 1–28.

D'Souza, S. D., Alinauskas, K. A., and Antel, J. P. (1996). Ciliary neurotrophic factor selectively protects human oligodendrocytes from tumor necrosis factor-mediated injury. J Neurosci Res 43, 289–98.

Du, Y. S., Bales, K. R., Dodel, R. C., HamiltonByrd, E., Horn, J. W., Czilli, D. L., Simmons, L. K., Ni, B. H., and Paul, S. M. (1997). Activation of a caspase 3-related cysteine protease is required for glutamate-mediated apoptosis of cultured cerebellar granule neurons. Proc Natl Acad Sci U S A 94, 11657–11662.

Dubois Dalcq, M. (1987). Characterization of a slowly proliferative cell along the oligodendrocyte differentiation pathway. Embo J 6, 2587–95.

Dubois Dalcq, M., Behar, T., Hudson, L., and Lazzarini, R. A. (1986). Emergence of three myelin proteins in oligodendrocytes cultured without neurons. J Cell Biol 102, 384–92.

Eastman, A. (1993). Apoptosis: a product of programmed and unprogrammed cell death. Toxicol Appl Pharmacol 121, 160–4.

Eccleston, P. A., and Silberberg, D. H. (1984). The differentiation of oligodendrocytes in a serum-free hormone-supplemented medium. Brain Res 318, 1–9.

Eisenbarth, G. S., Walsh, F. S., and Nirenberg, M. (1979). Monoclonal antibody to a plasma membrane antigen of neurons. Proc Natl Acad Sci U S A 76, 49 13–7.

Ekblom, J., Jossan, S. S., Ebendal, T., Soderstrom, S., Oreland, L., and Aquilonius, S. M. (1994). mRNA expression of neurotrophins and members of the trk family in the rat brain after treatment with L-deprenyl [letter]Acta Neurol Scand 89, 147–8.

Ellis, R. E., Yuan, J. Y., and Horvitz, H. R. (1991). Mechanisms and functions of cell death. Annu Rev Cell Biol 7, 663–98.

Espinosa de los Monteros, A., Roussel, G., Neskovic, N. M., and Nussbaum, J. L. (1988). A chemically defined medium for the culture of mature oligodendrocytes. J Neurosci Res 19, 202–11.

Espinosa de los Monteros, A., Roussel, G., and Nussbaum, J. L. (1986). A procedure for long-term culture of oligodendrocytes. Brain Res 389, 117–25.

Fang, J., Zuo, D. M., and Yu, P. H. (1995). Lack of protective effect of R(–)-deprenyl on programmed cell death of mouse thymocytes induced by dexamethasone. Life Sciences 57, 15–22.

Fesus, L., Davies, P. J. A., and Piacentini, M. (1991). Apoptosis: molecular mechanisms of programmed cell death. Eur. J. Cell Biol. 231, 119–134.

Finch, C. E. (1993). Neuron atrophy during aging: programmed or sporadic? [see comments]. Trends Neurosci 16, 104–10.

Freeman, R. S., Estus, S., and Johnson, E. M., Jr. (1994). Analysis of cell cycle-related gene expression in postmitotic neurons: selective induction of Cyclin D1 during programmed cell death. Neuron 12, 343–55.

Gao, C. Y., and Zelenka, P. 5. (1995). Induction of cyclin B and HI kinase activity in apoptotic PC12 cells. Exp Cell Res 219, 6 12–8.

Gard, A. L., and Pfeiffer, S. E. (1989). Oligodendrocyte progenitors isolated directly from developing telencephalon at a specific phenotypic stage: myelinogenic potential in a defined environment. Development 106, 119–32.

Gard, A. L., and Pfeiffer, S. E. (1990). Two proliferative stages of the oligodendrocyte lineage (A2B5+04- and 04+GalC-) under different mitogenic control. Neuron 5, 615–25.

Gillardon, F., Wickert, H., and Zimmermann, M. (1995). Up-regulation of bax and down- regulation of bcl-2 is associated with kainate-induced apoptosis in mouse brain. Neurosci Lett 192, 85–8.

Glucksmann, A. (1951). Cell death in normal vertebrate ontogeny. Biol. Rev. 26, 59–86.

Gow, A., Southwood, C. M., and Lazzarini, R. A. (1998). Disrupted proteolipid protein trafficking results in oligodendrocyte apoptosis in an animal model of Pelizaeus-Merzbacher disease. J Cell Biol 140, 925–34.

Graber, M. N., Alfonso, A., and Gill, D. L. (1997). Recovery of Ca2+ pools and growth in Ca2+ pool-depleted cells is mediated by specific epoxyeicosatrienoic acids derived from arachidonic acid. J Biol Chem 272, 29546–53.

Greenlund, L. J. S., Deckwerth, T. L., and Johnson, E. M. (1995). Superoxide Dismutase Delays Neuronal Apoptosis: A Role for Reactive Oxygen Species in Programmed Neuronal Death. Neuron 14, 303–315.

Gressner, A. M., Labme, B., and Roth, 5. (1997). Attenuation of TGF-beta-induced apoptosis in primary cultures of hepatocytes by calpain inhibitors. Biochemical and Biophysical Research Communications 231, 457–462.

Han, V. K., Lauder, J. M., and AJ, D. E. (1987). Characterization of somatomedin/insulin-like growth factor receptors and correlation with biologic action in cultured neonatal rat astroglial cells. J Neurosci 7, 501–11.

Hart, I. K., Richardson, W. D., Bolsover, S. R., and Raff, M. C. (1989). PDGF and intracellular signaling in the timing of oligodendrocyte differentiation. J Cell Biol 109, 341 1–7.

Hartley, A., Stone, J. M., Heron, C., Cooper, J. M., and Schapira, A. H. (1994). Complex I inhibitors induce dose-dependent apoptosis in PCl2 cells: relevance to Parkinson's disease. J Neurochem 63, 1987–90.

Haupt, Y., Barak, Y., and Oren, M. (1996). Cell type specific inhibition of p53 mediated apoptosis by mdm2. EMBO J. 15, 1598–1606.

Havrankova, J., Schmechel, D., Roth, J., and Brownstein, M. (1978). Identification of insulin in rat brain. Proc Natl Acad Sci U S A 75, 5737–41.

Hefti, F. (1986). Nerve growth factor promotes survival of septal cholinergic neurons after fimbrial transections. J Neurosci 6, 2155–62.

Heikkila, R. E., Manzino, L., Cabbat, F. S., and Duvoisin, R. C. (1984). Protection against the dopaminergic neurotoxicity of 1-methyl-4-phenyl-1,2,5,6-tetrahydropyridine by monoamine oxidase inhibitors. Nature 311, 467–9.

Heinonen, E. H., Anttila, M. I., and Lainmintausta, R. A. (1994). Pharmacokinetic aspects of 1-deprenyl (selegiline) and its metabolites. Clin Pharmacol Ther 56, 742–9.

Henderson, J. T., Seniuk, N. A., and Roder, J. C. (1994). Localization of CNTF immunoreactivity to neurons and astroglia in the CNS. Brain Res Mol Brain Res 22, 15 1–65.

Hockenbery, D. M. (1992). The bcl-2 oncogene and apoptosis. Semin Inimunol 4, 413–20.

Hockenbery, D. M., Oltvai, Z. N., Yin, X. M., Milliman, C. L., and Korsmeyer, S. J. (1993). Bcl–2 functions in an antioxidant pathway to prevent apoptosis. Cell 75, 241–51.

Hsu, Y. T., Wolter, K. G., and Youle, R. J. (1997). Cytosol-to-membrane redistribution of Bax and Bcl-X-L during apoptosis. Proc Natl Acad Sci U S A 94, 3668–3672.

Hunter, S. F., and Bottenstein, J. E. (1990). Growth factor responses of enriched bipotential glial progenitors. Brain Res Dev Brain Res 54, 235–48.

Ishitani, R., and Chuang, D. M. (1996). Glyceraldehyde-3-phosphate dehydrogenase antisense oligodeoxynucleotides protect against cytosine arabinonucleoside-induced apoptosis in cultured cerebellar neurons. Proc NatI Acad Sci U S A 93, 9937–9941.

Ishitani, R., Kimura, M., Sunaga, K., Katsube, N., Tanaka, M., and Chuang, D. M. (1996). An antisense oligodeoxynucleotide to glyceraldehyde-3-phosphate dehydrogenase blocks age-induced apoptosis of mature cerebrocortical neurons in culture. Journal of Pharmacology and Experimental Therapeutics 278, 447–454.

Ishitani, R., Sunaga, K., Hirano, A., Saunders, P., Katsube, N., and Chuang, D. M. (1996). Evidence that glyceraldehyde-3-phosphate dehydrogenase is involved in age- induced apoptosis in mature cerebellar neurons in culture. J Neurochem 66, 928–935.

Ishitani, R., Sunaga, K., Tanaka, M., Aishita, H., and Chuang, D. M. (1997). Overexpression of glyceraldehyde-3-phosphate dehydrogenase is involved in low K+- induced apoptosis but not necrosis of cultured cerebellar granule cells. Molecular Pharmacology 51, 542–550.

Ishizaki, Y., Burne, J. F., and Raff, M. C. (1994). Autocrine signals enable chondrocytes to survive in culture. J Cell Biol 126, 1069–77.

Ishizaki, Y., Cheng, L., Mudge, A. W., and Raff, M. C. (1995). Programmed cell death by default in embryonic cells, fibroblasts, and cancer cells. Mol Biol Cell 6, 1443–58.

Iwasaki, Y., ikceda, K., Shiojima, T., Kobayashi, T., Tagaya, N., and Kinoshita, M. (1996). Deprenyl and pergolide rescue spinal motor neurons from axotomy-induced neuronal death in the neonatal rat. Neurological Research 18, 168–170.

Jackson, K. F., and Duncan, I. D. (1988). Cell kinetics and cell death in the optic nerve of the myelin deficient rat. J Neurocytol 17, 657–70.

Jacobson, M. D., Burne, J. F., King, M. P., Miyashita, T., Reed, J. C., and Raff, M. C. (1993). Bcl–2 blocks apoptosis in cells lacking mitochondrial DNA. Nature 361, 365–9.

Johnson, E. M., Greenlund, L. J. S., Akins, P. T., and Hsu, C. Y. (1995). Neuronal apoptosis: Current understanding of molecular mechanisms and potential role in ischemic brain injury. Journal of Neurotrauma 12, 843–852.

Jordan, J., Galindo, M. F., Prehn, J. H. M., Weichselbaum, R. R., Beckett, M., Ghadge, G. D., Roos, R. P., Leiden, J. M., and Miller, R. J. (1997). P53 expression induces apoptosis in hippocampal pyramidal neuron cultures. J Neurosci 17, 1397–1405.

Ju, W. Y., Holland, D. P., and Tatton, W. G. (1994). (-)-Deprenyl alters the time course of death of axotomized facial motoneurons and the hypertrophy of neighboring astrocytes in immature rats. Exp Neurol 126, 233–46.

Kagawa, T., Ikenaka, K., Inoue, Y., Kuriyama, S., Tsujii, T., Nakao, J., Nakajima, K., Aruga, J., Okano, H., and Mikoshiba, K. (1994). Glial cell degeneration and hypomyelination caused by overexpression of myelin proteolipid protein gene. Neuron 13, 427–42.

Kappy, M., Sellinger, S., and Raizada, M. (1984). Insulin binding in four regions of the developing rat brain. J Neurochem 42, 198–203.

Kerr, J. F., Wyllie, A. H., and Currie, A. R. (1972). Apoptosis: a basic biological phenomenon with wide-ranging implications in tissue kinetics. Br J Cancer 26, 239–57.

Kerr, J. F. R. (1965). A histochemical study of hypertrophy and ischemic injury of rat lver with specific references to changes in lysosomes. J. Pathol. Bacteriol. 90, 419–435.

Kerr, J. F. R. (1971). Shrinkage necrosis: a distinct form of cell death. J. Pathol. 105, 13–20.

Kharbanda, S., Pandey, P., Schofield, L., Israels, S., Roncinske, R., Yoshida, K., Bharti, A., Yuan, Z. M., Saxena, S., Weichselbaum, R., Nalin, C., and Kufe, D. (1997). Role for Bcl-xL as an inhibitor of cytosolic cytochrome C accumulation in DNA damage- induced apoptosis. Proc Natl Acad Sci U S A 94, 6939–42.

Kharlamov, A., Joo, J. Y., Uz, T., and Manev, H. (1997). Cycloheximide reduces the size of lesion caused in rats by a photothrombotic model of brain injury. Neurological Research 19, 92–96.

Kiran, B., Rao, B. S. S., Raju, T. R., and Bindu, P. N. (1998). Spinal cord ischaemia- induced excitotoxicity and neurodegeneration: attenuation by (–)-deprenyl and magnesium sulfate. Medical Science Research 26, 89–92.

Kitani, K., Kanai, S., Carrillo, M. C., and Ivy, G. O. (1994). (–)Deprenyl increases the life span as well as activities of superoxide dismutase and catalase but not of glutathione peroxidase in selective brain regions in Fischer rats. Ann N Y Acad Sci 717, 60–71.

Knapp, P. E., SkoffRP, Sprinkle TJ (1988). Differential expression of galactocerebroside, myelin basic protein, and 2',3'-cyclic nucleotide 3'- phosphohydrolase during development of oligodendrocytes in vitro. J Neurosci Res 21, 249–59.

Knapp, P. E., Bartlett, W. P., and Skoff, R. P. (1987). Cultured oligodendrocytes mimic in vivo phenotypic characteristics: cell shape, expression of myelin-specific antigens, and membrane production. Dev Biol 120, 356–65.

Knollema, S., Aukema, W., Hom, H., Korf, J., and TerHorst, G. J. (1995). L-deprenyl reduces brain damage in rats exposed to transient hypoxia-ischemia. Stroke 26, 1883–1887.

Korsmeyer, S. J., Shutter, J. R., Veis, D. J., Merry, D. E., and Oltvai, Z. N. (1993). Bcl-2/Bax: a rheostat that regulates an anti-oxidant pathway and cell death. Semin Cancer Biol 4, 327–32.

Koutsilieri, E., Chen, T. S., Rausch, W. D., and Riederer, P. (1996). Selegiline is neuroprotective in primary brain cultures treated with 1-methyl-4-phenylpyridinium. EurJPharmacol 306, 181–186.

Koutsilieri, E., OCallaghan, J. F. X., Chen, T. S., Riederer, P., and Rausch, W. D. (1994). Selegiline enhances survival and neurite outgrowth of MPP(+)-treated dopaminergic neurons. Eur J Pharmacol (Molecular Pharmacology Section) 269, R3–R4.

Kragten, E., Lalande, I., Zimmermann, K., Roggo, S., Schindler, P., Miüller, D., van Gostrum, J., Waldmeier, P., and Fiirst, P. (1998). Glyceraldehyde-3-phosphate Dehydrogenase, the Putative Target of the Antiapoptotic Compounds CGP 3466 and R- (–)-Deprenyl. J Biol Chem 273, 5821–5828.

Krajewska, M., Wang, H. G., Krajewski, S., Zapata, J. M., Shabaik, A., Gascoyne, R., and Reed, J. C. (1997). Immunohistochemical analysis of in vivo patterns of expression of CPP32 (Caspase-3), a cell death protease. Cancer Research 57, 1605–1613.

Kranenburg, O., van der Eb, A. J., and Zantema, A. (1996). Cyclin Dl is an essential mediator of apoptotic neuronal cell death. Embo J 15, 46–54.

Kroemer, G., Zamzami, N., and Susin, S. A. (1997). Mitochondrial control of apoptosis. Immunology Today 18, 44–51.

Lahtinen, H., Koistinaho, J., Kauppinen, R., Haapalinna, A., Keinanen, R., and Sivenius, J. (1997). Selegiline treatment after transient global ischemia in gerbils enhances the survival of CA1 pyramidal cells in the hippocampus. Brain Res 757, 260–267.

Lai, C. T., Zuo, D. M., and Yu, P. H. (1994). Is brain superoxide dismutase activity increased following chronic treatment with 1-deprenyl? J Neural Transmission Suppl., 221–229.

Langston, J. W., Irwin, I., Langston, E. B., and Forno, L. S. (1984). Pargyline prevents MPTP-induced parkinsonism in primates. Science 225, 1480–2.

Le, W. D., Jankovic, J., Xie, W. J., Kong, R., and Appel, S. H. (1997). (–)-Deprenyl protection of 1-methyl-4 phenylpyridium ion (MPP(+))-induced apoptosis independent of MAO-B inhibition. Neurosci. Lett. 224, 197–200.

Lees, M. B., Brostoff SW. (1984). Proteins of myelin., Morell-P., ed. (New York: Plenum Press).

Levi, G., Aloisi, F., and Wilkin, G. P. (1987). Differentiation of cerebellar bipotential glial precursors into oligodendrocytes in primary culture: developmental profile of surface antigens and mitotic activity. J Neurosci Res 18, 407–17.

LeVine, S. M., and Goldman, J. E. (1988). Spatial and temporal patterns of oligodendrocyte differentiation in rat cerebrum and cerebellum. J Comp Neurol 277, 441–55.

Li, F., Srinivasan, A., Wang, Y., Armstrong, R. C., Tomaselli, K. J., and Fritz, L. C. (1997). Cell specific induction of apoptosis by microinjection of cytochrome c. J. Biol. Chem. 272, 30299–30305.

Li, X. M., Juorio, A. V., Paterson, I. A., Zhu, M. Y., and Boulton, A. A. (1992). Specific irreversible monoamine oxidase B inhibitors stimulate gene expression of aromatic L- amino acid decarboxylase in PCl2 cells. J Neurochem 59, 2324–7.

Li, X. M., Juorio, A. V., Qi, J., and Boulton, A. A. (1998). L-deprenyl potentiates NGF- induced changes in superoxide dismutase mRNA in PC12 cells. J Neurosci Res 53, 235–238.

Li, X. M., Qi, J., Juorio, A. V., and Boulton, A. A. (1997). Reciprocal regulation of the content of aromatic 1-amino acid decarboxylase and tyrosine hydroxylase mRNA by NGF in PC12 cells. J Neurosci Res 47, 449–454.

Li, X. M., Qi, J., Juorio, A. V., and Boulton, A. A. (1993). Reduction in glial fibrillary acidic protein mRNA abundance induced by (–)-deprenyl and other monoamine oxidase B inhibitors in C6 glioma cells. J Neurochem 61, 1573–6.

Lillien, L. E., and Raff, M. C. (1990). Analysis of the cell—cell interactions that control type-2 astrocyte development in vitro. Neuron 4, 525–34.

Litligow, T., van Driel, R., Bertram, J. F., and Strasser, A. (1994). The protein product of the oncogene bcl-2 is a component of the nuclear envelope, the endoplasmic reticulum, and the outer mitochondrial membrane. Cell Growth Differ 5, 411–7.

Liu, J. P., Baker, J., Perkins, A. S., Robertson, E. J., and Efstratiadis, A. (1993). Mice carrying null mutations of the genes encoding insulin-like growth factor I (Igf-1) and type 1 IGF receptor (Igflr). Cell 75, 59–72.

Liu, X. S., Kim, C. N., Yang, J., Jemmerson, R., and Wang, X. D. (1996). Induction of apoptotic program in cell-free extracts: Requirement for dATP and cytochrome c. Cell 86, 147–157.

Louis, J. C., Magal, E., Takayama, S., and Varon, 5. (1993). CNTF protection of oligodendrocytes against natural and tumor necrosis factor-induced death. Science 259, 689–92.

Lumsden, C. E. (1971). The immunogenesis of the multiple sclerosis plaque. Brain Res 28, 365–90.

Magyar, K., Szende, B., Lengyel, J., Tarczali, J., and Szatmary, I. (1998). The neuroprotective and neuronal rescue effects of (–)-deprenyl. J Neural Transm. (Supplement), 109–123.

Marchetti, P., Castedo, M., Susin, S. A., Zamzami, N., Hirsch, T., Macho, A., Haeffner, A., Hirsch, F., Geuskens, M., and Kroemer, G. (1996). Mitochondrial permeability transition is a central coordinating event of apoptosis. J Exp Med 184, 1155–1160.

Martin, D. P., Ito, A., Horigome, K., Lampe, P. A., and Johnson, E. M. (1992). Biochemical Characterization of Programmed Cell Death in NGF-Deprived Sympathetic Neurons. J Neurobiol 23, 1205–1220.

Matsuyama, T., Hata, R., Yamamoto, Y., Tagaya, M., Akita, H., Uno, H., Furuyama, J., and Sugita., M. (1995). Localization of Fas antigen mRNA induced in postischemic murine forebrain by in situ hybridization. Mol Brain Res 34, 166–172.

Mattson, M. P., Zhang, Y., and Bose, S. (1993). Growth factors prevent mitochondrial dysfunction, loss of calcium homeostasis, and cell injury, but not ATP depletion in hippocampal neurons deprived of glucose. Exp Neurol 121, 1–13.

McCarthy, K. D., deVellis J (1980). Preparation of seperate astroglial and oligodendroglial cell cultures from rat cerebral tissue. J Cell Biol 85, 890–902.

McKinnon, R. D., Matsui, T., Dubois Dalcq, M., and Aaronson, S. A. (1990). FGF modulates the PDGF-driven pathway of oligodendrocyte development. Neuron 5, 603–14.

McMorris, F. A. (1983). Cyclic AMP induction of the myelin enzyme 2',3'-cyclic nucleotide 3'-phosphohydrolase in rat oligodendrocytes. J Neurochem 41, 506–15.

McMorris, F. A., and Dubois Dalcq, M. (1988). Insulin-like growth factor I promotes cell proliferation and oligodendroglial commitment in rat glial progenitor cells developing in vitro. J Neurosci Res 21, 199–209.

McMorris, F. A., Furlanetto, R. W., Mozell, R. L., Carson, M. J., and Raible, D. W. (1990). Regulation of oligodendrocyte development by insulin-like growth factors and cyclic nucleotides. Ann N Y Acad Sci 605, 101–9.

McMorris, F. A., Mozell, R. L., Carson, M. J., Shinar, Y., Meyer, R. D., and Marchetti, N. (1993). Regulation of oligodendrocyte development and central nervous system myelination by insulin-like growth factors. Ann N Y Acad Sci 692, 321–34.

McMorris, F. A., Smith, T. M., DeSalvo, S., and Furlanetto, R. W. (1986). Insulin-like growth factor Isomatomedin C: a potent inducer of oligodendrocyte development. Proc Natl Acad Sci U S A 83, 822–6.

Merry, D. E., and Korsmeyer, S. J. (1997). Bcl-2 gene family in the nervous system. Annu Rev Neurosci 20, 245–67.

Mesner, P. W., Winters, T. R., and Green, S. H. (1992). Nerve growth factor withdrawal- induced cell death in neuronal PC12 cells resembles that in sympathetic neurons. J Cell Biol 119, 1669–80.

Migheli, A., Cavalla, P., Marino, S., and Schiffer, D. (1994). A study of apoptosis in normal and pathologic nervous tissue after in situ end-labeling of DNA strand breaks. J Neuropathol Exp Neurol 53, 606–16.

Miller, R. H., David, S., Patel, R., Abney, E. R., and Raff, M. C. (1985). A quantitative immunohistochemical study of macroglial cell development in the rat optic nerve: in vivo evidence for two distinct astrocyte lineages. Dev Biol 111, 35–41.

Mirsky, R., Winter, J., Abney, E. R., Pruss, R. M., Gavrilovic, J., and Raff, M. C. (1980). Myelin-specific proteins and glycolipids in rat Schwann cells and oligodendrocytes in culture. J Cell Biol 84, 483–94.

Mochizuki, H., Nakamura, N., Nishi, K., and Mizuno, Y. (1994). Apoptosis is induced by 1-methyl-4-phenylpyrldinium ion (MPP+) in ventral mesencephalic-striatal co-culture in rat. Neurosci Lett 170, 191–4.

Mozell, R. L., and McMorris, F. A. (1991). Insulin-like growth factor I stimulates oligodendrocyte development and myelination in rat brain aggregate cultures. J Neurosci Res 30, 382–90.

Mytilineou, C., and Cohen, G. (1985). Deprenyl protects dopamine neurons from the neurotoxic effect of 1-methyl-4-phenylpyridiium ion. J Neurochem 45, 195 1–3.

Mytilineou, C., Radcliffe, P. M., and Olanow, C. W. (1997). L-(–)-desmethylselegiline, a metabolite of selegiline [L-(–)-deprenyl], protects mesencephalic dopamine neurons from excitotoxicity in vitro. J Neurochem 68, 434–6.

Nath, R., Raser, K. J., McGinnis, K., Nadimpalli, R., Stafford, D., and Wang, K. K. W. (1996). Effects of ICE-like protease and calpain inhibitors on neuronal apoptosis. Neuroreport 8, 249–255.

Newmeyer, D. D., Farschon, D. M., and Reed, J. C. (1994). Cell-free apoptosis in Xenopus egg extracts: inhibition by Bcl-2 and requirement for an organelle fraction enriched in mitochondria [sec comments]. Cell 79, 353–64.

Noble, M., Murray, K., Stroobant, P., Waterfield, M. D., and Riddle, P. (1988). Platelet- derived growth factor promotes division and motility and inhibits premature differentiation of the oligodendrocyteltype-2 astrocyte progenitor cell. Nature 333, 560–2.

Norton, W. T., and Farooq, M. (1993). Differentiation of glial precursor cells from developing rat brain in vitro. Brain Res Dev Brain Res 72, 193–202.

Oh, C., Murray, B., Bhattachaiya, N., Holland, D., and Tatton, W. G. (1994). (–)- Deprenyl alters the survival of adult murine facial motoneurons after axotomy: increases in vulnerable C57BL strain but decreases in motor neuron degeneration mutants. J Neurosci Res 38, 64–74.

Olanow, C. W., and Tatton, W. G. (1999). Etiology And Pathogenesis Of Parkinson's disease. Ann. Rev. Neurosci. 22, 123–144.

Oppenheim, R. W. (1991). Cell death during development of the nervous system. Annu Rev Neurosci 14, 453–501.

Oppenheim, R. W., Maderdrut, J. L., and Wells, D. J. (1982). Cell death of motoneurons in the chick embryo spinal cord. VI. Reduction of naturally occurring cell death in the thoracolumbar column of Terni by nerve growth factor. J Comp Neurol 210, 174–89.

Oppenheim, R. W., Prevette, D., Tytell, M., and Homma, S. (1990). Naturally occurring and induced neuronal death in the chick embryo in vivo requires protein and RNA synthesis: evidence for the role ofcell death genes. Dev Biol 138, 104–13.

Paterson, I. A., Barber, A. J., Gelowitz, D. L., and Voll, C. (1997). (–)Deprenyl reduces delayed neuronal death of hippocampal pyramidal cells. Neuroscience and Biobehavioral Reviews 21, 181–186.

Paterson, I. A., Zhang, D., Warrington, R. C., and Boulton, A. A. (1998). R-Deprenyl and R-2-Heptyl-N-methylpropargylamine prevent apoptosis in cerebellar granule neurons induced by cytosine arabinoside but not low extracellular potassium. Journal of Neurochemistiy 70, 515–523.

Petito, C. K., and Roberts, B. (1995). Evidence of apoptotic cell death in HIV encephalitis. Am J Pathol 146, 1121–30.

Polyak, K., Xia, Y., Zweier, J. L., Kinzler, K. W., and Vogelstein, B. (1997). A model for p53-induced apoptosis. Nature, 300–305.

Pringle, N. P., and Richardson, W. D. (1993). A singularity of PDGF alpha-receptor expression in the dorsoventral axis of the neural tube may define the origin of the oligodendrocyte lineage. Development 117, 525–33.

Przedborski, S., Kostic, V., Jacksonlewis, V., Naini, A. B., Simonetti, S., Fahn, S., Carlson, E., Epstein, C. J., and Cadet, J. L. (1992). Transgenic Mice with Increased Cu/Zn-Superoxide Dismutase Activity Are Resistant to N-methyl-4-phenyl-1,2,3,6- tetrahydropyridine-induced Neurotoxicity. J Neurosci 12, 1658–1667.

Rabizadeh, S., Gralla, E. B., Borchelt, D. R., Gwinn, R., Valentine, J. S., Sisodia, S., Wong, P., Lee, M., Hahn, H., and Bredesen, D. E. (1995). Mutations associated with amyotrophic lateral sclerosis convert superoxide dismutase from an antiapoptotic gene to a proapoptotic gene: studies in yeast and neural cells. Proc Natl Acad Sci U S A 92, 3024–8.

Raff, M. C. (1989). Glial cell diversification in the rat optic nerve. Science 243, 1450–5.

Raff, M. C. (1992). Social controls on cell survival and cell death. Nature 356, 397–400.

Raff, M. C., Barres, B. A., Bume, J. F., Coles, H. S., Ishizaki, Y., and Jacobson, M. D. (1993). Programmed cell death and the control of cell survival: lessons from the nervous system. Science 262, 695–700.

Raff, M. C., Fields, K. L., Hakomori, S. I., Mirsky, R., Pruss, R. M., and Winter, J. (1979). Cell-type-specific markers for distinguishing and studying neurons and the major classes of glial cells in culture. Brain Res 174, 283–308.

Raff, M. C., Lillien, L. E., Richardson, W. D., Burne, J. F., and Noble, M. D. (1988). Platelet-derived growth factor from astrocytes drives the clock that times oligodendrocyte development in culture. Nature 333, 562–5.

Raff, M. C., Miller, R. H., and Noble, M. (1983). A glial progenitor cell that develops in vitro into an astrocyte or an oligodendrocyte depending on culture medium. Nature 303, 390–6.

Ragaiey, T., Ma, J. X., Jiang, W. J., Greene, W., Seigel, G. M., and Stewart, W. C. (1997). L-deprenyl protects injured retinal precursor cells in vitro. Journal of Ocular Pharmacology and Therapeutics 13, 479–488.

Raine, C. 5. (1994). The Dale E. McFarlin Memorial Lecture: the immunology of the multiple sclerosis lesion. Ann Neurol 36, 561–72.

Ranscht, B., Clapshaw PA, Price J, Noble M, Seifert W (1982). Development of oligodendrocytes and schwann cells studied with a monoclonal antibody against galactocerebroside. Proc Natl Acad Sci USA 79, 2709–2713.

Ravikumar, R., Lakshmana, M. K., Rao, B. S. S., Meti, B. L., Bindu, P. N., and Raju, T. R. (1998). (-)-deprenyl attenuates spinal motor neuron degeneration and associated locomotor deficits in rats subjected to spinal cord ischemia. Exp Neurol 149, 123–129.

Reinhard, J. F., Jr., and JP, O. C. (1991). Measurement of tyrosine hydroxylase apoenzyme protein by enzyme-linked immunosorbent assay (ELISA): effects of 1-methyl-4-phenyl-1,2,3,6-tetrahydropyridine (MPTP) on striatal tyrosine hydroxylase activity and content. Anal Biochem 196, 296–301.

Revuelta, M., Venero, J. L., Machado, A., and Cano, J. (1997). Deprenyl induces GFAP immunoreactivity in the intact and injured dopaminergic nigrostriatal system but fails to counteract axotomy-induced degenerative changes. Glia 21, 204–216.

Reynolds, R.. and Wilkin, G. P. (1988). Development of macroglial cells in rat cerebellum. II. An in situ immunohistochemical study of oligodendroglial lineage from precursor to mature myelinating cell. Development 102, 409–25.

Richardson, W. D., Pringle, N., Mosley, M. J., Westermark., B., and Dubois Dalcq, M. (1988). A role for platelet-derived growth factor in normal gliogenesis in the central nervous system. Cell 53, 309–19.

Richter, C. (1993). Pro-oxidants and mitochondrial Ca2+: their relationship to apoptosis and oncogenesis. FEBS Lett 325, 104–7.

Richter, C., Gogvadze, V., Laffranchi, R., Schlapbach, R., Schweizer, M., Suter, M., Walter, P., and Yaffee, M. (1995). Oxidants in mitochondria: from physiology to diseases. Biochim Biophys Acta 1271, 67–74.

Riparbelli, M. G., Callaini, G., Tripodi, S. A., Cintorino, M., Tosi, P., and Dallai, R. (1995). Localization of the Bcl-2 protein to the outer mitochondrial membrane by electron microscopy. Exp Cell Res 221, 363–369.

Rodriguez-Gomez, J. A., Venero, J. L., Vizuete, M. L., Cano, J., and Machado, A. (1997). Deprenyl induces the tyrosine hydroxylase enzyme in the rat dopaminergic nigrostriatal system. Mol Brain Res 46, 31–38.

Rohatagi, S., Barrett, J. S., Dewitt, K. E., and Morales, R. J. (1997a). Integrated pharmacokinetic and metabolic modeling of selegiline and metabolites after transdermal administration. Biopharmaceutics & Drug Disposition 18, 567–584.

Rohatagi, S., Barrett, J. S., McDonald, L. J., Morris, E. M., Damow, J., and DiSanto, A. R. (1997b). Selegiline percutaneous absorption in various species and metabolism by human skin. Pharmaceutical Research 14, 50–55.

Rothblat, D. S., and Schneider, J. S. (1998). The effects of L-deprenyl treatment, alone and combined with GM1 ganglioside, on striatal dopamine content and substantia nigra pars compacta neurons. Brain Res 779, 226–230.

Rotwein, P., Burgess, S. K., Milbrandt, J. D., and Krause, J. E. (1988). Differential expression of insulin-like growth factor genes in rat central nervous system. Proc Natl Acad Sci U S A 85, 265–9.

Rukenstein, A., Rydel, R. E., and Greene, L. A. (1991). Multiple agents rescue PC12 cells from serum-free cell death by translation- and transcription-independent mechanisms. J Neurosci 11, 2552–2563.

Salo, P. T., and Tatton, W. G. (1992). Deprenyl reduces the death of motorneurons caused by axotomy. J Neurosci Res 31, 394–400.

Sanchez, A., Alvarez, A. M., Benito, M., and Fabregat, I. (1997). Cycloheximide prevents apoptosis, reactive oxygen species production, and glutathione depletion induced by transforming growth factor beta in fetal rat hepatocytes in primary culture. Hepatology 26, 935–943.

Saneto, R. P., and de Vellis, J. (1985). Characterization of cultured rat oligodendrocytes proliferating in a serum-free, chemically defined medium. Proc Nati Acad Sci U S A 82, 3509–13.

Saunders, J. W. (1966). Death in embryonic systems. Science 2454, 604–612.

Schmidt, D. E., Ebert, M. H., Lynn, J. C., and Whetsell, W. O. (1997). Attenuation of 1- methyl-4-phenylpyridiium (MPP+) neurotoxicity by deprenyl in organotypic canine Substantia nigra cultures. J Neural Transm 104, 875–885.

Scolding, N. J., Zajicek, J. P., Wood, N., and Compston, D. A. (1994). The pathogenesis of demyelinating disease. Prog Neurobiol 43, 143–73.

Scorrano, L., Nicolli, A., Basso, E., Petronilli, V., and Bernardi, P. (1997). Two modes of activation of the permeability transition pore: The role of mitochondrial cyclophilin. Mol Cell Biochem 174, 181–184.

Scorrano, L., Petronilli, V., and Bernardi, P. (1997). On the voltage dependence of the mitochondrial permeability transition pore - A critical appraisal. J Biol Chem 272, 12295–12299.

Selmaj, K., Raine, C. S., Farooq, M., Norton, W. T., and Brosnan, C. F. (1991). Cytokine cytotoxicity against oligodendrocytes. Apoptosis induced by lymphotoxin. J Immunol 147, 1522–9.

Selmaj, K. W., and Raine, C. S. (1988). Tumor necrosis factor mediates myelin and oligodendrocyte damage in vitro. Ann Neurol 23, 339–46.

Semkova, I., Wolz, P., Schilling, M., and Krieglstein, J. (1996). Selegiline enhances NGF synthesis and protects central nervous system neurons from excitotoxic and ischemic damage. Eur J Pharmacol 315, 19–30.

Sendtner, M., Schmalbruch, H., Stockli, K. A., Carroll, P., Kreutzberg, G. W., and Thoenen, H. (1992). Ciliary neurotrophic factor prevents degeneration of motor neurons in mouse mutant progressive motor neuronopathy [see comments]. Nature 358, 502–4.

Seniuk, N. A., Henderson, J. T., Tatton, W. G., and Roder, J. C. (1994). Increased CNTF gene expression in process-bearing astrocytes following injury is augmented by R(-)-deprenyl. J Neurosci Res 37, 278–86.

Seniuk-Tatton, N. A., Henderson, J. T., and Roder, J. C. (1995). Neurons express ciliary neurotrophic factor mRNA in the early postnatal and adult rat brain. J Neurosci Res 41, 663–76.

Sestili, P., Cattabeni, F., and Cantoni, O. (1996). Direct excision of 50 kb pair DNA fragments from megabase-sized fragments produced during apoptotic cleavage of genomic DNA. FEBS Letters 396, 337–342.

Shemer, J., Raizada, M. K., Masters, B. A., Ota, A., and LeRoith, D. (1987)Insulin-like growth factor I receptors in neuronal and glial cells. Characterization and biological effects in primary culture. J Biol Chem 262, 7693–9.

Sheratt, H. S. A. (1991). Mitochondria:structure and function. Rev Neurol (Paris) 147, 417–430.

Shirvan, A., Ziv, I., Barzilai, A., Djaldeti, R., Zilkh Faib, R., Michlin, T., and Melamed, E. (1997). Induction of mitosis-related genes during dopamine-triggered apoptosis in sympathetic neurons. J Neural Transm Suppl 50, 67–78.

Siegel, 5. (1956). Non-parametric statistics for the behavioral sciences (New York: McGraw-Hill Book Company), pp. 127–136.

Simon, J., and Neubert, W. J. (1996). The pathogenesis of multiple sclerosis: reconsideration of the role of viral agents and defence mechanisms. Med Hypotheses 46, 537–43.

Small, R. K., Riddle, P., and Noble, M. (1987). Evidence for migration of oligodendrocyte--type-2 astrocyte progenitor cells into the developing rat optic nerve. Nature 328, 155–7.

Soto, A. M., and Sonnenschein, C. (1985). The role of estrogens on the proliferation of human breast tumor cells (MCF-7). J Steroid Biochem 23, 87–94.

Spooren, W. P., Gentsch, C., and Wiessner, C. (1998). TUNEL-positive cells in the substantia nigra of C57BL/6 mice after a single bolus of 1-methyl-4-phenyl-1,2,3,6-tetrahydropyridine. Neuroscience 85, 649–51; discussion 653.

Su, J. H., Deng, G. M., and Cotman, C. W. (1997). Bax protein expression is increased in Alzheimer's brain: Correlations with DNA damage, Bcl-2 expression, and brain pathology. J Neuropathol Exp Neurol 56, 86–93.

Suarez-Kurtz, G., and Bianchi, C. P. (1970). Sites of action of SKF 525-A in nerve and muscle. J Pharmacol Exp Ther 172, 33–43.

Sunaga, K., Takahashi, H., Chuang, D. M., and Ishitani, R. (1995). Glyceraldehyde-3- phosphate dehydrogenase is over-expressed during apoptotic death of neuronal cultures and is recognized by a monoclonal antibody against amyloid plaques from Alzheimer's brain. Neurosci Lett 200, 133–136.

Susin, S. A., Zamzami, N., Castedo, M., Hirsch, T., Marchetti, P., Macho, A., Daugas, E., Geuskens, M., and Kroemer, G. (1996). Bcl-2 inhibits the mitochondrial release of an apoptogenic protease. J Exp Med 184, 1331–41.

Susin, S. A., Zamzami, N., and Kroemer, G. (1996). The cell biology of apoptosis: evidence for the implication of mitochondria. Apoptosis 1, 231–242.

Szuchet, S., Polak, P. E., and Yim, S. H. (1986). Mature oligodendrocytes cultured in the absence of neurons recapitulate the ontogenic development of myelin membranes. Dev Neurosci 8, 208–21.

Tatton, N. A., and Kish, S. J. (1997). In situ detection of apoptotic nuclei in the substantia nigra compacta of 1-methyl-4-phenyl-1,2,3,6-tetrahydropyridine-treated mice using terminal deoxynucleotidyl transferase labelling and acridine orange staining. Neuroscience 77, 1037–48.

Tatton, W., Ju, W, Wadia, J., Ansari, K., Zhang, F., Buys, Y., and Seniuk, N. (1994). (-)- Deprenyl reduces neuronal apoptosis by maintaining Bcl-2 synthesis and mitochondrial membrane potential. Movement Disorders 9, 4.

Tatton, W. G., and Chalmers Redman, R. M. (1996). Modulation of gene expression rather than monoamine oxidase inhibition: (-)-deprenyl-related compounds in controlling neurodegeneration. Neurology 47, 5171–83.

Tatton, W. G., Chalmers Redman, R. M., Ju, W. Y., Wadia, J., and Tatton, N. A. (1997). Apoptosis in neurodegenerative disorders: potential for therapy by modifying gene transcription. J Neural Transm Suppl 49, 245–68.

Tatton, W. G., and Greenwood, C. E. (1991). Rescue of dying neurons: a new action for deprenyl in MPTP parkinsonism. J Neurosci Res 30, 666–72.

Tatton, W. G., Ju, W. J. H., Wadia, J., and Tatton, N. A. (1996). Reduction of neuronal apoptosis by small molecules: promise for new approaches to neurological therapy. In Neuroprotection and Neurodegeneration, W. Olanow, M. Youdim and P. Jenner, eds. (New York: Academic Press Ltd.), pp. 209–229.

Tatton, W. G., Ju, W. Y., Holland, D. P., Tai, C., and Kwan, M. (1994). (-)-Deprenyl reduces PC12 cell apoptosis by inducing new protein synthesis. J Neurochem 63, 1572–

Tatton, W. G., Seniuk, N. A., Ju, W. Y. H., and Ansari, K. S. (1993). Reduction of nerve cell death by deprenyl without monoamine oxidase inhibition. In Monoamine Oxidase Inhibitors In Neurological Diseases, A. Lieberman, ed. (New York: Raven Press).

Temple, S., and Raff, M. C. (1985). Differentiation of a bipotential glial progenitor cell in a single cell microculture. Nature 313, 223–5.

Thiffault, C., Aumont, N., Quirion, R., and Poirier, J. (1995). Effect of MPTP and L- deprenyl on antioxidant enzymes and lipid peroxidation levels in mouse brain. J Neurochem 65, 2725–2733.

Thiffault, C., LamarreTheroux, L., Quirion, R., and Poirier, J. (1997). L-deprenyl and MDL72974 do not improve the recovery of dopaminergic cells following systemic administration of MPTP in mouse. Mol Brain Res 44, 238–244.

Thoenen, H. (1991). The changing scene of neurotrophic factors. Trends Neurosci 14, 165–70.

Thomas, L. B., Gates, D. J., Richfield, E. K., TF, O. B., Schweitzer, J. B., and Steindler, D. A. (1995). DNA end labeling (TUNEL) in Huntington's disease and other neuropathological conditions. Exp Neurol 133, 265–72.

Tienari, P. J. (1994). Multiple sclerosis: multiple etiologies, multiple genes? Ann Med 26, 259–69.

Todd, K. G., and Butterworth, R. F. (1998). Increased neuronal cell survival after 1- deprenyl treatment in experimental thiamine deficiency. J Neurosci Res 52, 240–246.

Trapp, B. D., Nishiyama, A., Cheng, D., and Macldin, W. (1997). Differentiation and death of premyelinating oligodendrocytes in developing rodent brain. J Cell Biol 137, 459–68.

Travis, J. (1994). Glia: the brains other cells. Science 266, 970–972.

Troy, C. M., and Shelanski, M. L. (1994). Down-regulation of copper/zinc superoxide dismutase causes apoptotic death in PC12 neuronal cells. Proc Natl Acad Sci U S A 91, 6384–7.

Ueda, K., Yagami, T., Kageyama, H., and Kawasaki, K. (1996). Protein kinase inhibitor attenuates apoptotic cell death induced by amyloid beta protein in culture of the rat cerebral cortex. Neurosci Lett 203, 175–178.

Vaglini, F., Pardini, C., Cavalletti, M., Maggio, R., and Corsini, G. U. (1996). L-deprenyl fails to protect mesencephalic dopamine neurons and PC12 cells from the neurotoxic effect of 1-methyl-4-phenylpyridinium ion. Brain Res 741, 68–74.

van de Water, B., Zoeteweij, J. P., De Bont, H. J., Mulder, G. J., and Nagelkerke, J. F. (1994). Role of mitochondrial Ca2+ in the oxidative stress-induced dissipation of the mitochondrial membrane potential. J Biol Chem. 269, 14546–14552.

Van Schravendijk, C. F., Hooghe Peters, E. L., De Meyts, P., and Pipeleers, D. G. (1984). Identification and characterization of insulin receptors on foetal-mouse brain-cortical cells. Biochem J 220, 165–72.

Vaux, D. L., Haecker, G., and Strasser, A. (1994). An evolutionary perspective on apoptosis. Cell 76, 777–9.

Vizuete, M. L., Steffen, V., Ayala, A., Cano, J., and Machado, A. (1993). Protective effect of deprenyl against 1-methyl-4-phenylpyridiium neurotoxicity in rat striatum. Neurosci Lett 152, 113–6.

Wadia, J. S., Chalmers Redman, R. M. E., Ju, W. J. H., Carlile, G. W., Phillips, J. L., Fraser, A. D., and Tatton, W. G. (1998). Mitochondrial membrane potential and nuclear changes in apoptosis caused by serum and nerve growth factor withdrawal: time course and modification by (−)-deprenyl. J Neurosci 18, 932–47.

Warf, B. C., Fok Seang, J., and Miller, R. H. (1991). Evidence for the ventral origin of oligodendrocyte precursors in the rat spinal cord. J Neurosci 11, 2477–88.

Werner, H., Woloschak, M., Adamo, M., Shen Orr, Z., Roberts, C. T., Jr., and LeRoith, D. (1989). Developmental regulation of the rat insulin-like growth factor I receptor gene. Proc Natl Acad Sci U S A 86, 745 1–5.

Wiggins, R. C. (1982). Myelin development and nutritional insufficiency. Brain Res 257, 151–75.

Wood, P. M., and Bunge, R. P. (1986). Myelination of cultured dorsal root ganglion neurons by oligodendrocytes obtained from adult rats. J Neurol Sci 74, 153–69.

Wu, R. M., Murphy, D. L., and Chiueh, C. C. (1995). Neuronal protective and rescue effects of deprenyl against MPP+ dopaminergic toxicity. J Neural Transm (General Section) 100, 53–61.

Wyllie, A. H. (1987). Apoptosis: cell death in tissue regulation. J Pathol 153, 313–6.

Wyllie, A. H. (1980). Glucocorticoid-induced thymocyte apoptosis is associated with endogenous endonuclease activation. Nature 284, 555–556.

Wyllie, A. H., Beattie, G. J., and Hargreaves, A. D. (1981). Chromatin changes in apoptosis. Histochem J 13, 681–92.

Xiang, H., Kinoshita, Y., Knudson, C. M., Korsmeyer, S. J., Schwartzkroin, P. A., and Morrison, R. S. (1998). Bax involvement in p53-mediated neuronal cell death. J Neurosci 18, 1363–1373.

Yang, J., Liu, X. S., Bhalla, K., Kim, C. N., Ibrado, A. M., Cai, J. Y., Peng, T. I., Jones, D. P., and Wang, X. D. (1997). Prevention of apoptosis by Bcl-2: Release of cytochrome c from mitochondria blocked. Science 275, 1129–1132.

Yasuda, T., Grinspan, J., Stern, J., Franceschini, B., Bannerman, P., and Pleasure, D. (1995). Apoptosis occurs in the oligodendroglial lineage, and is prevented by basic fibroblast growth factor. J Neurosci Res 40, 306–17.

Yoshiyama, Y., Yamada, T., Asanuma, K., and Asahi, T. (1994). Apoptosis related antigen, Le(Y) and nick-end labeling are positive in spinal motor neurons in amyotrophic lateral sclerosis. Acta Neuropathol Berl 88, 207–11.

Zamzami, N., Marchetti, P., Castedo, M., Hirsch, T., Susin, S. A., Masse, B., and Kroemer, G. (1996). Inhibitors of permeability transition interfere with the disruption of the mitochondrial transmembrane potential during apoptosis. FEBS Lett 384, 53–7.

Zeller, N. K., Behar, T. N., Dubois Dalcq, M. E., and Lazzarini, R. A. (1985). The timely expression of myelin basic protein gene in cultured rat brain oligodendrocytes is independent of continuous neuronal influences. J Neurosci 5, 2955–62.

Zeng, Y. C., Bongrani, S., Bronzetti, E., Cadel, S., Ricci, A., Valsecchi, B., and Amenta, F. (1995). Effect of long-term treatment with L-deprenyl on the age-dependent microanatomical changes in the rat hippocampus. Mechanisms of Ageing and Development 79, 169–185.

Zhang, F., Richardson, P. M., Holland, D. P., Guo, Q., and Tatton, W. G. (1995). CNTF or (−)-deprenyl in immature rats: Survival of axotomized facial motoneurons and weight loss. J Neurosci Res 40, 564–570.

Zhang, X., Zuo, D. M., Davis, B. A., Boulton, A. A., and Yu, P. H. (1996). Immunohistochemical evidence of neuroprotection by R(−)-deprenyl and N-(2-hexyl)-N-methylpropargylamine on DSP-4-induced degeneration of rat brain noradrenergic axons and terminals. J Neurosci Res 43, 482–489.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A method for increasing survival of oligodendrocytes, comprising administering an effective amount of a deprenyl compound to a patient in need there of, wherein the deprenyl compound is represented by the structure:

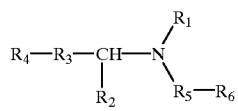

in which
- $R_1$ is hydrogen, alkyl, alkenyl, alkynyl, aralkyl, alkylcarbonyl, arylcarbonyl, alkoxycarbonyl, or aryloxycarbonyl;
- $R_2$ is hydrogen or alkyl;
- $R_3$ is a single bond, alkylene, or —(CH$_2$)$_n$—X—(CH$_2$)$_m$; in which X is O, S, or N-methyl; m is 1 or 2; and n is 0, 1, or 2;
- $R_4$ is alkyl, alkenyl, alkynyl, heterocycylyl, aryl or aralkyl; and
- $R_5$ is alkylene, alkenylene, alkynylene and alkoxylene; and
- $R_6$ is $C_3$–$C_6$ cycloalkyl or

$R_2$ and $R_4$–$R_3$ are joined to form, together with the methine to which they are attached, a cyclic or polycyclic group;

and pharmaceutically acceptable salts thereof, such that survival of oligodendrocytes is increased.

2. The method of claim 1, wherein $R_1$ is a group that can be removed in vivo.
3. The method of claim 1, wherein $R_1$ is hydrogen.
4. The method of claim 1, wherein $R_1$ is alkyl.
5. The method of claim 1, wherein $R_1$ is methyl.
6. The method of claim 1, wherein $R_2$ is methyl.
7. The method of claim 1, wherein $R_3$ is methylene.
8. The method of claim 1, wherein $R_4$ is aryl.
9. The method of claim 1, wherein $R_5$ is phenyl.
10. The method of claim 1, wherein $R_5$ is methylene.
11. The method of claim 1, wherein $R_6$ is

12. The method of claim 1, wherein the deprenyl compound is represented by the structure:

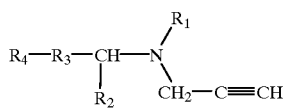

in which
- $R_1$ is hydrogen, alkyl, alkenyl, alkynyl, aralkyl, alkylcarbonyl, arylcarbonyl, alkoxycarbonyl, or aryloxycarbonyl;
- $R_2$ is hydrogen or alkyl;
- $R_3$ is a bond or methylene; and
- $R_4$ is aryl or aralkyl; or
- $R_2$ and $R_4$–$R_3$ are joined to form, together with the methine to which they are attached, a cyclic or polycyclic group;

and pharmaceutically acceptable salts thereof.

13. The method of claim 1, wherein the deprenyl compound is represented by the structure:

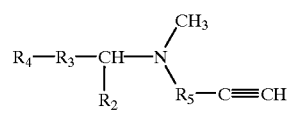

in which
- $R_1$ is hydrogen or alkyl;
- $R_3$ is a bond or methylene; and
- $R_4$ is aryl or aralkyl; or
- $R_2$ and $R_4$–$R_3$ are joined to form, together with the methine to which they are attached, a cyclic or polycyclic group;
- $R_5$ is alkylene, alkenylene, alkynylene and alkoxylene;

and pharmaceutically acceptable salts thereof.

14. The method of claim 1, wherein the deprenyl compound is represented by the structure:

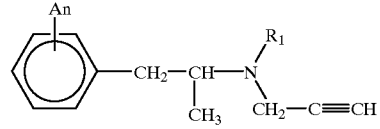

in which
- $R_1$ is hydrogen, alkyl, alkenyl, alkynyl, aralkyl, alkylcarbonyl, arylcarbonyl, alkoxycarbonyl, or aryloxycarbonyl;
- A is a substituent independently selected for each occurence from the group consisting of halogen, hydroxyl, alkyl, alkoxyl, cyano, nitro, amino, —CF$_3$, or azido;
- n is 0 or an integer from 1 to 5;

and pharmaceutically acceptable salts thereof.

15. The method of claim 1, wherein said patient is a human.
16. The method of claim 1, wherein said deprenyl compound is (−)-desmethyldeprenyl.
17. The method of claim 12, wherin said deprenyl compound is:

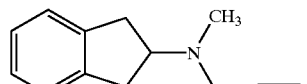

* * * * *

UNITED STATES PATENT AND TRADEMARK OFFICE
CERTIFICATE OF CORRECTION

PATENT NO.     : 6,492,427 B2
DATED          : December 10, 2002
INVENTOR(S)    : L. Sai Latha Shankar et al.

It is certified that error appears in the above-identified patent and that said Letters Patent is hereby corrected as shown below:

Column 81,
Line 25, please replace the formula "—C≡CH" with -- —C≡CH, or --.
Line 35, please replace "in vivo" with -- *in vivo* --.

Column 82,
Line 43, add -- carboxyl -- after "amino" and before "$CF_3$, or."

Signed and Sealed this

Thirtieth Day of December, 2003

JAMES E. ROGAN
*Director of the United States Patent and Trademark Office*